United States Patent
Peterson et al.

(10) Patent No.: US 6,420,365 B1
(45) Date of Patent: Jul. 16, 2002

(54) IMIDAZOPYRIDINES AND RELATED DERIVATIVES AS SELECTIVE MODULATORS OF BRADYKININ $B_2$ RECEPTORS

(75) Inventors: John M. Peterson; Alan Hutchison, both of Madison; Kenneth Shaw, Weston; Kevin Hodgetts, Killingworth; George D. Maynard, Clinton; Richard Lew, Hamden, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/765,159

(22) Filed: Jan. 17, 2001

Related U.S. Application Data

(60) Provisional application No. 60/176,701, filed on Jan. 18, 2000.

(51) Int. Cl.$^7$ ..................... A61K 31/435; C07D 471/04
(52) U.S. Cl. ................ 514/248; 514/248; 514/249; 514/257; 514/300; 544/184; 544/236; 544/281; 544/127; 544/61; 544/350; 546/121
(58) Field of Search .................... 546/121; 544/184, 544/236, 281, 350, 127, 61; 514/243, 248, 249, 257, 300

(56) References Cited

U.S. PATENT DOCUMENTS

| | | | |
|---|---|---|---|
| 5,438,064 A | 8/1995 | Mobilio et al. | 514/300 |
| 5,574,042 A | 11/1996 | Oku et al. | 514/313 |
| 6,013,654 A * | 1/2000 | TenBrink | 514/300 |

FOREIGN PATENT DOCUMENTS

JP 09-176165 7/1997

OTHER PUBLICATIONS

International Search Report for PCT/US01/01601 (May 2001).

* cited by examiner

*Primary Examiner*—Bernard Dentz
(74) *Attorney, Agent, or Firm*—Leslie-Anne Horvath; Seth A. Fidel

(57) ABSTRACT

Disclosed are compounds of the formula:

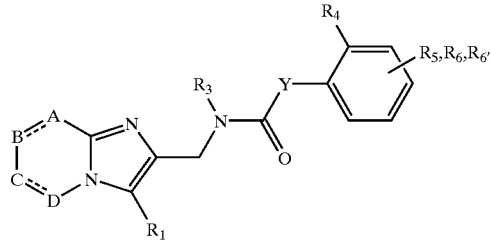

or the pharmaceutically acceptable non-toxic salts thereof wherein A, B, C, D, Y, $R_1$, $R_3$, $R_4$, $R_5$, and $R_6$ are variables defined herein, which compounds are modulators of Bradykinin $B_2$ receptors. These compounds are useful in the diagnosis and treatment of renal diseases, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility, glaucoma, pain, asthma, and rhinitis and for the increase of permeability of the blood-brain barrier or the blood-brain-tumor barrier.

40 Claims, No Drawings

IMIDAZOPYRIDINES AND RELATED DERIVATIVES AS SELECTIVE MODULATORS OF BRADYKININ B$_2$ RECEPTORS

This application claims priority from U.S. provisional patent application No. 60/176,701, filed Jan. 18, 2000.

Field of the Invention

This invention relates to certain imidazopyridines and related azacyclic derivatives which when appropriately substituted are selective modulators of Bradykinin B$_2$ receptors. This invention also relates to pharmaceutical compositions comprising such compounds. It further relates to the use of such compounds in treating a variety of central and peripheral disorders. Additionally, compounds of this invention are useful as positive controls in assays for BK-2 receptor activity and when appropriately labeled as probes for the localization of BK-2 receptors in tissue sections.

BACKGROUND

Bradykinin (BK), a nonapeptide, and the closely related decapeptide kallidin (Lys-BK), are produced by proteolytic cleavage of high molecular weight kininogen by plasma kallikreins. The effects of bradykinin and kallidin are mediated by specific seven transmembrane G-protein coupled receptors.

The existence of two bradykinin receptor subtypes has been unequivocally confirmed within the last six years. The expression and cloning of a rat bradykinin receptor, now known to be a BK-2 receptor, was first reported followed by the cloning and pharmacological characterization of a human BK-2 receptor. The expression and cloning of a human bradykinin (B$_1$) receptor has also been described.

Both BK and kallidin activate the B$_2$ receptor while only kallidin is active at the B$_1$ receptor. However, both compounds are rapidly cleaved to produce B$_1$ receptor agonists, and then further degraded by kinases to produce inactive peptides. The instability of BK and kallidin suggests that these peptides act locally. Both receptors are expressed in a number of peripheral tissues as well as in the Central Nervous System (CNS).

The B$_2$ receptor is expressed constitutively in a variety of tissues and accounts for the majority of the acute pharmacological effects of bradykinin. The B$_1$ receptor is inducibly expressed and appears to act predominantly in pathophysiological conditions. The BK-1 receptor has been especially implicated in persistent hyperalgesia and chronic inflammation.

Bradykinin is an effector of a number of inflammatory responses including bronchoconstriction, plasma extravasation, release of prostaglandins/leukotrienes, smooth muscle contraction/relaxation and nociception. Bradykinin and the related peptide kallidin have been implicated in a number of disease conditions, including but not limited to pain, rhinitis, anaphylaxis, inflammatory bowel disease, vascular permeability, algesia, vasodilataion, inflammatory response, hypotension associated with sepsis, bronchopulmonary disorders including asthma, and increased cell proliferation. Antagonists of the BK-2 receptor are useful in treating these conditions. Additionally bradykinin has been implicated in increased glucose uptake, and decreased blood glucose concentration. Therefore agonists of the BK-2 receptor may be useful in the treatment of Type II diabetes. An increased permeability of the blood-brain barrier due to bradykinin has also been reported. Thus, agonists of the BK-2 receptor may also be used to increase the brain levels of pharmaceutical compounds used to treat central nervous system disorders when administered with these compounds. Therefore, compounds that modulate the bradykinin B$_2$ (BK-2) receptor as agonists or antagonists would have considerable therapeutic benefit.

A number of tissues and cultured cell lines have been assessed for the presence of bradykinin receptors using radiolabeled bradykinin or a radiolabeled bradykinin analogue as a probe (See Hall, Gen. Pharma., 1997, 28: 1–6, for a compilation of such studies.). Although bradykinin and its analogues exhibit high affinity for bradykinin receptors there are some difficulties in using these ligands as receptor localization probes. Bradykinin binds to both BK-1 and BK-2 receptors and therefore cannot be used to distinguish receptor subtypes. Also bradykinin and many of its peptide analogues are susceptible to rapid degradation by kininases, leading to experimental difficulties. Nonpeptidic ligands are not susceptible to kininase activity. Therefore, small molecules that bind with high affinity and high selectivity to BK-2 receptors are especially desirable tools for BK-2 localization studies.

DESCRIPTION OF THE RELATED ART

Various compounds have been prepared as modulators of BK-2 receptors. The following disclose non-peptidic compounds that modulate Bradykinin B$_2$ receptors: EP-622361-A1, WO 98/42672, WO 97/41104, WO 97/28153, WO 96/13485, EP-596406-A1, EP-835659-A1, EP-808-838-A1, EP-796-848-A1, WO 98/03503, WO 97/24349, U.S. Pat. No. 5,438,064, U.S. Pat. No. 5,216,165, U.S. Pat. No. 5,212,182, WO 97/30048, EP 790239-A1, U.S. Pat. No. 5,510,380, U.S. Pat. No. 5,817,756.

The compounds most closely related structurally to the present invention are a series of imidazopyridine ureas described in JP 95-350957 as cholesterol acyltransferase inhibitors. None of the compounds from JP 95-350957 are described as bradykinin antagonists.

SUMMARY OF THE INVENTION

This invention provides novel compounds of Formula I (shown below) and pharmaceutical compositions comprising compounds of Formula I. Such compounds exhibit high selectivity for bradykinin B$_2$ receptors. Compounds of Formula I also bind with high affinity to these receptors.

The invention further provides methods of treating patients suffering from certain inflammatory disorders and other conditions mediated by bradykinin. The invention also provides methods of treating patients (humans and non-humans) suffering from conditions in which agonism of the BK-2 receptor may prove beneficial. Treatment of humans, domesticated companion animals (pets) or livestock animals suffering such conditions with an effective amount of a compound of the invention is contemplated by the invention.

In a separate aspect, the invention provides methods of using compounds of this invention as positive controls in assays for BK-2 receptor activity and using appropriately labeled compounds of the invention as probes for the localization of BK-2 receptors in tissue sections.

A broad aspect of the invention is directed to compounds of Formula I:

Formula I

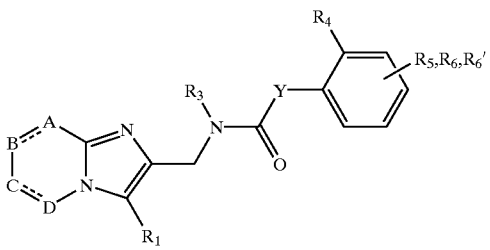

or the pharmaceutically acceptable non-toxic salts thereof wherein:

represents a nitrogen-containing ring system, in which not more than two of A, B, C, or D represent nitrogen and remaining ring members are carbon, and which nitrogen-containing ring system is optionally substituted with up to four substituents independently selected from:
  (i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyN$R_7R_8$, N$R_7R_8$, N$R_7$CO$R_8$, CON$R_7R_8$, wherein $R_7$ and $R_8$ are same or different and represent hydrogen, or straight or branched chain lower alkyl, or $R_7$ and $R_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and
  (iii) O(CH$_2$)$_n$CO$_2$R$_A$ (where n=1,2,3, or 4), COR$_A$, and CO$_2$R$_A$ wherein R$_A$ represents hydrogen, or straight or branched chain lower alkyl;

$R_1$ is arylalkyl, heteroarylalkyl, or allyl each of which is optionally substituted directly or through a O(CH$_2$)$_n$ linker (where n=1,2, 3 or 4) with up to three substituents independently selected from:
  (i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyN$R_{7'}R_{8'}$, N$R_{7'}R_{8'}$, N$R_{7'}$CO$R_{8'}$, CON$R_{7'}R_{8'}$, wherein $R_{7'}$ and $R_{8'}$ are the same or different and represent hydrogen, or straight or branched chain lower alkyl, or $R_7'$ and $R_8'$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
  (iii) O(CH$_2$)$_n$CO$_2$R$_{A'}$ (where n=1,2,3, or 4), COR$_{A'}$, CO$_2$R$_{A'}$, wherein R$_{A'}$ represents hydrogen, or straight or branched chain lower alkyl,
  (iv) SO$_2$R$_{A'}$, NHSO$_2$R$_{A'}$, SO$_2$NHR$_{A'}$, SO$_2$NHCOR$_{A'}$, CONHSO$_2$R$_{A'}$, wherein R$_{A'}$ is as defined above,
  (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy);

$R_3$ represents straight or branched chain lower alkyl;
$R_4$ represents halogen or trifluoromethyl;
$R_5$, $R_6$, and $R_{6'}$ are the same or different and represent
  (i) hydrogen, trifluoromethyl, trifluoromethoxy, nitro, cyano, lower alkyl, halogen, aminomethyl, mono or dialkylamino, mono or dialkylaminomethyl, wherein each alkyl is independently lower alkyl, or $C_1$–$C_6$alkoxyaminoalkyl where the amino is mono or disubstituted with straight or branched chain lower alkyl;
  (ii) $C_1$–$C_6$ alkoxy (with the proviso that $R_5$, $R_6$, or $R_{6'}$ may not be $C_1$–$C_6$ alkoxy when located ortho to Y) which is optionally substituted with
    (a) $C_1$–$C_6$ alkoxy, $C_1$–$C_6$ alkylthio, amino, hydroxy, halogen, haloalkyl, mono or di($C_1$–$C_6$) alkylamino, morpholino, or thiomorpholino
    (b) mono or di($C_1$–$C_{10}$)alkylamino$_1$, wherein said mono or di($C_1$–$C_{10}$)alkylamino$_1$, is substituted with aryl, arylalkyl, heteroarylalkyl, heteroarylalkyl, $C_3$–$C_7$ cycloalkyl, ($C_3$–$C_7$ cycloalkyl)$C_1$–$C_4$alkyl, $C_3$–$C_7$heterocycloalkyl, ($C_3$–$C_7$ cycloalkyl)$C_1$–$C_4$alkyl wherein each aryl, heteroaryl, cycloalkyl, or heterocycloalkyl group substituting said mono or di($C_1$–$C_{10}$)alkylamino$_1$ is optionally substituted by alkyl, oxo, halogen, hydroxyl, trifluoromethyl, trifluromethoxy, or alkoxy;

$R_4$ and $R_5$ are joined to form a 5, 6, or 7 membered carbocyclic or heterocyclic aromatic ring which is optionally substituted with up to four substitutents selected from:
  (i) halogen, nitro, trifluoromethyl, cyano, hydroxyl, $C_1$–$C_6$ alkyl, amino, $C_1$–$C_6$ alkoxy, aminomethyl, mono or dialkylamino, mono or dialkylaminomethyl (wherein each alkyl is independently lower alkyl),
  (ii) $C_1$–$C_6$alkoxyN$R_7"R_8"$, N$R_7"R_8"$, CON$R_7"R_8"$, N$R_7"$CO$R_8"$, where $R_7"$ and $R_8"$ are the same or different and represent hydrogen or straight or branched chain lower alkyl, or $R_7"$ and $R_8"$ may be a 5, 6, or 7 membered heterocyclic ring, which is optionally substituted with halogen, nitro, trifluoromethyl, cyano, hydroxyl, lower alkyl, amino, mono or dialkylamino (wherein each alkyl is independently lower alkyl) or $C_1$–$C_6$ alkoxy,
  (iii) O(CH$_2$)$_n$CO$_2$R$_A"$ where n=1,2,3,4, COR$_A"$, or CO$_2$R$_A"$ where R$_A"$ represents hydrogen or straight or branched chain lower alkyl having 1–6 carbon atoms and $R_6$ and $R_{6'}$ are as defined above; and
Y represents a bond or CH$_2$, when Y=CH$_2$ it may be mono or disubstituted with a straight or branched chain lower alkyl, or straight or branched chain lower alkoxy having 1–6 carbon atoms.

DETAILED DESCRIPTION OF THE INVENTION

The novel compounds encompassed by the instant invention can be described by the following general formula Ia:

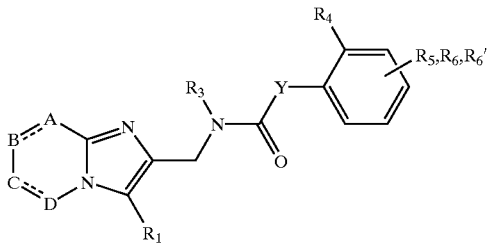

Formula Ia or the pharmaceutically acceptable non-toxic salts thereof wherein:

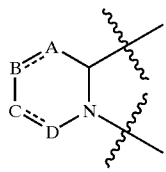

is as defined above for Formula I, $R_1$, $R_3$, and Y are as defined above;

$R_4$ represents hydrogen, halogen or trifluoromethyl; and $R_5$, $R_6$, and $R_6'$ are the same or different and represent hydrogen, trifluoromethyl, trifluoromethoxy, nitro, cyano, lower alkyl having 1–6 carbon atoms, $C_1$–$C_6$ alkoxy (with the proviso that $R_5$, $R_6$, and $R_6'$ may not be $C_1$–$C_6$ alkoxy when located ortho to Y in Formula Ia), halogen, aminomethyl, mono or dialkylaminomethyl (where each alkyl is independently lower ($C_1$–$C_6$) alkyl), and $C_1$–$C_6$ alkoxyaminoalkyl where the amino is mono or disubstituted with straight or branched chain lower alkyl having 1–6 carbon atoms.

Other novel compounds of Formula I may be comprised of compounds of general Formula Ib:

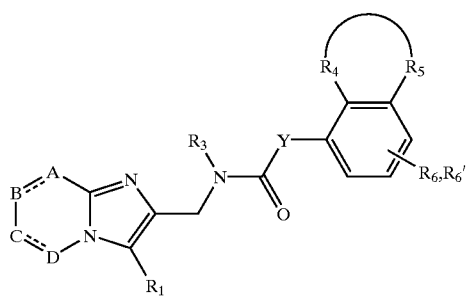

Formula Ib or the pharmaceutically acceptable non-toxic salts thereof wherein:

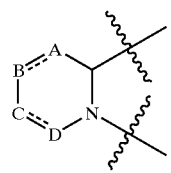

is as defined above, and $R_1$, $R_3$, and Y are as defined above;

$R_4$ and $R_5$ form a 5, 6, or 7 membered carbocyclic or heterocyclic aromatic ring which is optionally substituted with up to four substituents independently selected from:

halogen, nitro, trifluoromethyl, cyano, hydroxyl, $C_1$–$C_6$ alkyl, amino, $C_1$–$C_6$ alkoxy, aminomethyl, mono or dialkylamino, mono or dialkylaminomethyl (wherein each alkyl is independently lower alkyl), $C_1$–$C_6$alkoxyNR$_7$"R$_8$", NR$_7$"R$_8$", CONR$_7$"R$_8$", NR$_7$"COR$_8$", where R$_7$" and R$_8$" are the same or different and represent hydrogen or straight or branched chain lower alkyl, or R$_7$" and R$_8$" may be a 5, 6, or 7 membered heterocyclic ring, which is optionally substituted with halogen, nitro, trifluoromethyl, cyano, hydroxyl, lower alkyl, amino, mono or dialkylamino (wherein each alkyl is independently lower alkyl) or $C_1$–$C_6$ alkoxy, O(CH$_2$)$_n$CO$_2$R$_A$" where n=1,2,3,4, COR$_A$", or CO$_2$R$_A$" where R$_A$" represents hydrogen or straight or branched chain lower alkyl having 1–6 carbon atoms $R_6$, and $R_6'$ are the same or different and represent hydrogen, halogen, trifluoromethyl, trifluoromethoxy, nitro, cyano, lower alkyl, $C_1$–$C_6$ alkoxy (with the proviso that $R_6$ or $R_6'$ may not be $C_1$–$C_6$ alkoxy when located ortho to Y), aminomethyl, mono or dialkylamino, mono or dialkylaminomethyl, wherein each alkyl is independently a straight or branched chain lower alkyl, or $C_1$–$C_6$ alkoxyaminoalkyl where the amino is mono or disubstituted with straight or branched chain lower alkyl having 1–6 carbon atoms.

One preferred embodiment of the present invention encompasses compounds of Formula II and pharmaceutically acceptable salts thereof;

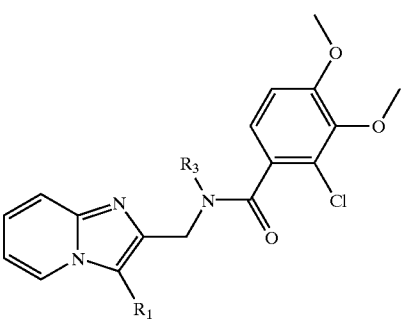

Formula II wherein $R_1$ and $R_3$ are as defined above.

In a more preferred embodiment the invention encompasses compound of Formula II and the pharmaceutically acceptable salts thereof wherein $R_3$ is isoamyl or n-pentyl, and $R_1$ is as defined above.

Another preferred embodiment of the present invention encompasses compounds of Formula III and the pharmaceutically acceptable salts thereof;

Formula III

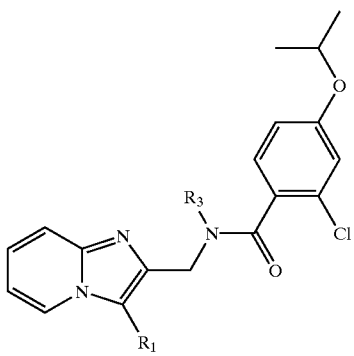

wherein $R_1$ and $R_3$ are as defined above.

In a more preferred embodiment the invention encompasses compound of Formula III and the pharmaceutically acceptable salts thereof wherein $R_3$ is isoamyl or n-pentyl, and $R_1$ is as defined above.

In another preferred embodiment, the present invention encompasses compounds of Formula IV Formula IV

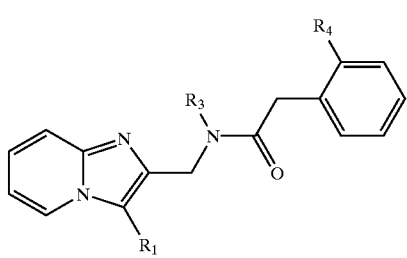

wherein:

$R_1$, and $R_3$ are as defined above and $R_4$ represents hydrogen, halogen or trifluoromethyl.

In a more preferred embodiment the invention encompasses compounds of Formula IV and the pharmaceutically acceptable salts thereof wherein $R_1$ is as defined above, $R_3$ is isoaamyl or n-pentyl, and $R_4$ represents chlorine, bromine, or trifluoromethyl.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)n-COOH$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

The term "aryl" in the present invention means a monocyclic or bicyclic aromatic group having preferably 6 to 10 carbon atoms, such as, for example, phenyl or naphthyl.

By "arylalkyl" or "heteroarylalkyl" in the present invention is meant a branched or straight-chain alkyl group having from 1 to about 6 carbon atoms and substituted on one of the carbon atoms by an optionally substituted aryl or heteroaryl ring, such as, for example, benzyl, phenethyl, methylpyridyl, ethylpyridyl, and the like.

By "alkyl" in the present invention is meant $C_1$–$C_{10}$ alkyl, i.e., straight or branched chain alkyl groups having 1–10 carbon atoms, preferably 1–6 carbon atoms ($C_1$–$C_6$ alkyl), such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_{10}$ alkyl groups are methyl, ethyl, propyl, butyl, cyclopropyl or cyclopropylmethyl.

By "lower alkyl" in the present invention is meant $C_1$–$C_6$ alkyl, i.e., straight or branched chain alkyl groups having 1–6 carbon atoms.

By "alkoxy" or "lower alkoxy" in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "halogen" in the present invention is meant fluorine, bromine, chlorine, and iodine.

By (hetero) cyclic ring is meant a ring that is either aliphatic or aromatic and optionally contains at least one hetero atom. Hetero atoms include nitrogen, sulfur, and oxygen. Examples of such (hetero) cyclic rings are cyclohexyl, cyclopentyl, piperidinyl, piperazinyl, pyrrolidinyl, morpholinyl, etc.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, imidazolyl, (iso)quinolinyl, naphthyridinyl, benzimidazolyl, and benzoxazolyl.

The structure of Formula I as shown in the specification and as used in the claims includes all possible tautomers and rotamers.

Selective agonists or antagonists of the bradykinin $B_2$ receptor provide compounds useful in treatment of renal diseases, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, for the increase of permeability of blood-brain barrier or bloodbrain-tumor barrier, pain, asthma, rhinitis. These interactions result in the pharmacological activities of these compounds.

The invention also provides pharmaceutical composition comprising compounds of the invention.

The invention also provides packaged pharmaceutical compositions comprising pharmaceutical compositions of the invention in a container and instructions for using the composition to treat a patient in need thereof. In one embodiment, the instructions are for using the composition to treat a patient suffering from a physiological disorder associated with an excess of or insufficient amount of bradykinin. The patient may be suffering, for example, from renal disease, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, asthma, rhinitis, brain cancer, or a brain tumor.

The invention further provides methods of treating patients in suffering from an inflammatory disorder with an amount of a compound of the invention sufficient to alter the symptoms of the inflammatory disorder. Inflammatory disorders that may be treated with a selective antagonist of the BK-2 receptor include restenosis after percutaneous transluminal coronary angioplasty, rhinitis, inflammation associated with brain trauma, stroke, sepsis, anaphylaxis, Meniere's disease, pancreatitis, ileus, inflammatory bowel disease, and bronchopulmonary disorders including asthma. The invention also provides methods of treating patients suffering from pain with a pain-reducing amount of a compound of the invention. Painful conditions that may be treated with an antagonist of the BK-2 receptor, include, but are not limited to inflammatory pain, postoperative pain, and vaginal inflammation and pain. The invention further provides a method of treating patients suffering from hypertension with an amount of compound of the invention sufficient to reduce blood pressure. Selective antagonists of the BK-2 receptor are useful as anti-hypertensives.

In a further aspect the invention provide a method of treating a patient suffering from Type II (adult-onset) diabetes with an amount of a compound of the invention sufficient to alter the symptoms. Selective agonists of the BK-2 receptor are useful for treating type II diabetes. The invention also provides methods of treating patients suffering from circulatory or cardiovascular disorders with an amount of a compound of the invention, that is a selective agonist of the BK-2 receptor, sufficient to reduce the symptoms of the circulatory of cardiovascular disorder. Such circulatory or cardiovascular disorders include, but are not limited to heart failure, peripheral circulatory disorders, myocardial infarction, ostmyocardial infarction syndrome, angina pectoris, retinochoroidal circulatory disorders, nd myocardial ischemia. Selective agonists of the BK-2 stimulate NO release and as such re useful for treating climacteric disturbance and male infertility. The invention provides methods of treating patients suffering from such disorders with an amount of a compound of the invention sufficient to reduce the symptoms of disorder.

Bradykinin has been shown to increase the permeability of blood-brain barrier and blood-brain tumor barrier. The invention provides a method of increasing the brain concentration of a CNS active compounds which comprises administering a patient in need of such treatment a compound of the invention, that is a selective agonist of the BK-2 receptor, along with a CNS active compound, and thereby increasing the brain concentration of the CNS active compound. In a particularly preferred embodiment the invention provides a method of increasing the brain concentration of anti-cancer and anti-tumor agents which comprises administering a patient suffering from brain cancer or a brain tumor a compound of the invention, that is a selective agonist of the BK-2 receptor, along with a anti-cancer and anti-tumor agent, and thereby increasing the brain concentration of the anti-cancer or anti-tumor agent.

Patients include human and non-human animals, such as domestic pets and farm animals (for example, dogs, cats, swine, sheep, horses, cattle, etc.).

The present invention also pertains to methods of inhibiting the binding of bradykinin to the bradykinin receptors, especially BK-2 receptors which methods involve contacting a compound of the invention with cells expressing bradykinon receptors, (preferably BK-2 receptors) wherein the compound is present at a concentration sufficient to inhibit the binding of bradykinin to bradykinin receptors in vitro. This method includes inhibiting the binding of bradykinin to bradykinin receptors in vivo, e.g., in a patient given an amount of a compound of formula I or any of the subformulae thereof, that would be sufficient to inhibit the binding of bradykinon to BK-2 receptors in vitro. The amount of a compound that would be sufficient to inhibit the binding bradykinin to the BK-2 receptor may be readily determined via a BK-2 receptor binding assay, such as the assay described in Example 9. The BK-2 receptors used to determine in vitro binding may be obtained from a variety of sources, for example from preparations of rat brain or from cells expressing cloned human BK-2 receptors.

The present invention also pertains to methods for altering the signal-transducing activity of bradykinin receptors, said method comprising exposing cells expressing such receptors to an effective amount of a compound of the invention. This method includes altering the signal-transducing activity of BK-2 receptors in vivo, e.g., in a patient given an amount of a compound of formula I, or the subformulae thereof, that would be sufficient to alter the signal-transducing activity of BK-2 receptors in vitro. The amount of a compound that would be sufficient to alter the signal-transducing activity of bradykinin receptors may be determined via a bradykinin receptor signal transduction assay, such as the assay described in Example 10.

The bradykinin receptor ligands (i.e. the compounds of the invention) provided by this invention and labeled derivatives thereof are also useful as standards and reagents in determining the ability of a potential pharmaceutical to bind to the BK-2 receptor.

Isotopically-labeled compounds of this invention, which are identical to those recited in formula I, or the subformulae thereof, but for the fact that one or more atoms are replaced by an atom having an atomic mass or mass number different from the atomic mass or mass number usually found in nature, are also useful for mapping the location of bradykinin receptors (e.g., in tissue sections via autoradiography) and as radiotracers for positron emission tomography (PET) imaging, single photon emission computerized tomography (SPECT), and the like, to characterize such receptors in living subjects. Examples of isotopes that can be incorporated into compounds of the invention include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. In addition, substitution with heavy isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula Ia, or the subformulae thereof, of this invention and prodrugs thereof can generally be prepared by carrying out the procedures disclosed in the Schemes and/or in the examples below, by substituting a readily available isotopically labeled reagent for a non-isotopically labeled reagent.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques so as to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example, glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcova, et al. (*Journal of Chromatography* B 1996, 677, 1–27).

Compound half-life is inversely proportional to the frequency of dosage of a compound. In vitro half-lives of compounds may be predicted from assays of microsomal half-life as described by Kuhnz and Gieschen (*Drug Metabolism and Disposition* 1998, 26, 1120–1127).

As discussed above, preferred compounds of the invention exhibit good activity in in vitro Bradykinin receptor binding assays, especially BK-2 receptor binding assays, and specifically the assay as specified in Example 9, which follows. References herein to "in vitro BK-2 receptor binding assay" are intended to refer to that protocol as defined in Example 9 which follows.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

The disclosures of all articles and references mentioned in this application, including patents, are incorporated herein by reference.

EXAMPLES

Compounds of the invention can be prepared using the reactions depicted in Schemes 1 to 7.

Scheme 1

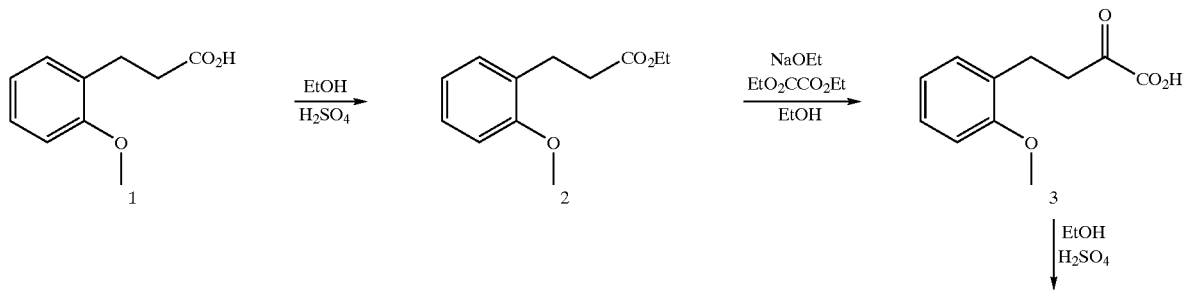

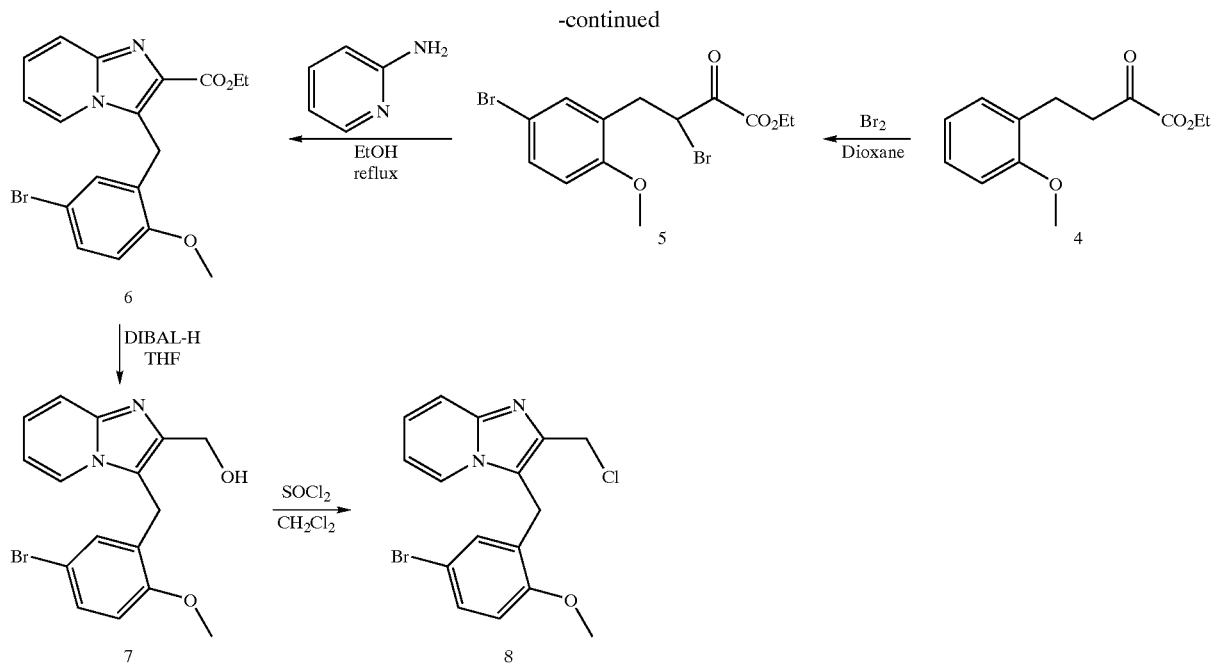

The procedure outlined in Scheme 1 is also applied to synthesize other 3-{[2-(chloromethyl)(imidazolo[1,2-a]pyridin-3-yl)methyl}-benzenes used in this invention. Depending on the substitution pattern present on the benzyl substituent and the specific conditions employed, bromination of the benzyl aromatic ring may or may not occur. It will be recognized by those with ordinary skill in the art that alternate reaction conditions can be employed to accomplish the chemical transformations outlined in Scheme 1.

Scheme 2

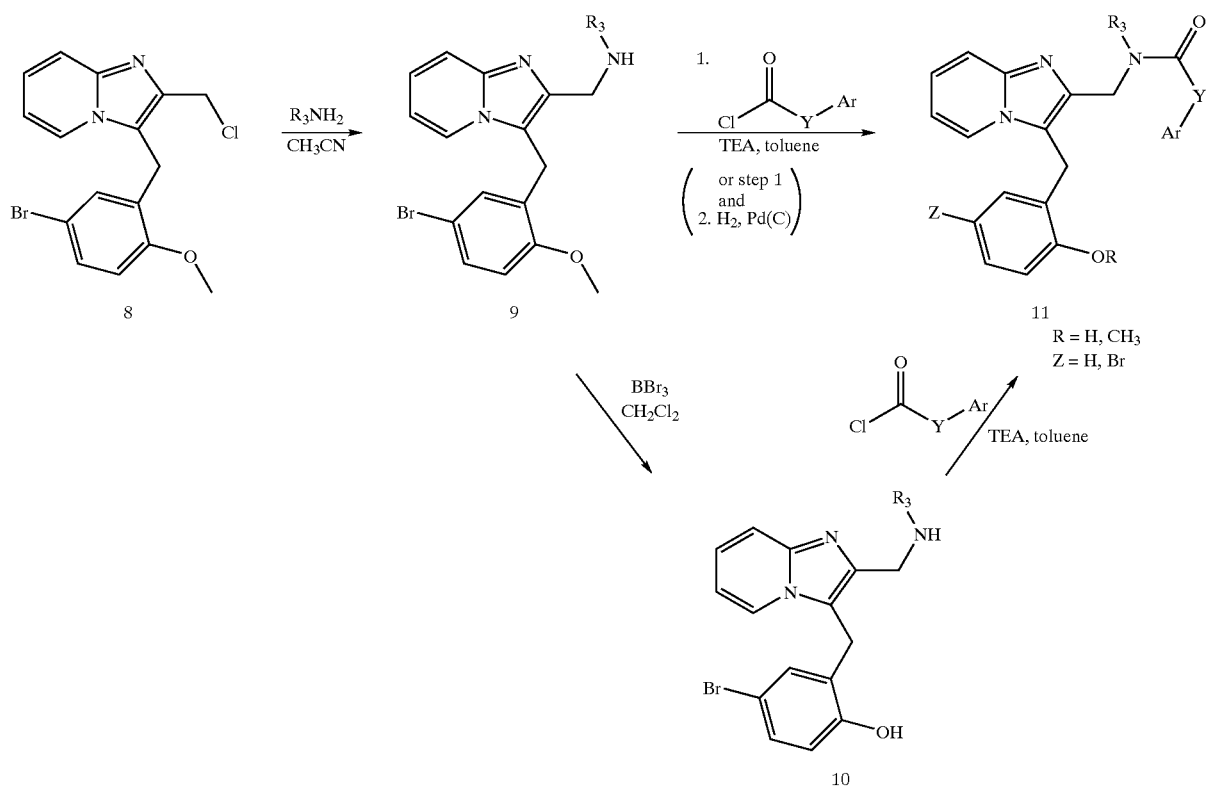

As illustrated in Scheme 2, reaction of Compound 8 with primary amines $R_3NH_2$ proceeds in various solvents including acetonitrile. In general, it is desirable to use a 5–10 fold excess of the amine to minimize formation of side products. The resulting secondary amine product 9 may be acylated with aryl or arylacetyl chlorides in the presence of base and solvent to yield the corresponding amides 11. Suitable bases for the acylation include but are not limited to triethylamine and N-methylmorpholine. Suitable solvents for the acylation reaction include but are not limited to toluene and tetrahydrofuran. Optionally, the bromo group at the 5-position of 11 may be removed by catalytic hydrogenation in the presence of a suitable catalyst such as palladium (0) on carbon and suitable solvent such as ethanol. In some instances, Compound 9 is demethylated to the 2-hydioxybenzyl derivative 10 prior to acylation. As illustrated in Scheme 2, this may be accomplished by treatment with boron tribromide in a suitable solvent such as dichloromethane. Those with ordinary skill in the art will realize that the synthetic transformations described in Scheme 2 can be accomplished using a variety of alternative procedures from the literature.

contained within the definition of $R_1$ in Formula I; $R_3$ is as defined in Formula I; L is a suitable leaving group such as bromo, iodo or mesylate. Suitable bases include but are not limited to potassium carbonate, cesium carbonate, sodium hydroxide and sodium hydride. Suitable solvents include but are not limited to N,N-dimethylformamide and tetrahydrofuran. When $R^1$ contains an ester group an additional hydrolysis step may be employed to obtain the carboxylic acid. As illustrated in Scheme 3, suitable conditions include but are not limited to treating the ester with sodium hydroxide in the presence of methanol and water. Those with ordinary skill in the art will realize that the synthetic transformations described in Scheme 3 can be accomplished using a variety of alternative procedures from the literature.

Scheme 3

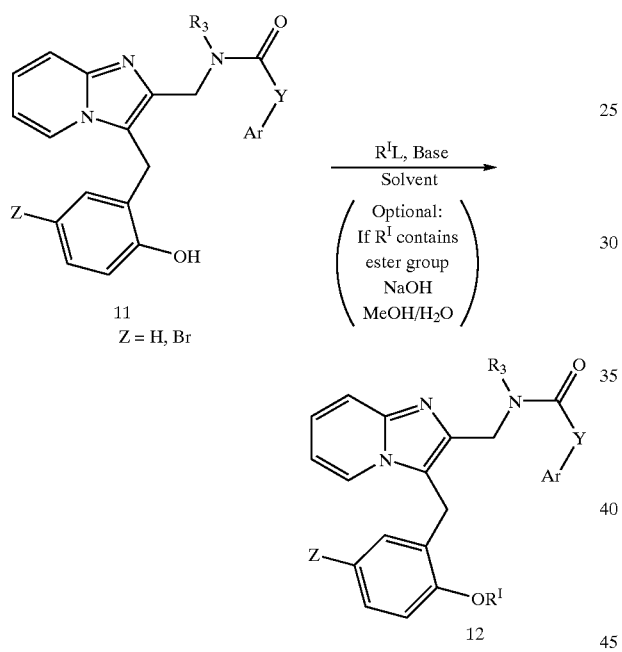

Scheme 4

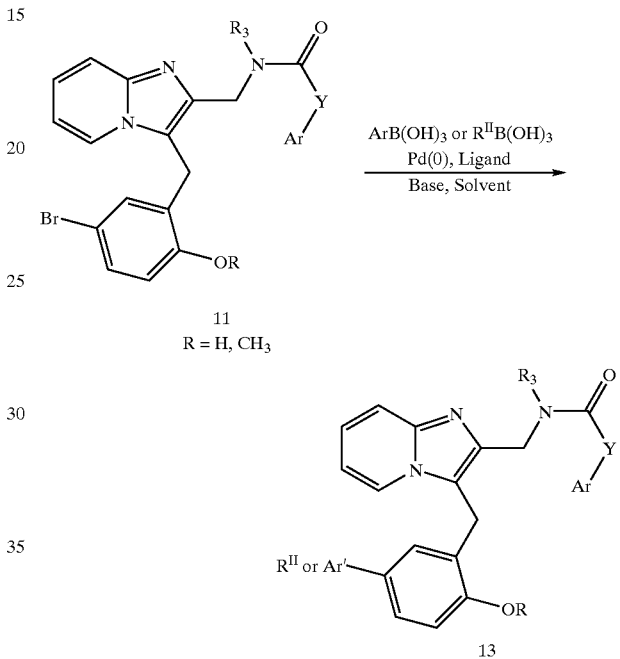

Reaction of compounds of Formula 11 with a wide variety of electrophiles such as alkyl halides, aminoalkyl halides and haloalkyl carbonyl derivatives such as ethyl bromoacetate in the presence of base and solvent affords alkylated compounds of Formula 12. In Scheme 3, $R^I$ may vary as In Scheme 4, 5-bromo-2-methoxybenzyl derivatives are reacted with various aryl and alkyl boronic acids in the presence of a suitable palladium (0) catalyst, base and solvent. Suitable conditions include but are not limited to treatment of 11 with the boronic acid in the presence of tetrakis(triphenyl-phosphine)palladium(0), potassium carbonate and toluene at 85° C. The groups Ar' and $R''$ are chosen such that they are consistent with the definition of Formula I. It will be recognized by those skilled in the art that alternate reaction conditions (e.g. palladium coupling of organotins with the bromide 11) can be employed.

Scheme 5

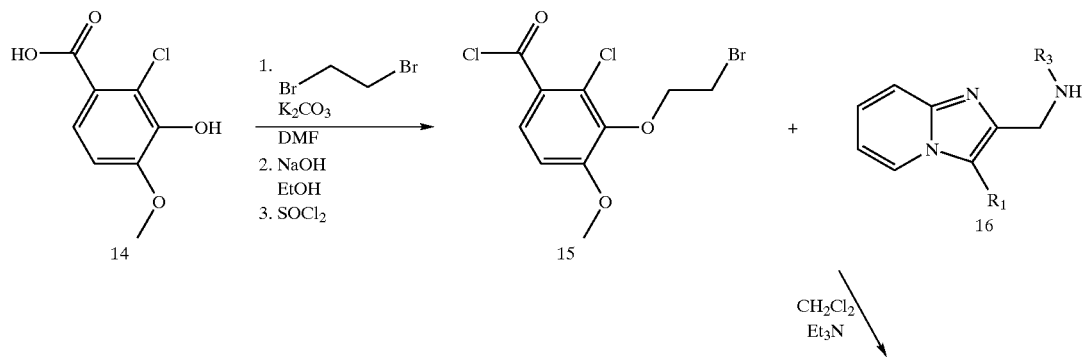

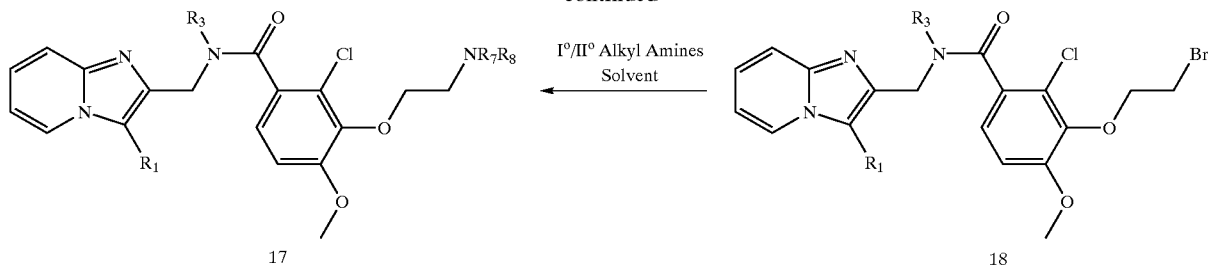

In Scheme 5, the substituents $R_1$, $R_3$, $R_7$ and $R_8$ are selected according to the definitions provided in Formula I. Compound 14, 2-chloro-3-hydroxy-4-methoxybenzoic acid, was prepared according to the procedure of Ohi et. al. in J. Antibiot. 1987, 40(1), 22–28. Suitable conditions for alkylation of 14 include but are not limited to heating with excess dibromoethane in the presence of potassium carbonate in N,N-dimethylformamide. Under these conditions, the bromoethyl ester is also formed and must be hydrolyzed by subsequent treatment with sodium hydroxide in ethanol. Suitable conditions for accomplishing each of the steps in Scheme 5 are provided in Example 6. Those skilled in the art will understand that alternate methods can be applied to accomplish each of the steps in Scheme 5.

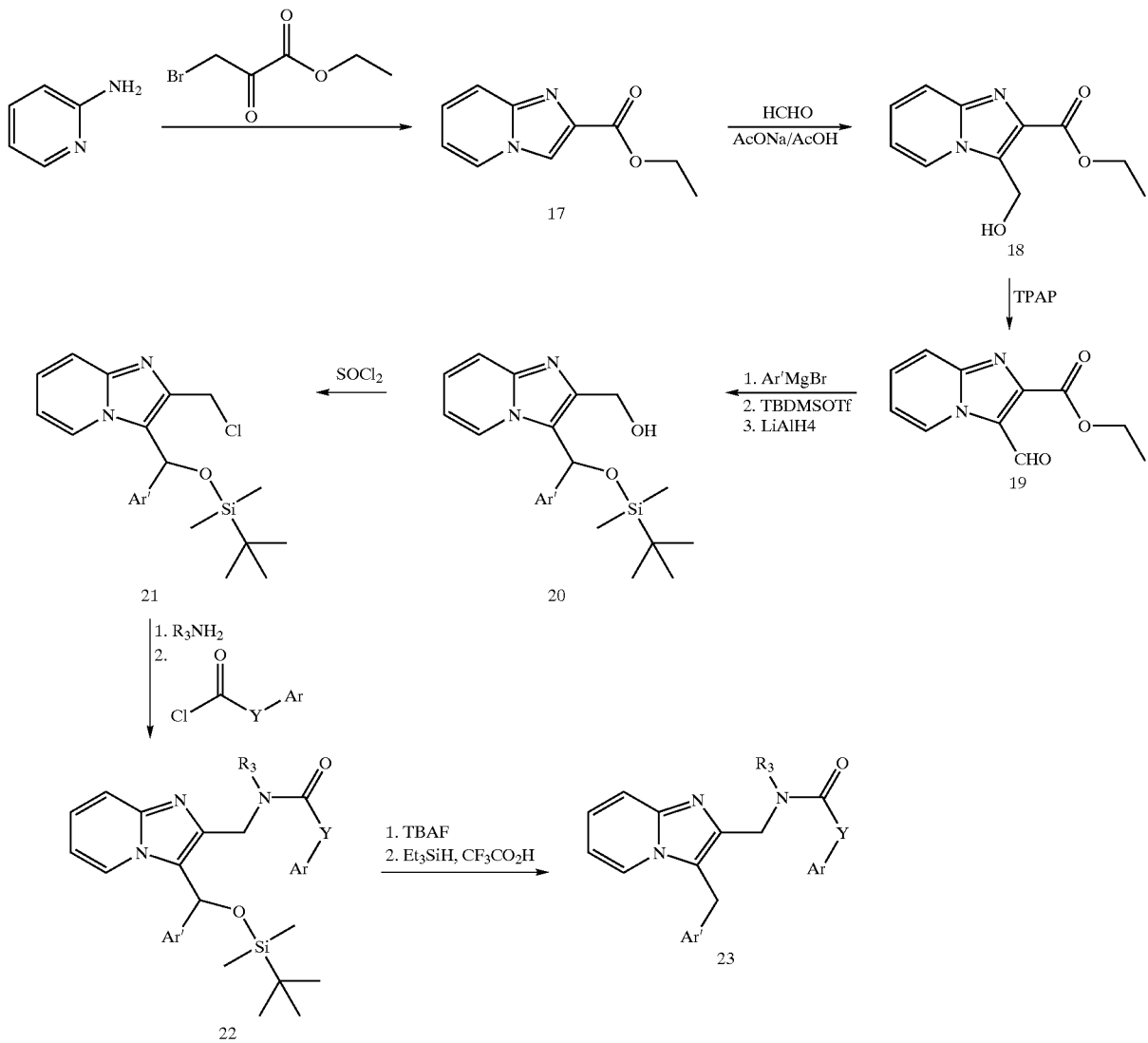

In Scheme 6, the aryl groups Ar and Ar' are selected such that the group Ar'CH$_2$ will fall within the definition of R$_1$ in Formula I and the group Ar represents an aryl ring or substituted aryl ring consistent with the definition of Formula I. Typical conditions for each transformation are provided in Example 7. It will be recognized by those skilled in the art that the alternate conditions can be employed to accomplish the synthetic transformations described in Scheme 6.

employed to produce compounds encompassed by the present invention, as demonstrated by the following examples.

The following examples illustrate the general procedures for the preparation of compounds of the invention using the reactions outlined above in Schemes 1–7. These examples are not to be construed as limiting the invention in scope or spirit to the specific procedures and compounds described in them.

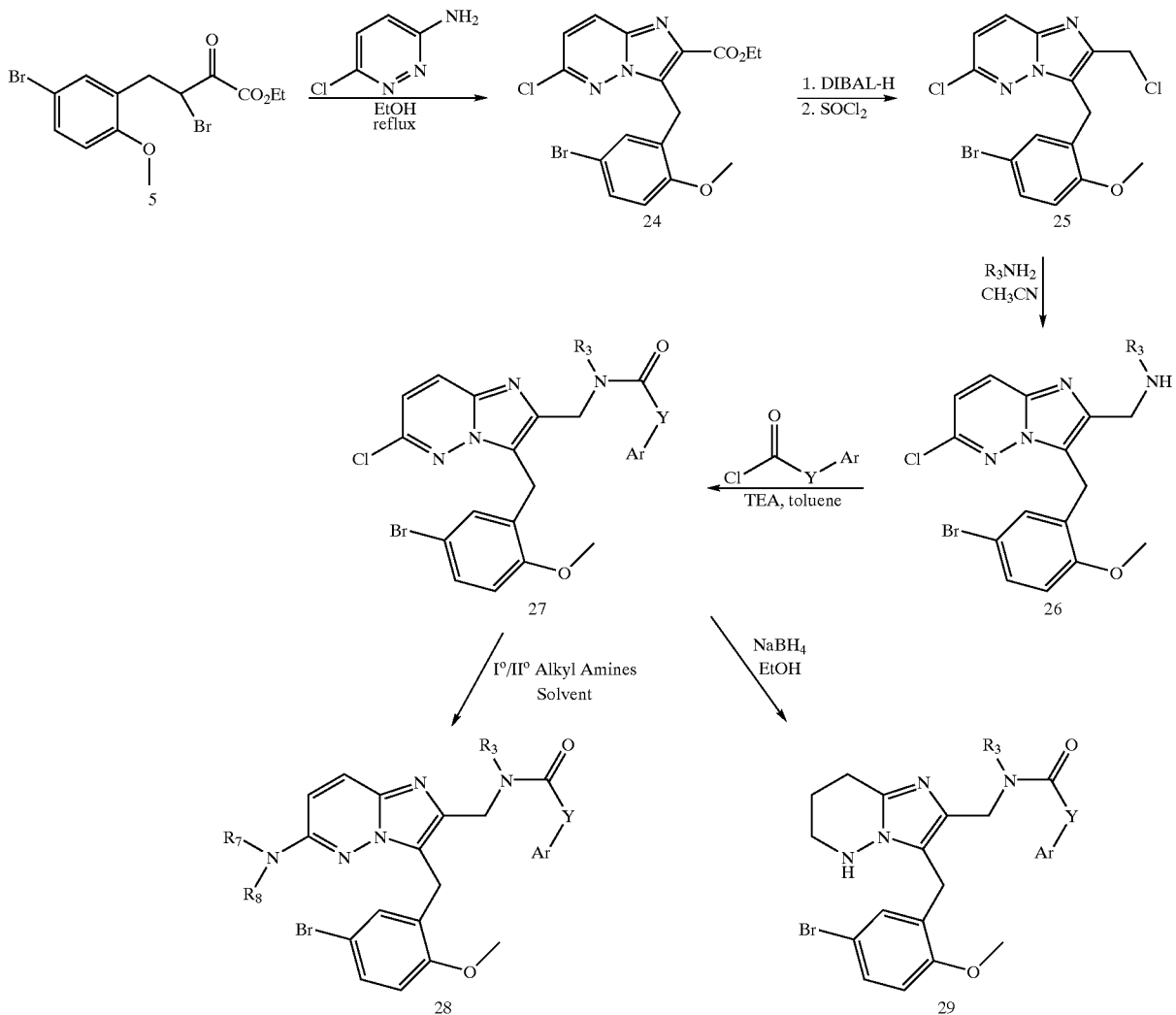

Scheme 7

In Scheme 7, R$_7$ and R$_8$ are chosen so as to be within the definition provided for R$_2$ in Formula I, the group Ar represents an aryl ring or substituted aryl ring consistent with the definition of Formula I and the groups R$_3$ and Y are as defined in Formula I. Appropriate reaction conditions for each of the transformations in Scheme 7 are given in Example 8.

It will be recognized by those skilled in the art that alternate reactions conditions may be employed to accomplish the transformations in Scheme 7.

Those having skill in the art will recognize that the starting materials may be varied and additional steps Example 1

General Procedure for the Preparation of Chloromethylimidazopyridines as Outlined in Scheme 1

A solution of 25.0 g (139.0 mmol) 3-(2-methoxyphenyl) propionic acid in 250 mL ethanol is treated at 0° C. with 5.0 mL concentrated sulfuric acid. The reaction mixture is heated to reflux for 2 hr. The reaction mixture is cooled to room temperature and volatiles removed by rotary evaporation. The residue is diluted with 250 mL dichloromethane, washed with 200 mL water, 200 mL sat. NaHCO$_3$, and 200 mL brine. The resulting organic layer is dried over anhydrous Na$_2$SO$_4$ and the solvent removed in vacuo to yield ethyl 3-(2-methoxyphenyl)propanoate, 28 g, as a tan oil.

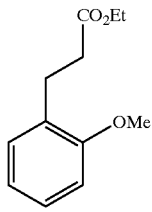

A solution of 28.0 g (135.0 mmol) of ethyl 3-(2-methoxyphenyl)propanoate in 150 mL ethyl acetate is treated with 135 mmol sodium ethoxide (freshly prepared from 3.1 g (135 mmol) sodium and 30 mL ethanol) and 39.0 g (270 mmol) diethyl oxalate. The resulting mixture is heated to reflux temperature for 1 hr and then transferred to a rotary evaporator to remove excess ethanol. The reaction solution is treated with 220 mL 15% sulfuric acid and reheated to 70 ° C. for 16 hr. The two phase mixture is cooled to 0 ° C. and separated, the organic layer is neutralized with 10% sodium hydroxide and washed with 200 mL of ethyl acetate. The resulting aqueous layer is acidified with 2M sulfuric acid and finally extracted with 3×200 mL ethyl acetate. The resulting organic layer is dried over anhydrous MgSO$_4$ and the solvent removed in vacuo to yield 18 g of a 3:2 mixture of the desired 4-(2-methoxyphenyl)-2-oxobutanoic acid and 3-(2-methoxyphenyl)propionic acid.

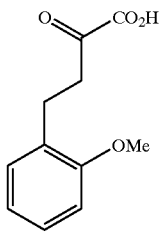

A solution of 16.0 g of the 3:2 mixture of 4-(2-methoxyphenyl)-2-oxobutanoic acid and 3-(2-methoxyphenyl)propionic acid in 250 mL ethanol is treated at 0 ° C. with 3.0 mL concentrated sulfuric acid. The reaction mixture is heated to reflux for 3 hr. The reaction mixture is cooled to room temperature and volatiles removed by rotary evaporation. The residue is diluted with 250 mL dichloromethane washed 200 mL water, 200 mL sat. NaHCO$_3$, and 200 mL brine. The resulting organic layer is dried over anhydrous MgSO$_4$ and the solvent removed in vacuo to yield 18 g of a 3:2 mixture of the desired ethyl 4-(2-methoxyphenyl)-2-oxobutanoate and ethyl 3-(2-methoxyphenyl)propanoate.

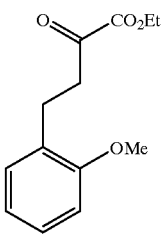

A solution of 16.0 g of the 3:2 mixture of ethyl 4-(2-methoxyphenyl)-2-oxobutanoate and ethyl 3-(2-methoxyphenyl)propanoate in 250 mL dioxane is treated with 4.2 mL (81.0 mmol) bromine. The reaction mixture is stirred at room temperature for 1 hr. The reaction mixture is diluted with 200 mL sat. NaHCO$_3$ and extracted with 3×150 mL ethyl acetate. The combined organics are washed with 200 mL sat. NaHCO$_3$, and 200 mL brine. The resulting organic layer is dried over anhydrous MgSO$_4$ and the solvent removed in vacuo to yield 20 g of a 3:2 mixture of the desired ethyl 3-bromo-4-(2-methoxy-5-bromophenyl)-2-oxobutanoate and ethyl 3-(2-methoxy-5-bromophenyl)propanoate.

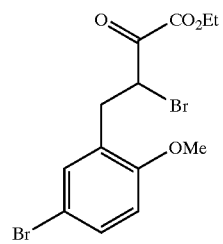

A solution of 11.94 g of the 3:2 mixture of ethyl 3-bromo-4-(2-methoxy-5-bromophenyl)-2-oxobutanoate and ethyl 3-(2-methoxy-5-bromophenyl)propanoate in 150 mL of ethanol is treated with 2.85 g (30.0 mmol) of 2-aminopyrazine and heated to reflux temperature for 16 hr. The reaction mixture is cooled to room temperature and treated with 10 g of potassium carbonate. The mixture is filtered through Celite and the solvent removed in vacuo to yield the crude material. The resulting residue is flash chromatographed with initially 1% methanol in dichloromethane and then 3% methanol in dichloromethane to afford 3.7 g (48% based on starting material) ethyl 3-[(5-bromo-2-methoxyphenyl)methyl]-imidazolo[1,2-a]pyridine-2-carboxylate.

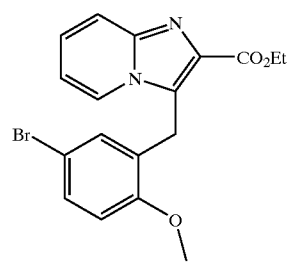

A solution of 3.69 g (9.5 mmol) of ethyl 3-[(2-methoxy-5-bromophenyl)methyl]-imidazolo[1,2-a]pyridine-2-carboxylate in 50 mL tetrahydrofuran is cooled to −78° C. and treated with 25.0 mL (25.0 mmol) of diisobutylaluminum hydride, 1M in hexane. After 1 hr the reaction is allowed to warm up to room temperature and carefully quenched by addition of 25 mL 1M sodium hydroxide. The mixture is extracted with 3×40 mL ethyl acetate and the combined extracts washed with 50 mL brine and dried over anhydrous MgSO$_4$ and the solvent removed in vacuo to afford 3.0 g (91% yield) {3-[(5-bromo-2-methoxyphenyl)methyl]-imidazolo[1,2-a]pyridin-2-yl}methan-1-ol.

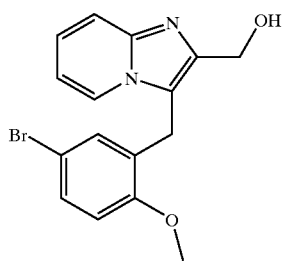

A solution of 3.0 g (8.6 mmol) of {3-[(5-bromo-2-methoxyphenyl)methyl]-imidazolo[1,2-a]pyridin-2-yl}methan-1-ol in 80 mL dichloromethane at 0° C. is treated with thionyl chloride 1.44 g (12 mmol). The resulting solution is stirred at room temperature for 1 hr and the volatiles removed by rotary evaporation. The residue is partitioned between 100 mL dichloromethane and water 100 mL. The dichloromethane extracts are dried over anhydrous MgSO₄ and the solvent removed in vacuo to give 3.1 g (98%) 4-bromo-2-{[2-(chloromethyl)(imidazolo[1,2-a]pyridin-3-yl)methyl}-1-methoxybenzene.

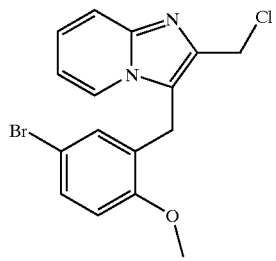

Example 2

General Procedure for the Preparation of Imidazopyridines as shown in Scheme 2

(2-chloro-3,4-Dimethoxyphenyl)-N-({3-[(5-bromo-2-hydroxyphenyl)methyl](imidazolo[1,2-a]pyridin-2-yl)}methyl)-N-(3-methylbutyl)carboxamide

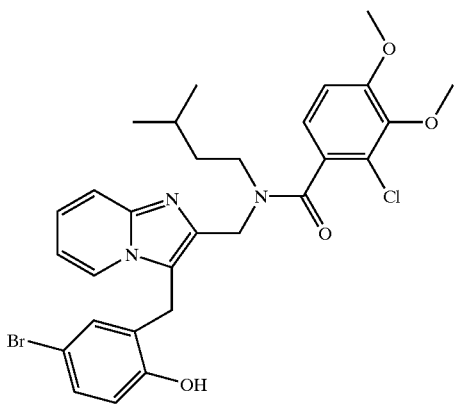

A solution of isoamyl amine 8.7 g (100 mmol) in 150 mL acetonitrile is treated with 3.0 g (8.2 mmol) 4-bromo-2-{[2-(chloromethyl)(imidazolo[1,2-a]pyridin-3-yl)methyl}-1-methoxybenzene dissolved in 10 mL acetonitrile. The resulting solution is stirred at room temperature for 4 hr and the volatiles removed by rotary evaporation. The residue is partitioned between 100 mL ethyl acetate and water 50 mL and then further extracted with 2×50 mL ethyl acetate. The ethyl acetate extracts are washed with 50 mL brine, dried over anhydrous MgSO₄ and the solvent removed in vacuo to give 3.24 g (95%) ({3-[(5-bromo-2-methoxyphenyl)methyl](imidazolo[1,2-a]pyridin-2-yl)}methyl)(3-methylbutyl)amine.

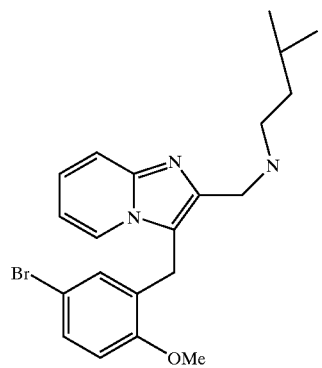

A solution of 416 mg (1.0 mmol) of ({3-[(5-bromo-2-methoxyphenyl)methyl](imidazolo[1,2-a]pyridin-2-yl)}methyl) (3-methylbutyl)amine in 20 mL dichloromethane at −78° C. is treated with boron tribromide 0.4 mL (4.0 mmol). The resulting solution is allowed to return to room temperature over 1 hr, quenched by addition of 10 mL sat. NaHCO₃ and extracted with 2×10 mL dichloromethane. The combined extract is dried over anhydrous MgSO₄ and the solvent removed in vacuo to yield 360 mg (89%) ({3-[(5-bromo-2-hydroxyphenyl)methyl](imidazolo[1,2-a]pyridin-2-yl)}methyl)(3-methylbutyl)amine.

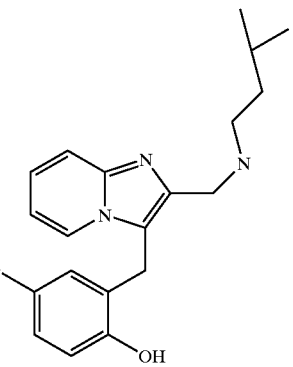

A solution of 90 mg (0.25 mmol) ({3-[(5-bromo-2-hydroxyphenyl)methyl](imidazolo[1,2-a]pyridin-2-yl)}methyl)(3-methylbutyl)amine in 4 mL dichloromethane at 0° C. is treated with triethylamine 50 mg (0.50 mmol) and then 2-chloro-3,4-dimethoxybenzoylchloride 110 mg (0.50 mmol). The solution is stirred overnight and the volatiles removed by rotary evaporation. The residue is dissolved in 4 mL methanol and treated with 2 mL 1M sodium hydroxide. The solution is heated to 45° C. for 1 hr and the volatiles removed by rotary evaporation. The mixture is acidified with 1M hydrochloric acid, extracted with 3×5 mL ethyl acetate and the combined extracts washed with 5 mL brine. The combined extract is dried over anhydrous MgSO₄ and the solvent removed in vacuo to yield 120 mg (80%) N-({3-[(5-bromo-2-hydroxyphenyl)methyl](imidazolo[1,2-a]pyridin-2-yl)}methyl)(2-chloro-3,4-dimethoxyphenyl)-N-(3-methylbutyl)carboxamide. Mass Spec m/z (M⁺+1) 602.

Example 3

General Procedure for the Alkylation of Phenol Derivatives as shown in Scheme 3

Ethyl 2-{4-bromo-2-[(2-{[(2-chloro-3,4-dimethoxyphenyl)-N-(3-methylbutyl)carbonylamino]methyl}(imidazolo [1,2-a]pyridin-3-yl))methyl]phenoxy}acetate

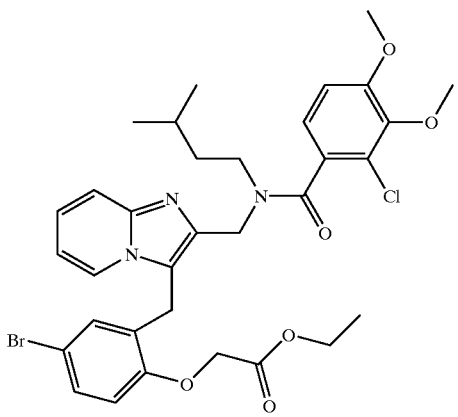

A solution of 300 mg (0.5 mmol) N-({3-[(5-bromo-2-hydoxyphenyl)methyl](imidazolo[1,2-a]pyridin-2-yl)}methyl)(2-chloro-3,4-dimethoxyphenyl)-N-(3-methylbutyl)carboxamide in 3 mL N,N-dimethylformamide is treated with 207 mg (1.5 mmol) anhydrous potassium carbonate and 167 mg (1.0 mmol) ethyl bromoacetate. The solution is stirred for 1 hr and partitioned between 50 mL ethyl acetate and 50 mL water. The organic layer is washed with 3×50 mL water, 50 mL brine, dried over anhydrous MgSO$_4$ and the solvent removed in vacuo to yield 268 mg (78%) Ethyl 2-{4-bromo-2-[(2-{[(2-chloro-3,4-dimethoxyphenyl)-N-(3-methylbutyl)carbonylamino]methyl}(imidazolof1,2-a]pyridin-3-yl))methyl]phenoxy}acetate. Mass Spec m/z (M$^+$+1) 688.

Example 4

General Procedure for the Preparation of Carboxylic Acid Derivatives as shown in Scheme 3

2-{4-bromo-2-[(2-{[(2-chloro-3,4-Dimethoxyphenyl)-N-(3-methylbutyl)carbonylamino]methyl}(imidazolo[1,2-a]pyridin-3-yl))methyl]phenoxy}acetic Acid

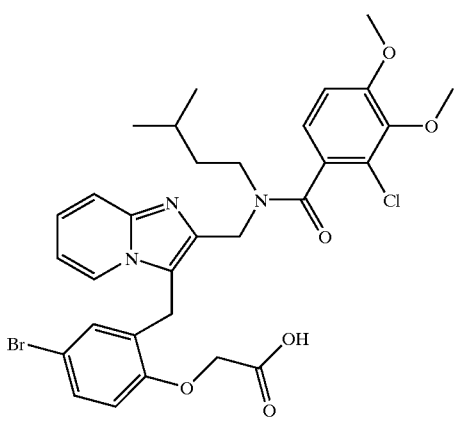

A solution of 240 mg (0.35 mmol) ethyl 2-{4-bromo-2-[(2-{[(2-chloro-3,4-dimethoxyphenyl)-N-(3-methylbutyl)carbonylamino]methyl}(imidazolo[1,2-a]pyridin-3-yl))methyl]phenoxy}acetate in 4 mL methanol is treated with 55 mg (1.3 mmol) sodium hydroxide. The solution is stirred at room temperature for 3 hr and the solvent removed in vacuo. The residue is redissolved in 5 mL dichloromethane and acidified with 1M hydrochloric acid in ether. The solvent is removed in vacuo and 5 mL dichloromethane is added. The solution is filtered through Celite and the filtrate treated with excess IM hydrochloric acid in ether. The solvent is removed in vacuo and the residue triturated with ether to give 133 mg (58%) 2-{4-bromo-2-[(2-{[(2-chloro-3,4-dimethoxyphenyl)-N-(3-methylbutyl)carbonylamino]methyl}(imidazolo[1,2-a]pyridin-3-yl))methyl]phenoxy}acetic acid mono hydrochloride. Mass Spec m/z (M$^+$+1) 658.

Example 5

General Procedure for Preparation of Derivatives by Palladium Coupling as Shown in Scheme 4

(2-chloro-3,4-Dimethoxyphenyl)-N-({3-[(2-methoxy-5-(3-pyridyl)phenyl)methyl](imidazolo[1,2-a]pyridin-2-yl)}methyl)-N-(3-methylbutyl)carboxamide

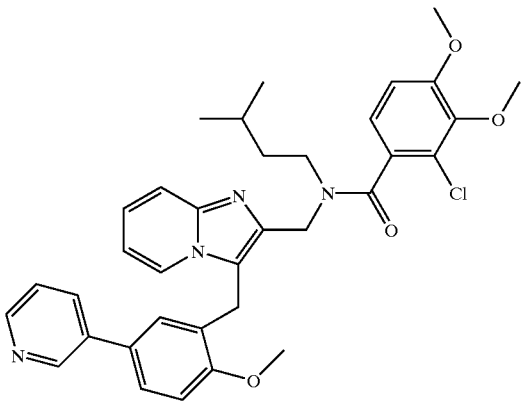

A solution of 61 mg (0.1 mmol) N-({3-[(5-bromo-2-methoxyphenyl)methyl](imidazolo[1,2-a]pyridin-2-yl)}methyl)(2-chloro-3,4-dimethoxyphenyl)-N-(3-methylbutyl)carboxamide in 2 mL toluene is treated with 4 mg (0.003 mmol) tetrakis(triphenylphosphine)palladium(0), 15 mg (0.12 mmol) pyridine-3-boronic acid and 0.2 mL 2M potassium carbonate. The solution is heated to 85° C. for 18 hr and cooled to room temperature. The solution is diluted with 10 mL dichloromethane, washed with 10 mL brine, dried over anhydrous MgSO$_4$ and the solvent removed in vacuo to give the crude residue. The residue is prep-plate chromatographed (9% MeOH/CH$_2$Cl$_2$/0.5% NH$_4$OH) to afford 55 mg (89%) (2-chloro-3,4-dimethoxyphenyl)-N-({3-[(2-methoxy-5-(3-pyridyl)phenyl)methyl](imidazol[1,2-a]pyridin-2-yl)}methyl)-N-(3-methylbutyl)carboxamide. Mass Spec m/z (M$^+$+1) 613.

Using the above procedures, the following compounds shown in Table 1 were also prepared according to Schemes 1,2 and 3.

| Compound | Name and Physical Data | Structure |
|---|---|---|
| 5a | N-({3-[(5-bromo-2-methoxyphenyl)methyl](imidazolo[1,2-a]pyridin-2-yl)}methyl)(2-chloro-3,4-dimethoxyphenyl)-N-(3-methylbutyl)carboxamide.<br>Mass Spec m/z (M$^+$ + 1) 614. | 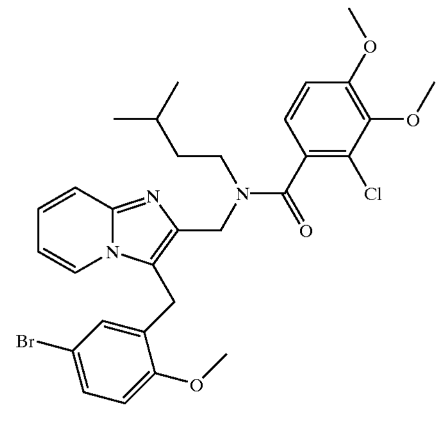 |
| 5b | (N-({3-[(5-bromo-2-methoxyphenyl)methyl](imidazolo[1,2-a]pyridin-2-yl)}methyl)(2-chloro-3,4-dimethoxyphenyl)-(n-pentyl)carboxamide.<br>Mass Spec m/z (M$^+$ + 1) 614. | 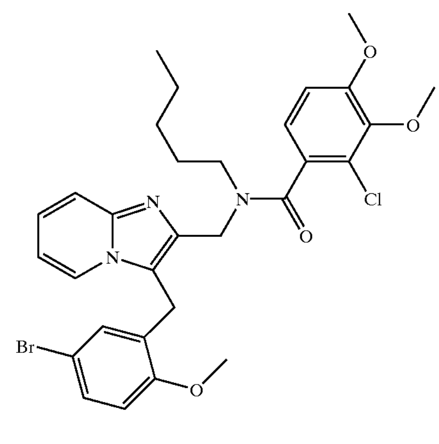 |
| 5c | N-({3-[(2-methoxy-5-(3-thienyl)phenyl)methyl](imidazolo[1,2-a]pyridin-2-yl)}methyl)(2-chloro-3,4-dimethoxyphenyl)-N-(3-methylbutyl)carboxamide.<br>Mass Spec m/z (M$^+$ + 1) 618. | 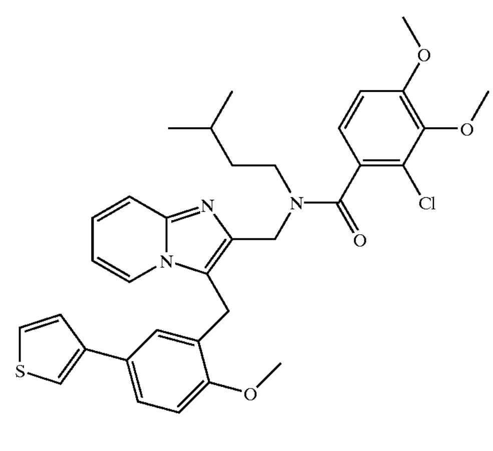 |

| Compound | Name and Physical Data | Structure |
|---|---|---|
| 5d | (N-({3-[(2-methoxy-5-(3-aminophenyl)phenyl)methyl](imidazolo[1,2-a]pyridin-2-yl)}methyl)(2-chloro-3,4-dimethoxyphenyl)-N-(3-methylbutyl)carboxamide.<br>Mass Spec m/z (M$^+$ + 1) 627. | 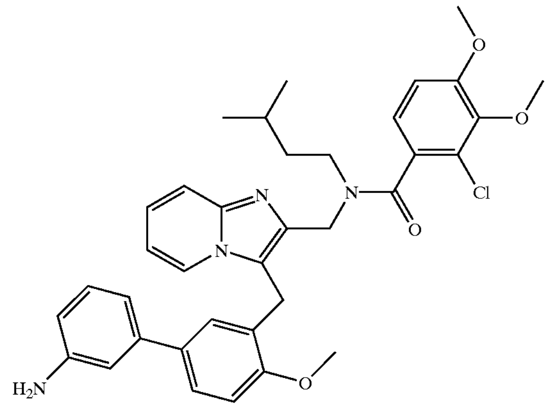 |
| 5e | N-({3-[(2-methoxy-5-(2-methoxyphenyl)phenyl)methyl](imidazolo[1,2-a]pyridin-2-yl)}methyl)(2-chloro-3,4-dimethoxyphenyl)-N-(3-methylbutyl)carboxamide.<br>Mass Spec m/z (M$^+$ + 1) 642. | 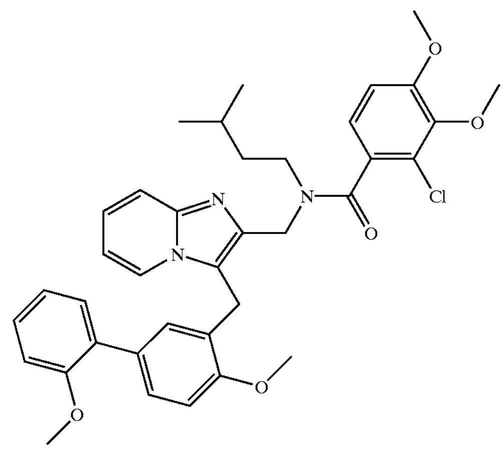 |
| 5f | N-({3-[(2-methoxy-5-(3-methoxyphenyl)phenyl)methyl](imidazolo[1,2-a]pyridin-2-yl)}methyl)(2-chloro-3,4-dimethoxyphenyl)-N-(3-methylbutyl)carboxamide.<br>Mass Spec m/z (M$^+$ + 1) 642. | 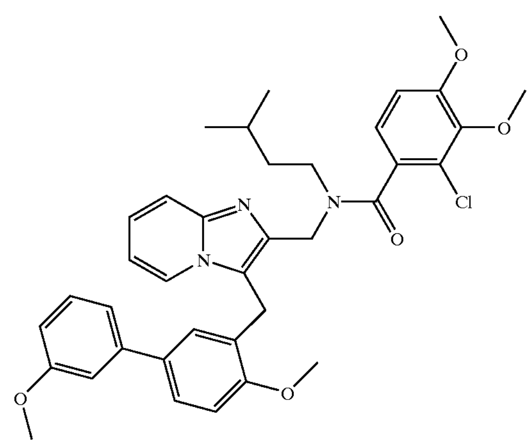 |

| Compound | Name and Physical Data | Structure |
|---|---|---|
| 5g | N-({3-[(2-methoxy-5-(4-methoxyphenyl)phenyl) methyl](3a-hydroimidazolo[1,2-a]pyridin-2-yl)}methyl) (2-chloro-3,4-dimethoxyphenyl)-N-(3-methylbutyl)carboxamide. Mass Spec m/z (M$^+$ + 1) 642. | 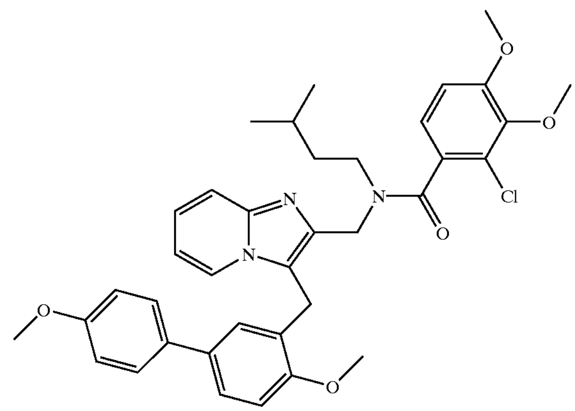 |
| 5h | N-({3-[(2-methoxy-5-(2-naphthyl)phenyl) methyl](imidazolo[1,2-a]pyridin-2-yl)}methyl) (2-chloro-3,4-dimethoxyphenyl)-N-(3-methylbutyl)carboxamide Mass Spec m/z (M$^+$ + 1) 662. | 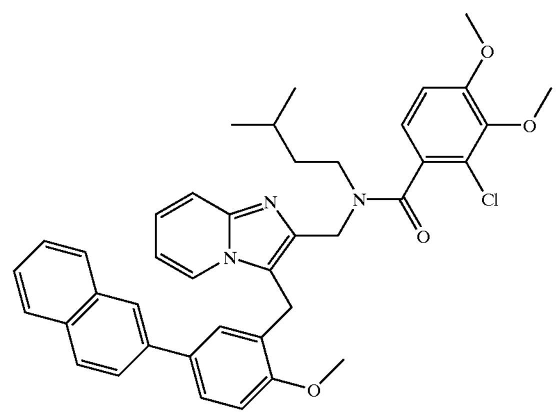 |
| 5i | N-({3-[(5-(n-butyl)-2-methoxyphenyl) methyl](imidazolo[1,2-a]pyridin-2-yl)}methyl) (2-chloro-3,4-dimethoxyphenyl)-N-(3-methylbutyl)carboxamide Mass Spec m/z (M$^+$ + 1) 592 | 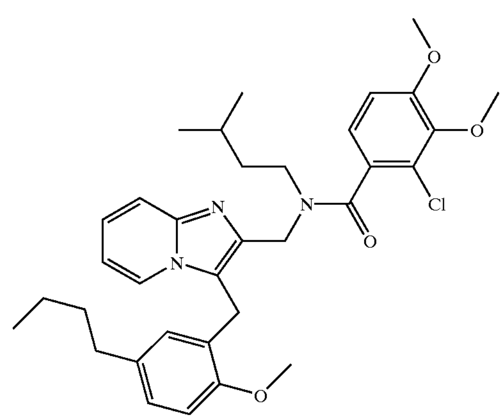 |

-continued

| Compound | Name and Physical Data | Structure |
|---|---|---|
| 5j | N-({3-[(5-bromo-2-methoxyphenyl)methyl](imidazolo[1,2-a]pyridin-2-yl)}methyl)(2-chloro-4-isopropoxyphenyl)-N-(3-methylbutyl)carboxamide<br>Mass Spec m/z (M$^+$ + 1) 612 | 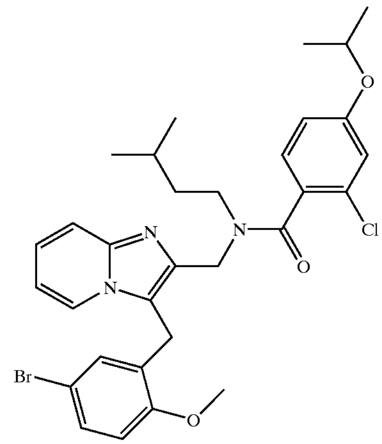 |
| 5k | N-({3-[(5-bromo-2-hydroxyphenyl)methyl](imidazolo[1,2-a]pyridin-2-yl)}methyl)(2-chloro-4-isopropoxyphenyl)-N-(3-methylbutyl)carboxamide<br>Mass Spec m/z (M$^+$ + 1) 598 | 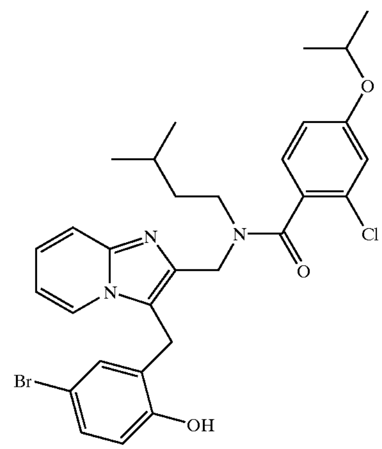 |
| 5l | Ethyl 2-{4-bromo-2-[(2-{[(2-chloro-4-isopropoxyphenyl)-N-(3-methylbutyl)carbonylamino]methyl}(imidazolo[1,2-a]pyridin-3-yl))methyl]phenoxy}acetate<br>Mass Spec m/z (M$^+$ + 1) 684 | 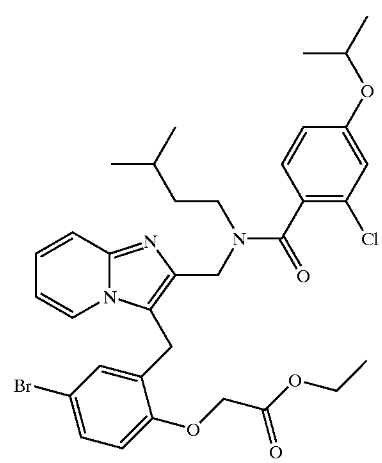 |

-continued

| Compound | Name and Physical Data | Structure |
|---|---|---|
| 5m | 2-{4-bromo-2-[(2-{[(2-chloro-4-isopropoxyphenyl)-N-(3-methylbutyl)carbonylamino]methyl}(imidazolol[1,2-a]pyridin-3-yl))methyl]phenoxy}acetic acid<br>Mass Spec m/z (M$^+$ + 1) 656 | 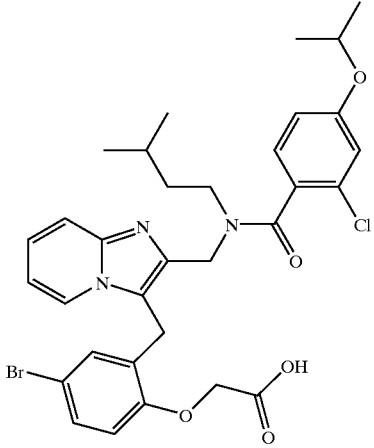 |
| 5n | N-({3-[(2-methoxy-5-(3-thienyl)phenyl](imidazolo[1,2-a]pyridin-2-yl)}methyl)(2-chloro-4-isopropoxyphenyl)-N-(3-methylbutyl)carboxamide<br>Mass Spec m/z (M$^+$ + 1) 616 | 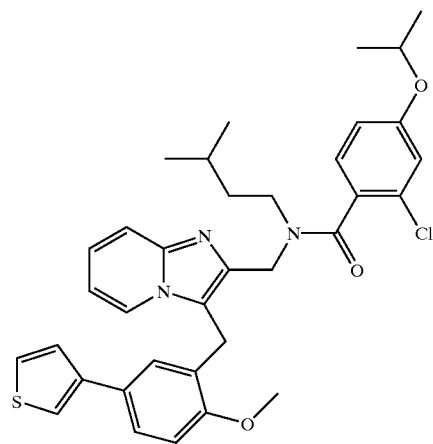 |
| 5o | N-({3-[(2-hydroxy-5-(3-thienyl)phenyl](imidazolo[1,2-a]pyridin-2-yl)}methyl)(2-chloro-4-isopropoxyphenyl)-N-(3-methylbutyl)carboxamide<br>Mass Spec m/z (M$^+$ + 1) 602 | 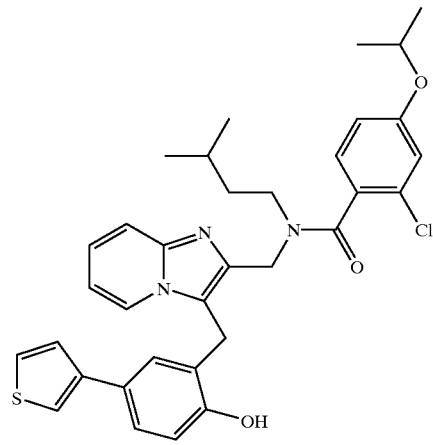 |

-continued

| Compound | Name and Physical Data | Structure |
|---|---|---|
| 5p | Ethyl 2-{4-(3-thienyl)-2-[(2-{[(2-chloro-4-isopropoxyphenyl)-N-(3-methylbutyl)carbonylamino]methyl}(imidazolo[1,2-a]pyridin-3-yl))methyl]phenoxy}acetate<br>Mass Spec m/z (M+ + 1) 688 | 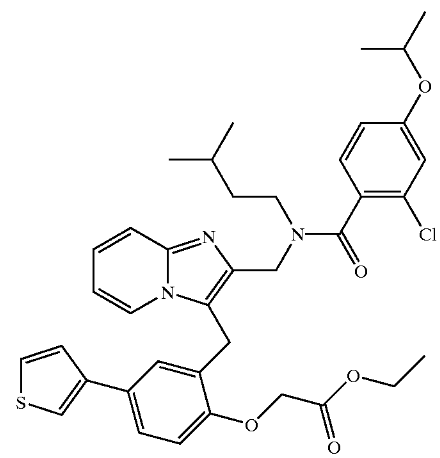 |
| 5q | 2-{4-(3-thienyl)-2-[(2-{[(2-chloro-4-isopropoxyphenyl)-N-(3-methylbutyl)carbonylamino]methyl}(imidazolo[1,2-a]pyridin-3-yl))methyl]phenoxy}acetic acid<br>Mass Spec m/z (M+ + 1) 660 | 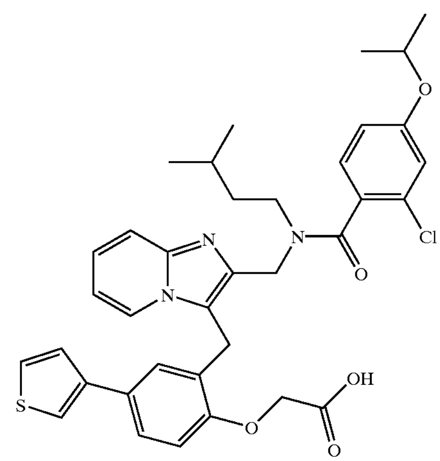 |
| 5r | N-({3-[(2-methoxyphenyl)methyl](imidazolo[1,2-a]pyridin-2-yl)}methyl)(2-chloro-3,4-dimethoxyphenyl)-N-(3-methylbutyl)carboxamide<br>Mass Spec m/z (M+ + 1) 536 | 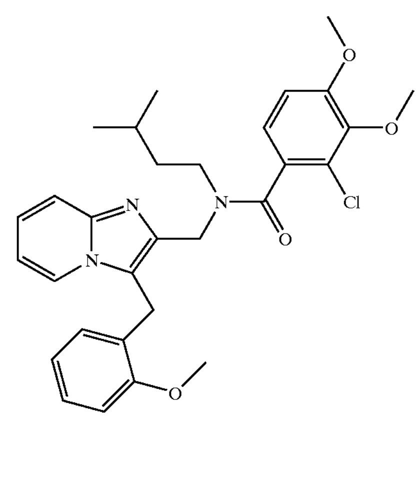 |

| Compound | Name and Physical Data | Structure |
|---|---|---|
| 5s | N-({3-[(2-chlorophenyl)methyl](imidazolo[1,2-a]pyridin-2-yl)}methyl)(2-chloro-3,4-dimethoxyphenyl)-N-(3-methylbutyl)carboxamide<br>Mass Spec m/z (M⁺ + 1) 540 | 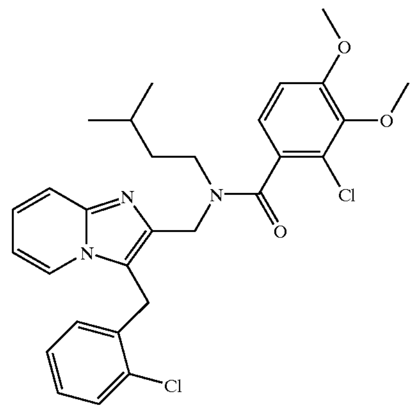 |
| 5t | N-({3-(benzyl)(imidazolo[1,2-a]pyridin-2-yl)}methyl)(2-chloro-3,4-dimethoxyphenyl)-N-(3-methylbutyl)carboxamide<br>Mass Spec m/z (M⁺ + 1) 506 | 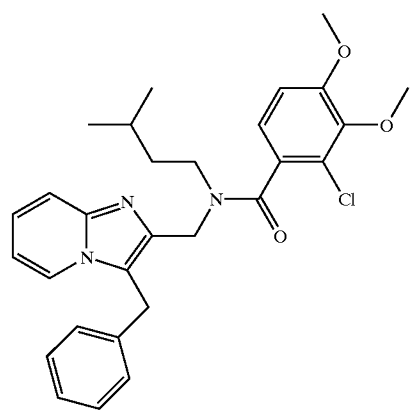 |

Example 6

General Procedure for the Preparation of Aminoalkoxy Derivatives as shown in Scheme 5

(2-chloro4-Methoxy-3-(2-cyclopentylaminoethoxy)phenyl)-N-({3-[(2-methoxyphenyl)methyl](imidazolo[1,2-a]pyridin-2-yl)}methyl)-N-(3-methylbutyl)carboxamide

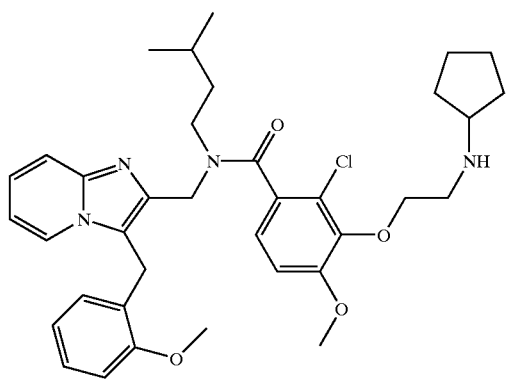

A mixture of 2-chloro-3-hydroxy-4-methoxybenzoic acid (9.00 g, 44.4 mmol), dibromoethane (25 g, 133 mmol) and potassium carbonate (12.5 g, 89.0 mmol) in N,N-dimethylformamide (400 ml) is heated at 65 °C. for 1 h. The reaction mixture is cooled to ambient temperature, diluted with 200 ml of dichloromethane and washed three times with 100 ml of 1 M aqueous hydrochloric acid. The resulting organic solution is dried over anhydrous sodium sulfate and evaporated to obtain 14.1 g (79%) of bromoethyl 2-chloro-3-bromoethoxy-4-methoxybenzoate.

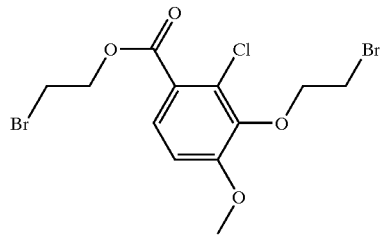

To a suspension of bromoethyl 2-chloro-3-bromoethoxy-4-methoxybenzoate (2.0 g, 4.8 mmol) in ethanol (6 ml) is added 2.5 N aqueous sodium hydroxide (4.8 ml, 12 mmol). The resulting mixture is heated at 50° C. until dissolved plus an additional 10 minutes. The solution is cooled, acidified with 3 N HCl, transferred to a separatory funnel and extracted with ethyl acetate (4×25 ml). The combined organic layers are washed with brine (25 ml), dried over magnesium sulfate and evaporated to obtain 1.4 g (93%) of 3-bromoethoxy-2-chloro-4-methoxybenzoic acid.

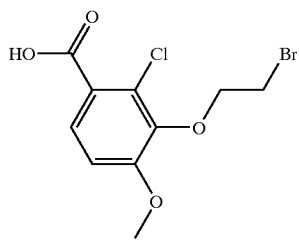

A suspension of 3-bromoethoxy-2-chloro-4-methoxybenzoic acid (1.4 g, 4.5 mmol) in thionyl chloride (20 ml) is heated at 60 °C. until dissolved (~20 min) plus an additional 30 minutes. The reaction mixture is cooled to room temperature and excess thionyl chloride is evaporated under reduced pressure. The resulting residue is evaporated at reduced pressure with toluene (50 ml) two times to obtain 1.5 g (100%) of 2-chloro-3-bromoethoxy-4-methoxybenzoic acid chloride.

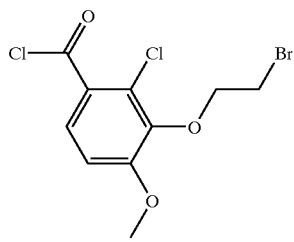

To a solution of ({3-[(2-methoxyphenyl)methyl](imidazolo[1,2-a]pyridin-2-yl)}methyl) (3-methylbutyl)amine (1.4 g, 4.2 mmol) in dichloromethane (15 ml) is added triethylamine (0.7 ml, 5 mmol) followed by 2-chloro-3-bromoethoxy-4-methoxybenzoic acid chloride (1.5 g, 4.5 mmol). The reaction mixture is stirred at ambient temperature for 65 h. Aqueous 1 N sodium hydroxide (20 ml) is added and the resulting mixture is extracted with dichloromethane (3×20 ml). The combined organic layers are dried over magnesium sulfate, filtered, and evaporated at reduced pressure. Chromatography on silica gel with ethyl acetate provides 1.7 g (65%) of (2-chloro-3-bromoethoxy-4-methoxyphenyl)-N-({3-[(2-methoxyphenyl)methyl](imidazolo[1,2-a]pyridin-2-yl)} methyl)-N-(3- methylbutyl)carboxamide.

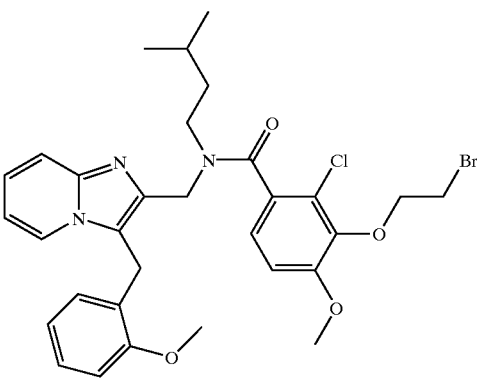

To 0.1 ml of a 0.2 M solution of (2-chloro-3-bromoethoxy-4-methoxyphenyl)-N-({3-[(2-methoxyphenyl)methyl](imidazolo[1,2-a]pyridin-2-yl)}methyl)-N-(3-methylbutyl)carboxamide in N-methylpyrrolidinone is added 0.1 ml of a 1 M solution of cyclopentylamine. The mixture is heated at 90 °C. for 15 h in a sealed vial. After cooling to room temperature, the reaction mixture is diluted with 0.5 ml of ethyl acetate and washed with 0.5 ml of 1 N aqueous sodium hydroxide. The organic layer is separated and purified by preparative TLC eluting with 9/1/0.5 ethyl acetate/methanol/triethylamine to obtain 11 mg of the title compound. Mass Spec m/z (M$^+$+1) 633.

Using the above procedures, the compounds shown in TABLE II were also prepared according to Scheme 5.

| Compound | Name and Physical Data | Structure |
|---|---|---|
| 6a | N-({3-[(5-bromo-2-methoxyphenyl)methyl](imidazolo[1,2-a]pyridin-2-yl)}methyl)(2-chloro-4-methoxy-3-(2-pyrrolidinylethoxy)phenyl)-N-(3-methylbutyl)carboxamide<br>Mass Spec m/z (M$^+$ + 1) 697 | 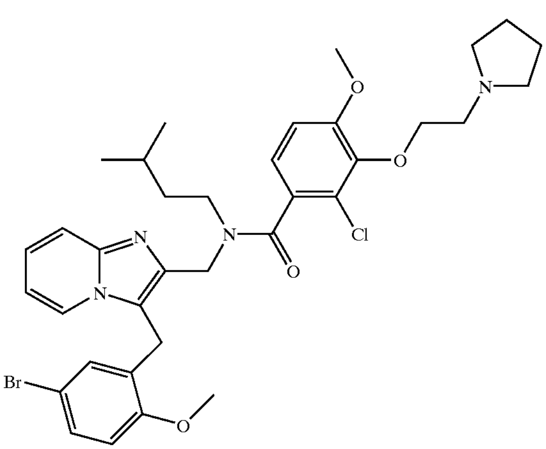 |

-continued

| Compound | Name and Physical Data | Structure |
|---|---|---|
| 6b | N-({3-[(5-bromo-2-methoxyphenyl)methyl](imidazolo[1,2-a]pyridin-2-yl)}methyl)(2-chloro-4-methoxy-3-(2-piperidinylethoxy)phenyl)-N-(3-methylbutyl)carboxamide<br>Mass Spec m/z (M$^+$ + 1) 711 | 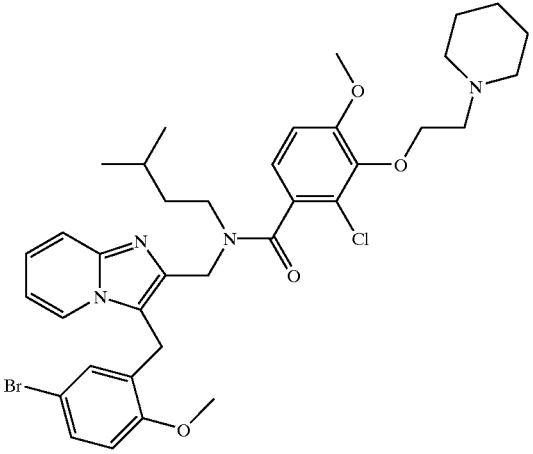 |
| 6c | N-({3-[(5-bromo-2-methoxyphenyl)methyl](imidazolo[1,2-a]pyridin-2-yl)}methyl)(2-chloro-4-methoxy-3-(2-morpholinoethoxy)phenyl)-N-(3-methylbutyl)carboxamide<br>Mass Spec m/z (M$^+$ + 1) 713. | 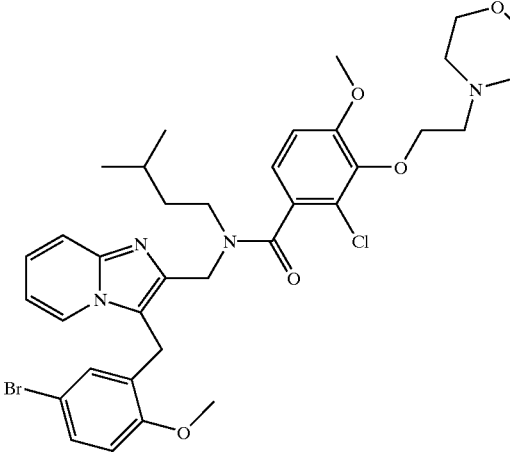 |
| 6d | N-({3-[(5-bromo-2-methoxyphenyl)methyl](imidazolo[1,2-a]pyridin-2-yl)}methyl)(2-chloro-4-methoxy-3-(2-thiomorpholinoethoxy)phenyl)-N-(3-methylbutyl)carboxamide<br>Mass Spec m/z (M$^+$ + 1) 729 | 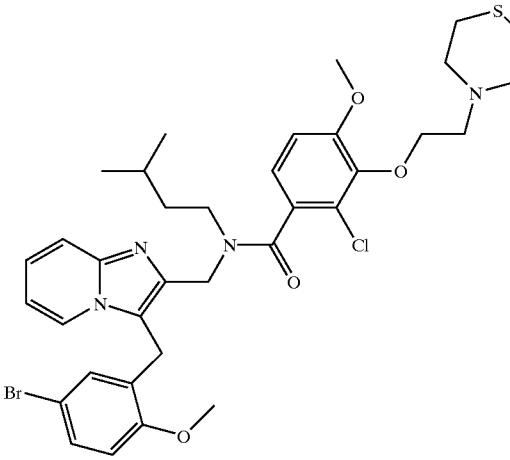 |

| Compound | Name and Physical Data | Structure |
|---|---|---|
| 6e | N-({3-[(5-bromo-2-methoxyphenyl)methyl](imidazolo[1,2-a]pyridin-2-yl)}methyl)(2-chloro-4-methoxy-3-[2-(n-butylamino)ethoxy]phenyl)-N-(3-methylbutyl)carboxamide<br>Mass Spec m/z (M$^+$ + 1) 699 | 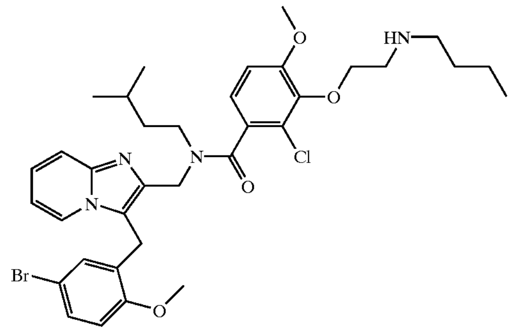 |
| 6f | N-({3-[(5-bromo-2-methoxyphenyl)methyl](imidazolo[1,2-a]pyridin-2-yl)}methyl)(2-chloro-4-methoxy-3-[2-(2-methylpropylamino)ethoxy]phenyl)-N-(3-methylbutyl)carboxamide<br>Mass Spec m/z (M$^+$ + 1) 699 | 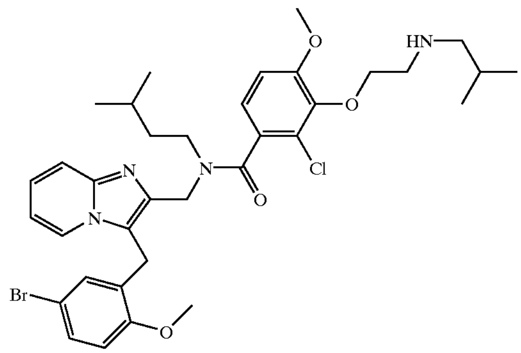 |

Example 7

General Procedure for the Preparation of Imidazopyridines as shown in Scheme 6

(2-chloro-3,4-Dimethoxyphenyl)-N-({3-[(2,5-dimethoxyphenyl)methyl](imidazolo[1,2-a]pyridin-2-yl)}methyl)-N-(3-methylbutyl)carboxamide

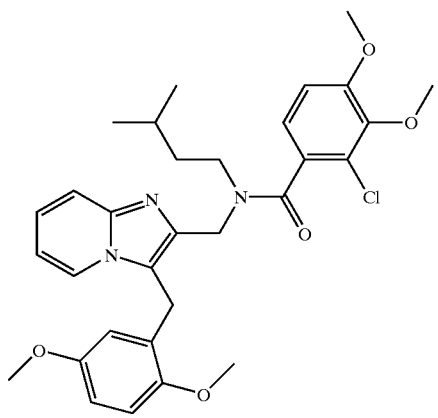

A solution of 7.8 g (40 mmol) of ethyl bromopyruvate in 40 mL of ethanol is treated with 3.76 g (30.0 mmol) of 2-aminopyrazine and heated to reflux temperature for 16 hr. The reaction mixture is cooled to room temperature and treated with 10 g of potassium carbonate. The mixture is filtered through Celite and the solvent removed in vacuo to yield the crude material. The resulting residue is flash chromatographed with initially 1% methanol in dichloromethane to afford 3.5 g (46%) ethyl imidazolo[1,2-a]pyridine-2-carboxylate.

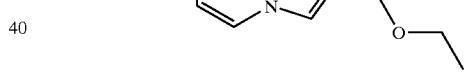

A mixture of 570 mg (3.0 mmol) ethyl imidazolo[1,2-a]pyridine-2-carboxylate, glacial acetic acid (0.8 mL) and 1 g (12 mmol) sodium acetate is treated with 6 mL 37% formaldehyde in water. The mixture is heated in a sealed tube at 90° C. for 6 hr and the acetic acid removed in vacuo. The residue is made basic by addition of 2M sodium hydroxide and extracted into 3×10 mL dichloromethane containing 1% methanol. The organic extract is dried over anhydrous MgSO$_4$ and the solvent removed in vacuo to give the crude residue. The residue is flash chromatographed with initially 10% methanol in dichloromethane to afford 325 mg (49%) ethyl 3-(hydroxymethyl)-imidazolo[1,2-a]pyridine-2-carboxylate.

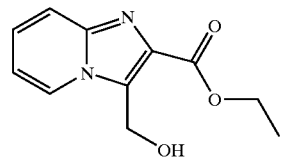

A solution of 1.2 g (5.45 mmol) of ethyl 3-(hydroxymethyl)-imidazolo[1,2-a]pyridine-2-carboxylate in 50 mL dichloromethane is treated with 1.75 g (15.0 mmol) of N-methylmorpholine N-oxide, 2.5 g powdered 4A molecular sieves and 180 mg (0.5 mmol) tetrapropylammonium perruthenate. The mixture is stirred at room temperature for 2 hr and applied directly to a column of silica. The column is eluted with 10% methanol in dichloromethane to afford 1.09 g (92%) ethyl 3-formyl-imidazolo[1,2-a] pyridine-2-carboxylate.

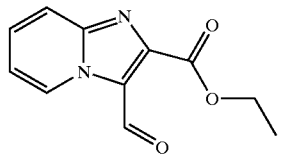

A solution of 872 mg (4.0 mmol) of ethyl 3-formyl-imidazolo[1,2-a]pyridine-2-carboxylate in 40 mL THF is treated at −50° C. with 4 mL (4.0 mmol) 1M 2,5-dimethoxyphenylmagnesium bromide in THF. The temperature is allowed to reach −10° C. over 3 hr, diluted with 25 mL sat. NaHCO$_3$ and extracted with 3×50 mL ethyl acetate. The combined organics are washed with 50 mL water and 50 mL brine. The resulting organic layer is dried over anhydrous MgSO$_4$ and the solvent removed in vacuo. The residue is flash chromatographed with 1% methanol in dichloromethane to afford 800 mg (57%) ethyl 3-[(2,5-dimethoxyphenyl)hydroxymethyl]-imidazolo[1,2-a]pyridine-2-carboxylate.

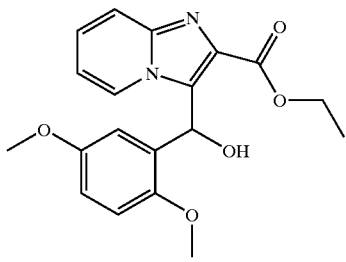

A solution of 356 mg (1.0 mmol) of ethyl 3-[(2,5-dimethoxyphenyl)hydroxymethyl]-imidazolo[1,2-a]pyridine-2-carboxylate in 20 mL dichloromethane is treated at room temperature with 70 mg (1.0 mmol) imidazole and 150 mg (1.0 mmol) t-butyldimethylsilyl chloride. The mixture is stirred at room temperature for 18 hr, diluted with 25 mL sat. NaHCO$_3$ and extracted with 3×20 mL dichloromethane. The combined organics are washed with 50 mL water and 50 mL brine. The resulting organic layer is dried over anhydrous MgSO$_4$ and the solvent removed in vacuo to yield 459 mg (98%) ethyl 3-[(2,5-dimethoxyphenyl)(1,1,2,2-tetramethyl-1-silapropoxy)methyl-imidazolo[1,2-a]pyridine-2-carboxylate.

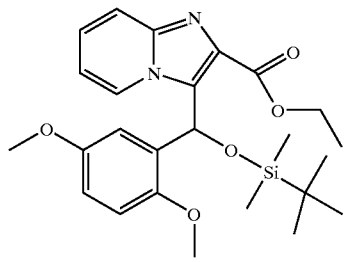

A solution of 470 mg (1.0 mmol) of ethyl 3-[(2,5-dimethoxyphenyl)(1,1,2,2-tetramethyl-1-silapropoxy)methyl-imidazolo[1,2-a]pyridine-2-carboxylate in 5 mL THF is treated at 0° C. with 1.2 mL (1.2 mmol) 1M lithium aluminum hydride in THF. After 1 hr the reaction is allowed to warm up to room temperature and carefully quenched by addition of 1 mL 2M potassium hydroxide. The mixture is extracted with 3×10 mL ethyl acetate and the combined extracts washed with 10 mL brine and dried over anhydrous MgSO$_4$ and the solvent removed in vacuo to afford 334 mg (78%) {3-[(2,5-dimethoxyphenyl)(1,1,2,2-tetramethyl-1-silapropoxy)methyl-imidazolo[1,2-a]pyridin-2-yl}methan-1-ol.

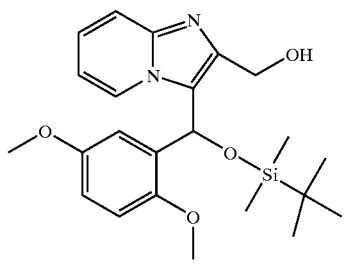

Following procedures described earlier 1-{(2,5-dimethoxyphenyl)[2-(chloromethyl)(imidazolo[1,2-a]pyridin-3-yl)]methoxy}-1,1,2,2-tetramethyl-1-silapropane is prepared from {3-[(2,5-dimethoxyphenyl)(1,1,2,2-tetramethyl-1-silapropoxy)methyl-imidazolo[1,2-a]pyridin-2-yl}methan-1-ol.

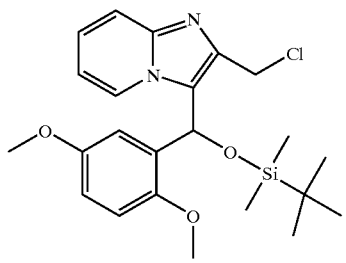

Following procedures described earlier ({3-[(2,5-dimethoxyphenyl)(1,1,2,2-tetramethyl-1-silapropoxy)methyl](imidazolo[1,2-a]pyridin-2-yl)}methyl) (3-methyl)(3-methylbutyl)amine is prepared from 1-{(2,5-dimethoxyphenyl)[2-(chloromethyl)(imidazolo[1,2-a]pyridin-3-yl)]methoxy}-1,1,2,2-tetramethyl-1-silapropane.

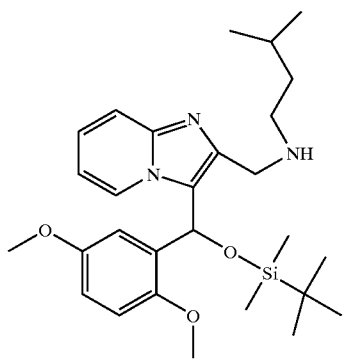

Following procedures described earlier N-({3-[(2,5-dimethoxyphenyl)(1,1,2,2-tetramethyl-1-silapropoxy)methyl](imidazolo [1,2-a]pyridin-2-yl)}methyl) (2-chloro- 3,4-dimethoxyphenyl)-N-(3-methylbutyl)carboxamide is prepared from ({3-[(2,5-dimethoxyphenyl) (1,1,2,2-tetramethyl-1-silapropoxy) methyl](imidazolo[1,2-a]pyridin-2-yl)}methyl) (3-methyl)(3-methylbutyl)amine.

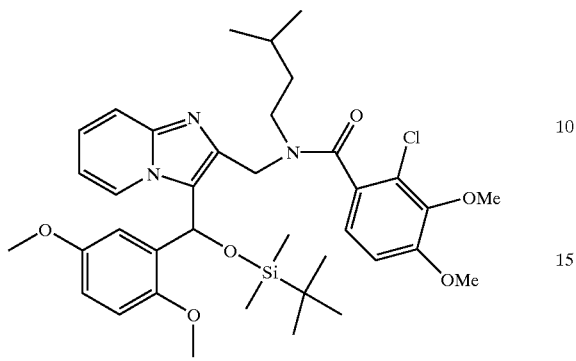

A solution of 390 mg (0.56 mmol) of N-({3-[(2,5-dimethoxyphenyl) (1,1,2,2-tetramethyl-1-silapropoxy) methyl](imidazolo[1,2-a]pyridin-2-yl)}methyl) (2-chloro-3,4-dimethoxyphenyl)-N-(3-methylbutyl)carboxamide in 12 mL THF is treated with 0.70 mL (0.7 mmol) 1M tetabutylammonium fluoride in THF. The mixture is stirred at room temperature for 1 hr, diluted with 15 mL sat. NaHCO$_3$ and extracted with 3×15 mL ether. The combined organics are washed with 25 mL water and 25 mL brine. The resulting organic layer is dried over anhydrous MgSO$_4$ and the solvent removed in vacuo to give the crude material. A small sample of the residue is prep-plate chromatographed (9% MeOH/CH$_2$Cl$_2$/0.5% NH$_4$OH) to afford N-({3-[(2,5-dimethoxyphenyl)hydroxymethyl](imidazolo[1,2-a]pyridin-2-yl)}methyl)(2-chloro-3,4-dimethoxyphenyl)-N-(3-methylbutyl)carboxamide. Mass Spec m/z (M++1) 584.

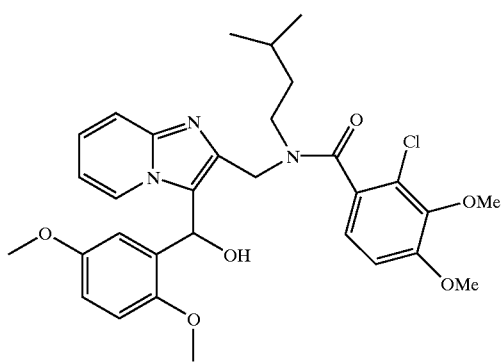

A solution of 58 mg (0.1 mmol) of N-({3-[(2,5-dimethoxyphenyl) hydroxymethyl](imidazolo[1,2-a]pyridin-2-yl)}methyl)(2-chloro-3,4-dimethoxyphenyl)-N-(3-methylbutyl)carboxamide in 5 mL dichloromethane is treated with 116 mg (1.0 mmol) triethylsilane and 114 mg (1.0 mmol) trifluoroacetic acid. The solution is heated in a sealed tube at 60° C. for 18 hr and diluted with 15 mL sat. NaHCO$_3$ and extracted with 3×10 mL dichloromethane. The combined organics are washed with 10 mL water and 10 mL brine. The resulting organic layer is dried over anhydrous MgSO$_4$ and the solvent removed in vacuo to give the crude material. The residue is prep-plate chromatographed (9% MeOH/CH$_2$Cl$_2$/0.5% NH$_4$OH) to afford 33 mg (58%) N-({3-[(2,5-dimethoxyphenyl)methyl](imidazolo[1,2-a]pyridin-2-yl)}methyl)(2-chloro-3,4-dimethoxyphenyl)-N-(3-methylbutyl)carboxamide. Mass Spec m/z (M$^+$+1) 567.

Example 8
General Procedure for the Preparation of Pyridazine Derivatives as shown in Scheme 7
N-({3-[(2-Methoxy-5-bromophenyl)methyl]-6-chloro(imidazolo[1,2-b]pyridazin-2-yl)}methyl)(2-chloro-3,4-dimethoxyphenyl-N-(3-methylbutyl) carboxamide

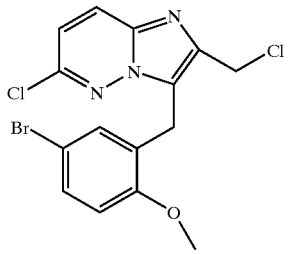

Using the procedures given in Example 1, 4-bromo-2-{[6-chloro-2-(chloromethyl)(imidazolo[1,2-b]pyridazin-3-yl)]methyl}-1-methoxybenzene is prepared starting from 3-amino-6-chloropyridazine and ethyl 3-bromo-4-(5-bromo-2-methoxyphenyl)-2-oxobutanoate.

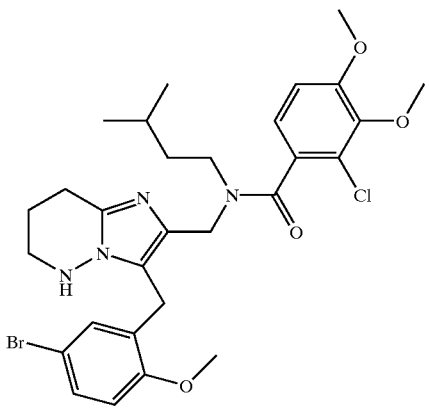

Following the procedures given in Example 2, 4-bromo-2-{[6-chloro-2-(chloromethyl)(imidazolo[1,2-b]pyridazin-3-yl)]methyl}-1-methoxybenzene is converted to the title compound. Mass Spec m/z (M$^+$+1) 651.

N-({3-[(5-bromo-2-Methoxyphenyl)methyl](5H,6H, 7H, 8H-tetrahydroimidazolo[1,2-b]pyridazin-2-yl}methyl) (2-chloro-3,4-dimethoxyphenyl)-N-(3-methylbutyl)carboxamide A solution of 130 mg (0.2 mmol) N-({3-[(5-bromo-2-methoxyphenyl)methyl]-6-chloro(imidazolo[1,2-b]pyridazin-2-yl)}methyl) (2-chloro-3,4-dimethoxyphenyl)-N-(3-methylbutyl)carboxamide in 4 mL ethanol is treated with sodium borohydride 8 mg (0.2 mmol) in ethanol (2 mL). The reaction mixture is heated at reflux for 18 hr, cooled to 0° C. and quenched by dropwise addition of 1M hydrochloric acid. The mixture is neutralized by addition of 1M sodium hydroxide, reduced in volume in vacuo and extracted with 3×20 mL dichloromethane. The combined extract is dried over anhydrous $MgSO_4$ and the solvent removed in vacuo to give the crude residue. The residue is prep-plate chromatographed (5% $MeOH/CH_2Cl_2/0.5\%$ $NH_4OH$) to afford 51 mg (41%) N-({3-[(5-bromo-2-methoxyphenyl)methyl](5H,6H,7H,8H-tetrahydroimidazolo[pyridazin-2-yl}methyl)(2-chloro-3,4-dimethoxyphenyl)-N-(3-methylbutyl)carboxamide. Mass Spec m/z (M$^+$+1) 621.

N-({3-[(5-bromo-2-Methoxyphenyl)methyl]-6-ethoxy(imidazolo[1,2-b]pyridazin-2-yl)}methyl)(2-chloro-3,4-dimethoxyphenyl)-N-(3-methylbutyl)carboxamide

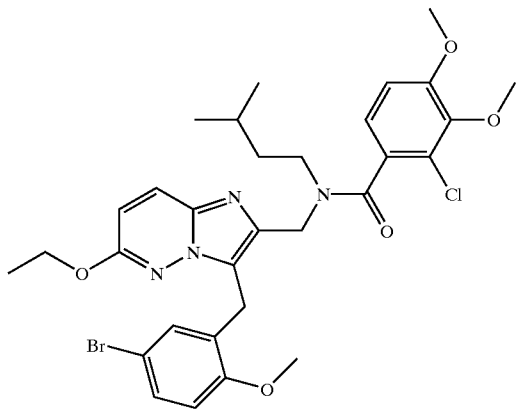

The sodium borohydride reduction of N-({3-[(5-bromo-2-methoxyphenyl) methyl]-6-chloro(imidazolo[1,2-b]pyridazin-2-yl)}methyl) (2-chloro-3,4-dimethoxyphenyl)-N-(3-methylbutyl)carboxamide described previously also produced the title compound. Mass Spec m/z (M$^+$+1) 663.

N-({3-[(5-bromo-2-Methoxyphenyl)methyl]-6-(methylamino)(imidazolo[1,2-b]pyridazin-2-yl)}methyl)(2-chloro-3,4-dimethoxyphenyl)-N-(3-methylbutyl)carboxamide

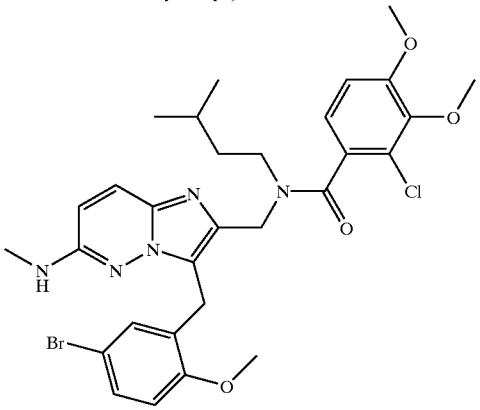

A solution of 130 mg (0.2 mmol) N-({3-[(5-bromo-2-methoxyphenyl)methyl]-6-chloro(imidazolo[1,2-b]pyridazin-2-yl)}methyl)(2-chloro-3,4-dimethoxyphenyl)-N-(3-methylbutyl)carboxamide in DMSO (3 mL) is treated with 2M methyl amine in THF 1.5 mL (3.0 mmol). The reaction mixture is heated to 150° C. in a sealed tube for 18 hr and following cooling partitioned between ethyl acetate and water. The organic extract is washed with 5×10 mL water, dried over anhydrous $MgSO_4$ and the solvent removed in vacuo to give the crude residue. The residue is prep-plate chromatographed (9% $MeOH/CH_2Cl_2/0.5\%$ $NH_4OH$) to afford 31 mg (24%) of the title compound. Mass Spec m/z (M$^+$+1) 646.

Additional compounds of the invention which may be prepared by the methods outlined in Reaction Schemes 1–7 are shown in Table III.

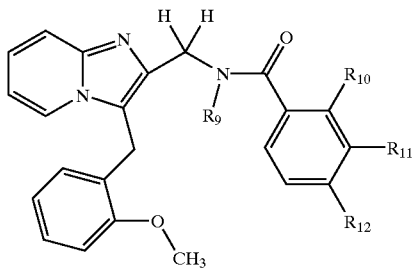

| Ex # | R9 | R10 | R11 | R12 |
|---|---|---|---|---|
| 1. | ![X9 branched with H3C, CH3] | Cl, X10 | H3C-N-CH3 (with ethyl-O-X11) | H3C-O-X12 |

-continued
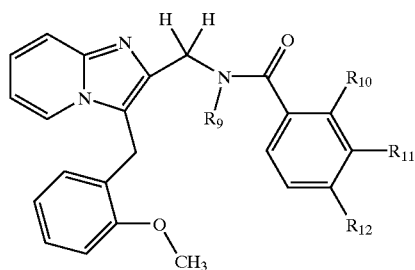
| Ex # | R9 | R10 | R11 | R12 |
|---|---|---|---|---|
| 2. | | | | |
| 3. | | | | |
| 4. | | | | |
| 5. | | | | |
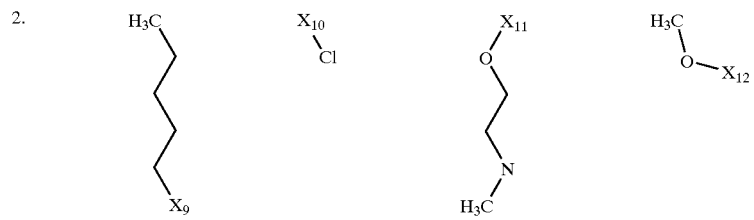
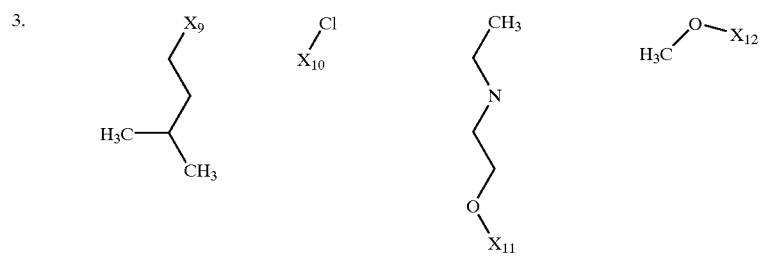
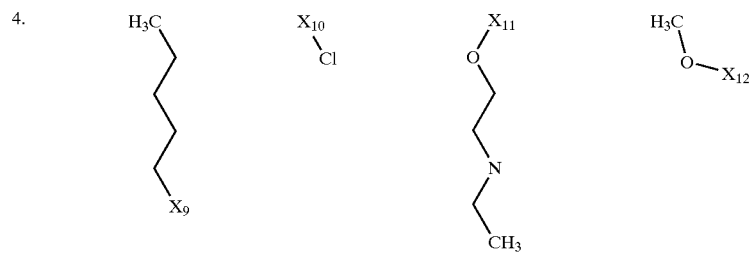
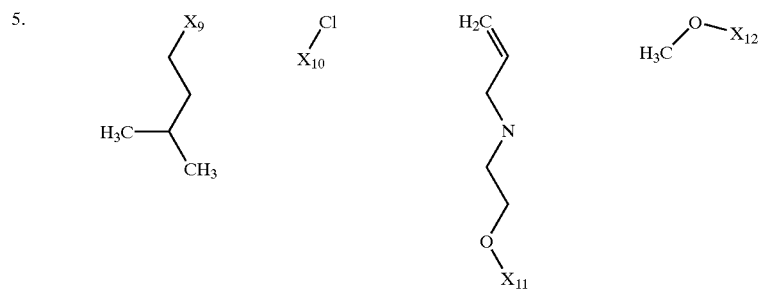

-continued
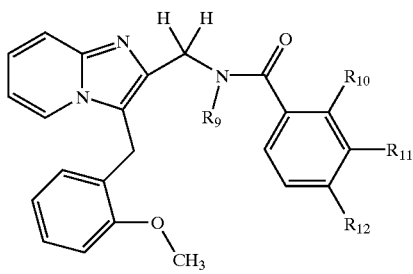
| Ex # | R9 | R10 | R11 | R12 |
|---|---|---|---|---|
| 6. | isopentyl-X9 | Cl, X10 | CH3CH2-N(CH2CH2-O-X11)- | H3C-O-X12 |
| 7. | pentyl-X9, CH3 | X10, Cl | X11-O-CH2CH2-N(CH2CH2CH3)- | H3C-O-X12 |
| 8. | isopentyl-X9 | Cl, X10 | cyclopropyl-CH2-N(CH2CH2-O-X11)- | H3C-O-X12 |
| 9. | pentyl-X9, CH3 | X10, Cl | X11-O-CH2CH2-N(CH2-cyclopropyl)- | CH3-O-X12 |

-continued
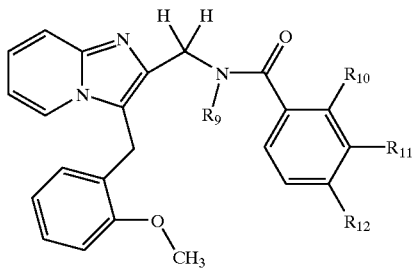
| Ex # | R9 | R10 | R11 | R12 |
|---|---|---|---|---|
| 10. | (CH₃)₂CHCH₂CH₂-X₉ | Cl, X₁₀ | CH₃-CH(CH₂N(...)CH₂CH₂-O-X₁₁) | H₃C-O-X₁₂ |
| 11. | H₃C(CH₂)₄-X₉ | X₁₀-Cl | X₁₁-O-CH₂CH₂-N(CH₂CH₂CH₂CH₃) | H₃C-O-X₁₂ |
| 12. | (CH₃)₂CHCH₂CH₂-X₉ | Cl, X₁₀ | H₃C-CH(CH₃)-CH₂-N-CH₂CH₂-O-X₁₁ | H₃C-O-X₁₂ |
| 13. | H₃C(CH₂)₄-X₉ | X₁₀-Cl | X₁₁-O-CH₂CH₂-N-CH₂CH(CH₃)₂ | H₃C-O-X₁₂ |

-continued
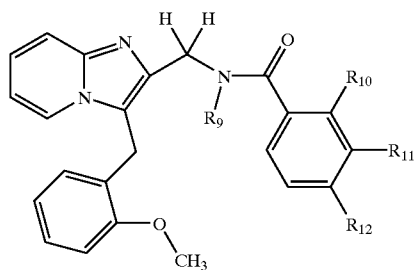
| Ex # | R9 | R10 | R11 | R12 |
|---|---|---|---|---|
| 14. | | | | |
| 15. | | | | |
| 16. | | | | |
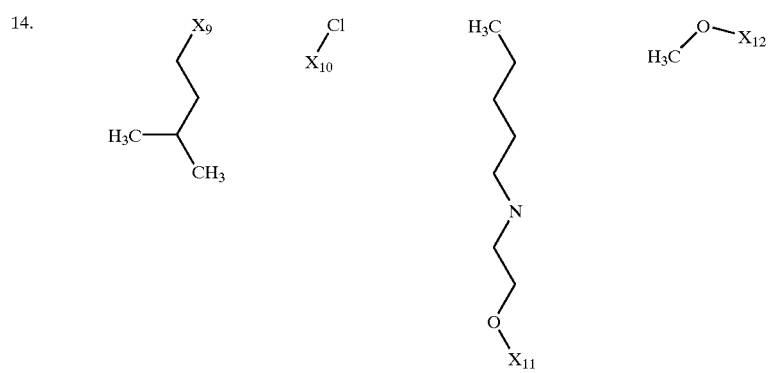
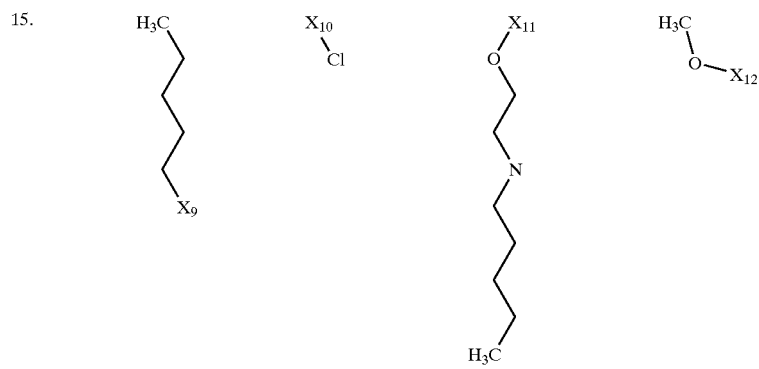
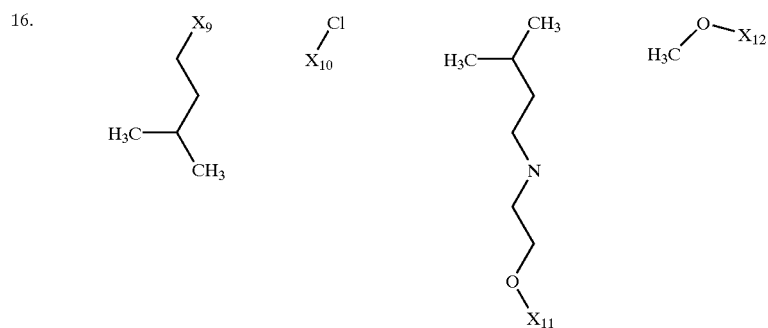

-continued
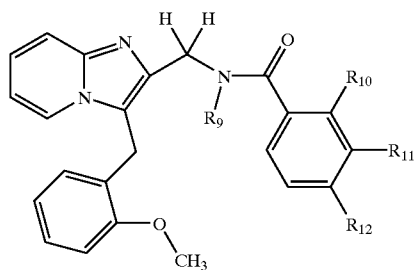
| Ex # | R9 | R10 | R11 | R12 |
|---|---|---|---|---|
| 17. | H₃C—(CH₂)₄—X₉ | X₁₀—Cl | X₁₁—O—CH₂CH₂—N(CH₂CH(CH₃)₂) | H₃C—O—X₁₂ |
| 18. | (CH₃)₂CHCH₂CH₂—X₉ | X₁₀—Cl | CH₃CH₂CH(CH₃)CH₂—N—CH₂CH₂—O—X₁₁ | H₃C—O—X₁₂ |
| 19. | H₃C—(CH₂)₄—X₉ | X₁₀—Cl | X₁₁—O—CH₂CH₂—N—CH₂CH(CH₃)CH₂CH₃ | H₃C—O—X₁₂ |

-continued
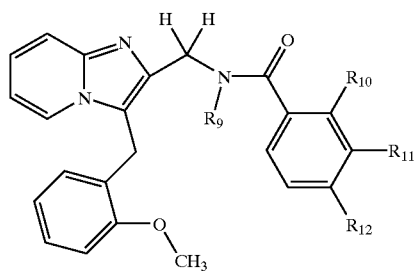
| Ex # | R9 | R10 | R11 | R12 |
|---|---|---|---|---|
| 20. | (CH₃)₂CHCH₂CH₂-X₉ | Cl, X₁₀ | CH₃-(CH₂)₄-N(CH₂CH₂O-X₁₁)- | H₃C-O-X₁₂ |
| 21. | H₃C-(CH₂)₃-X₉ | X₁₀, Cl | X₁₁-O-CH₂CH₂-N-(CH₂)₅CH₃ | H₃C-O-X₁₂ |
| 22. | (CH₃)₂CHCH₂CH₂-X₉ | X₁₀, Cl | X₁₁-O-CH₂CH₂-N(cyclopropyl) | H₃C-O-X₁₂ |
| 23. | X₉-(CH₂)₄-CH₃ | Cl, X₁₀ | (cyclopropyl)-N-CH₂CH₂-O-X₁₁ | H₃C-O-X₁₂ |
| 24. | (CH₃)₂CHCH₂CH₂-X₉ | Cl, X₁₀ | (CH₃)₂CH-N-CH₂CH₂-O-X₁₁ | H₃C-O-X₁₂ |

-continued
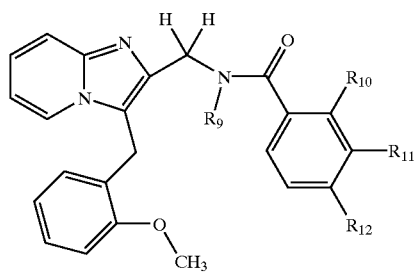
| Ex # | R9 | R10 | R11 | R12 |
|---|---|---|---|---|
| 25. | H₃C-(CH₂)₄-X₉ | X₁₀-Cl | X₁₁-O-CH₂CH₂-N(iPr)- | H₃C-O-X₁₂ |
| 26. | (CH₃)₂CH-CH₂-CH₂-X₉ | X₁₀-Cl | X₁₁-O-CH₂CH₂-N(cyclobutyl)- | H₃C-O-X₁₂ |
| 27. | X₉-(CH₂)₄-CH₃ | Cl-X₁₀ | cyclobutyl-N-CH₂CH₂-O-X₁₁ | X₁₂-O-CH₃ |
| 28. | X₉-CH₂CH₂-CH(CH₃)₂ | Cl-X₁₀ | H₃C-CH(CH₃)-N(CH₂CH₂-O-X₁₁)-CH(CH₃)CH₂CH₃ | H₃C-O-X₁₂ |
| 29. | H₃C-(CH₂)₄-X₉ | X₁₀-Cl | X₁₁-O-CH₂CH₂-N-CH(CH₃)CH₂CH₃ | H₃C-O-X₁₂ |

-continued
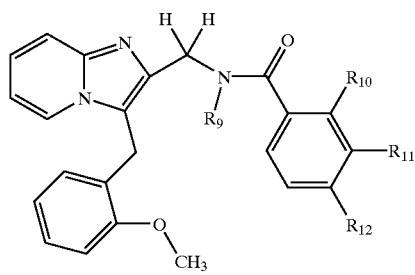
| Ex # | R9 | R10 | R11 | R12 |
|---|---|---|---|---|
| 30. | X9-CH2-CH2-CH(CH3)-CH3 (isopentyl with X9) | Cl, X10 | H3C-C(CH3)(CH3)-N(CH2CH2-O-X11)- (tert-butyl-N-CH2CH2-O-X11) | H3C-O-X12 |
| 31. | H3C-(CH2)4-X9 | X10-Cl | X11-O-CH2CH2-N(C(CH3)3)- | H3C-O-X12 |
| 32. | X9-CH2-CH2-CH(CH3)-CH3 | Cl, X10 | cyclopentyl-N(CH2CH2-O-X11)- | H3C-O-X12 |
| 33. | H3C-(CH2)4-X9 | X10-Cl | X11-O-CH2CH2-N(cyclopentyl)- | H3C-O-X12 |

-continued
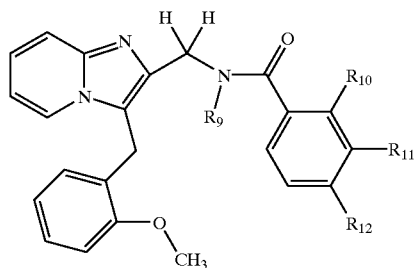
| Ex # | R9 | R10 | R11 | R12 |
|---|---|---|---|---|
| 34. | (CH3)2CHCH2CH2-X9 | Cl, X10 | CH3-CH(-)-N-CH2CH2-O-X11 (with CH3 branch) | H3C-O-X12 |
| 35. | H3C-(CH2)4-X9 | X10-Cl | X11-O-CH2CH2-N(-)-CH(CH3)CH2CH2CH3 | H3C-O-X12 |
| 36. | (CH3)2CHCH2CH2-X9 | Cl, X10 | (CH3)2CH-CH(CH3)-N-CH2CH2-O-X11 | H3C-O-X12 |
| 37. | H3C-(CH2)4-X9 | X10-Cl | X11-O-CH2CH2-N(-)-CH(CH3)CH(CH3)2 | H3C-O-X12 |

-continued
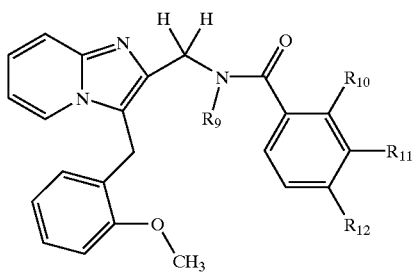
| Ex # | R9 | R10 | R11 | R12 |
|---|---|---|---|---|
| 38. | isopentyl-X9 (H3C-CH(CH3)-CH2-CH2-X9) | Cl, X10 | H3C-CH2-C(Et)(H)-N-CH2CH2-O-X11 (3-pentyl with N-CH2CH2OX11) | H3C-O-X12 |
| 39. | H3C-(CH2)4-X9 | X10-Cl | X11-O-CH2CH2-N-CH(Et)2 | H3C-O-X12 |
| 40. | isopentyl-X9 | Cl, X10 | H3C-CH2-C(CH3)2-N-CH2CH2-O-X11 | H3C-O-X12 |
| 41. | H3C-(CH2)4-X9 | X10-Cl | X11-O-CH2CH2-N-C(CH3)2-CH2CH3 | H3C-O-X12 |

-continued
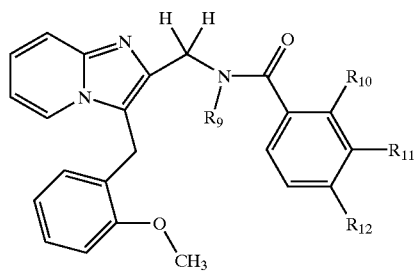
| Ex # | R9 | R10 | R11 | R12 |
|---|---|---|---|---|
| 42. | X9–CH2CH2–CH(CH3)2 (isopentyl with X9) | Cl, X10 | cyclohexyl-N(–CH2CH2–O–X11)– | H3C–O–X12 |
| 43. | H3C–(CH2)4–X9 | X10, Cl | –O–X11–CH2CH2–N(cyclohexyl)– | H3C–O–X12 |
| 44. | X9–CH2CH2–CH(CH3)2 | Cl, X10 | CH3–O–CH2CH2–N(–CH2CH2–O–X11)– | H3C–O–X12 |
| 45. | H3C–(CH2)4–X9 | X10, Cl | X11–O–CH2CH2–N(–CH2CH2–O–CH3)– | H3C–O–X12 |

-continued
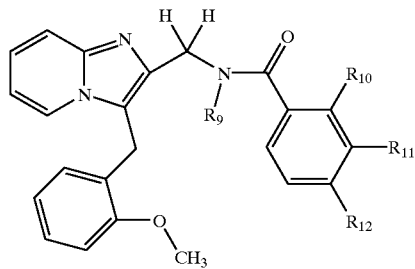
| Ex # | R9 | R10 | R11 | R12 |
|---|---|---|---|---|
| 46. | (CH3)2CHCH2CH2-X9 | Cl, X10 | H3C-O-CH2CH2CH2-N(CH2CH2-O-X11) | H3C-O-X12 |
| 47. | H3C-(CH2)4-X9 | X10, Cl | X11-O-CH2CH2-N(CH2CH2CH2-O-CH3) | H3C-O-X12 |
| 48. | (CH3)2CHCH2CH2-X9 | Cl, X10 | (tetrahydrofuran-2-yl)CH2-N-CH2CH2-O-X11 | H3C-O-X12 |
| 49. | H3C-(CH2)4-X9 | X10, Cl | X11-O-CH2CH2-N-CH2-(tetrahydrofuran-2-yl) | H3C-O-X12 |

-continued
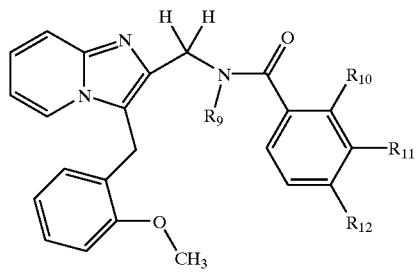
| Ex # | R9 | R10 | R11 | R12 |
|---|---|---|---|---|
| 50. | | | | |
| 51. | | | | |
| 52. | | | | |
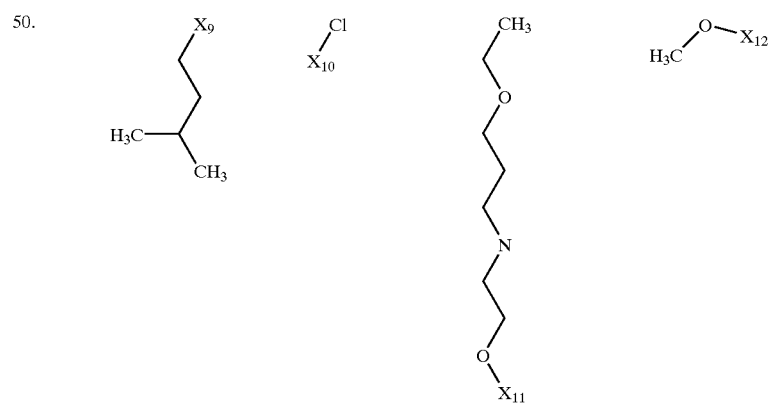
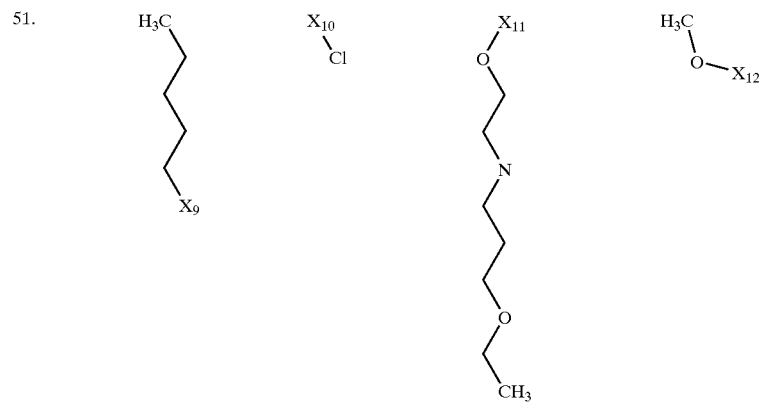
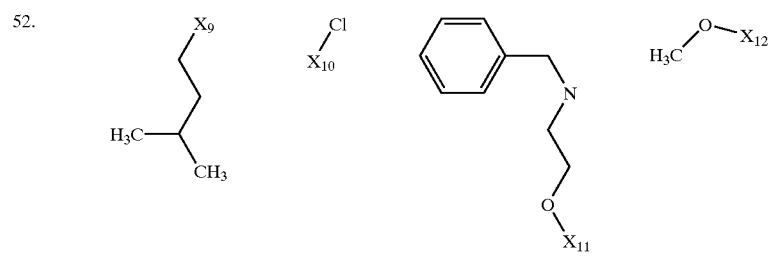

-continued
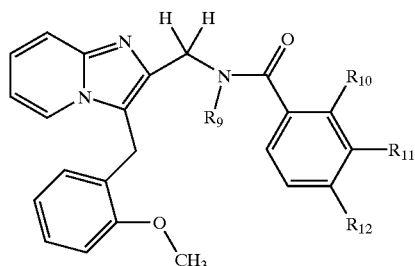
| Ex # | R9 | R10 | R11 | R12 |
|---|---|---|---|---|
| 53. | H₃C–(CH₂)₄–X₉ | X₁₀–Cl | X₁₁–O–CH₂CH₂–N(CH₂Ph) | H₃C–O–X₁₂ |
| 54. | (CH₃)₂CH–CH₂–CH₂–X₉ | Cl–X₁₀ | H₃C–(CH₂)₆–N–CH₂CH₂–O–X₁₁ | H₃C–O–X₁₂, H₃C |
| 55. | H₃C–(CH₂)₄–X₉ | X₁₀–Cl | X₁₁–O–CH₂CH₂–N–(CH₂)₇–CH₃ | H₃C–O–X₁₂ |

-continued
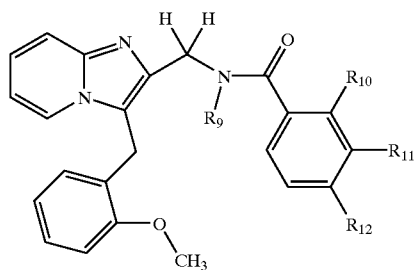
| Ex # | R9 | R10 | R11 | R12 |
|---|---|---|---|---|
| 56. | 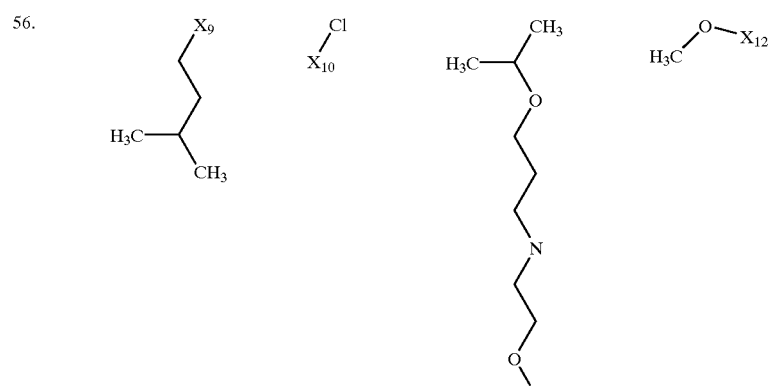 | | | |
| 57. | 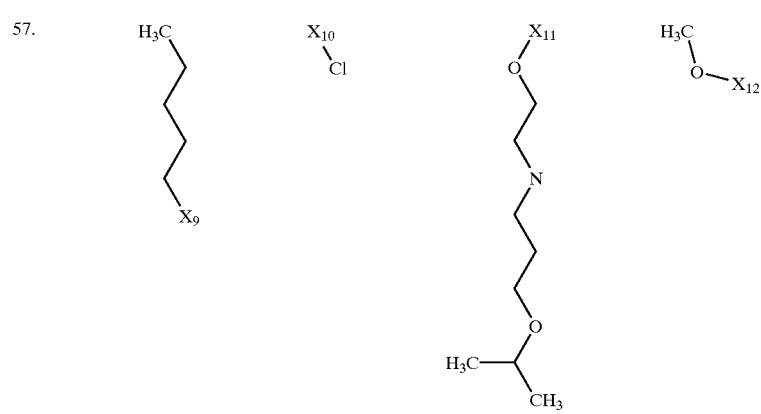 | | | |
| 58. | 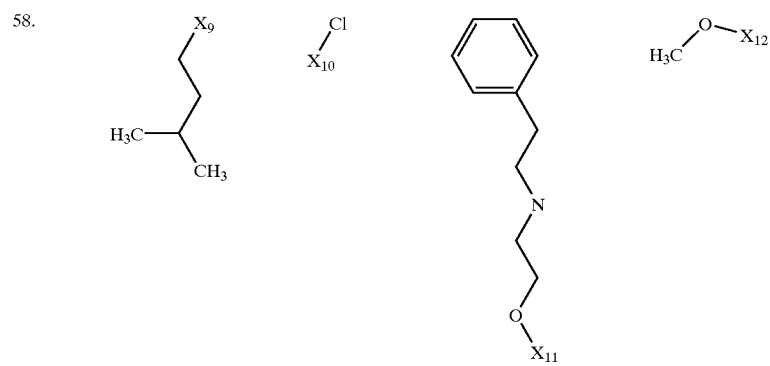 | | | |

-continued
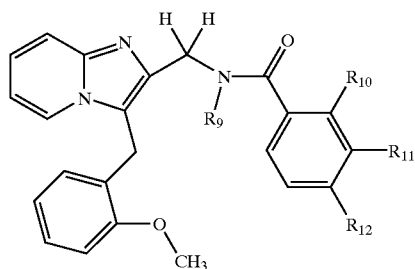
| Ex # | R9 | R10 | R11 | R12 |
|---|---|---|---|---|
| 59. | H₃C-(CH₂)₄-X₉ | X₁₀-Cl | X₁₁-O-CH₂CH₂-N(CH₂CH₂-phenyl) | H₃C-O-X₁₂ |
| 60. | (CH₃)₂CH-CH₂-CH₂-X₉ | Cl-X₁₀ | 4-methylbenzyl-N(CH₂CH₂-O-X₁₁) | H₃C-O-X₁₂ |
| 61. | H₃C-(CH₂)₄-X₉ | X₁₀-Cl | X₁₁-O-CH₂CH₂-N(CH₂-4-methylphenyl) | H₃C-O-X₁₂ |
| 62. | (CH₃)₂CH-CH₂-CH₂-X₉ | Cl-X₁₀ | cyclohexenyl-CH₂CH₂-N(CH₂CH₂-O-X₁₁) | H₃C-O-X₁₂ |

-continued
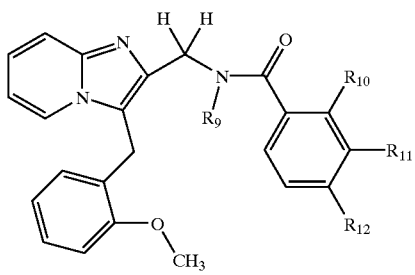
| Ex # | R9 | R10 | R11 | R12 |
|---|---|---|---|---|
| 63. | H3C-CH2-CH2-CH2-CH2-X9 | X10-Cl | X11-O-CH2-CH2-N(CH2CH2-cyclohexenyl) | H3C-O-X12 |
| 64. | X9-CH2-CH2-CH(CH3)-CH3 | Cl-X10 | H3C-(p-phenyl)-CH2-CH2-N-CH2-CH2-O-X11 | H3C-O-X12 with H3C |
| 65. | H3C-CH2-CH2-CH2-CH2-X9 | X10-Cl | X11-O-CH2-CH2-N-CH2-CH2-(p-tolyl-CH3) | H3C-O-X12 |

-continued
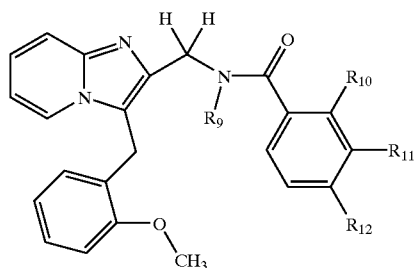
| Ex # | R9 | R10 | R11 | R12 |
|---|---|---|---|---|
| 66. | 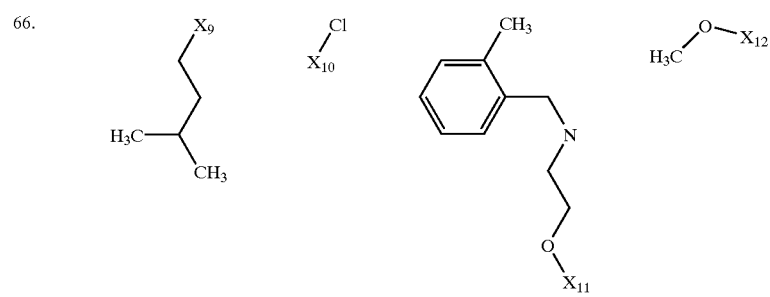 | | | |
| 67. | 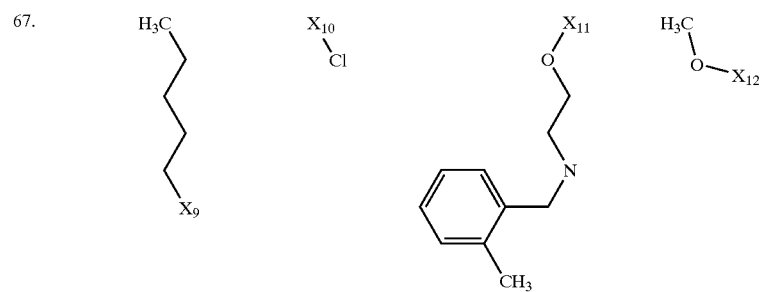 | | | |
| 68. | 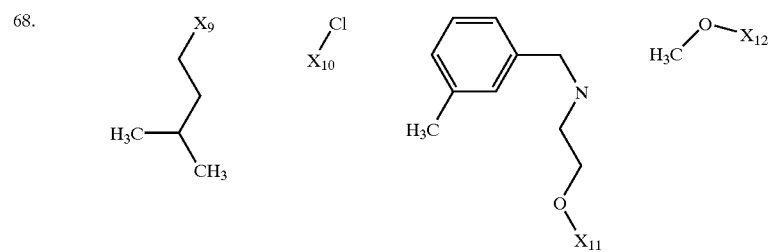 | | | |
| 69. | 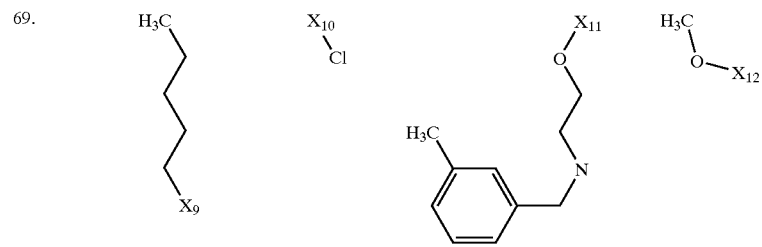 | | | |

-continued
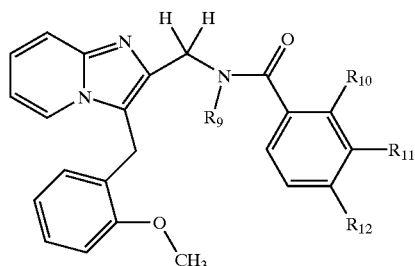
| Ex # | R9 | R10 | R11 | R12 |
|---|---|---|---|---|
| 70. | (X9-CH2CH2-CH(CH3)-CH3) isopentyl-X9 | Cl, X10 | 2-F-benzyl-N(CH2CH2-O-X11) | H3C-O-X12 |
| 71. | H3C-(CH2)4-X9 | X10-Cl | X11-O-CH2CH2-N(2-F-benzyl) | H3C-O-X12 |
| 72. | (X9-CH2CH2-CH(CH3)-CH3) isopentyl-X9 | Cl, X10 | 3-F-benzyl-N(CH2CH2-O-X11) | H3C-O-X12 |
| 73. | H3C-(CH2)4-X9 | X10-Cl | X11-O-CH2CH2-N(3-F-benzyl) | H3C-O-X12 |

-continued
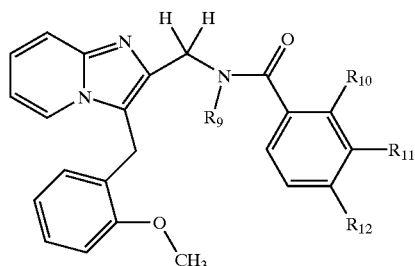
| Ex # | R9 | R10 | R11 | R12 |
|---|---|---|---|---|
| 74. | 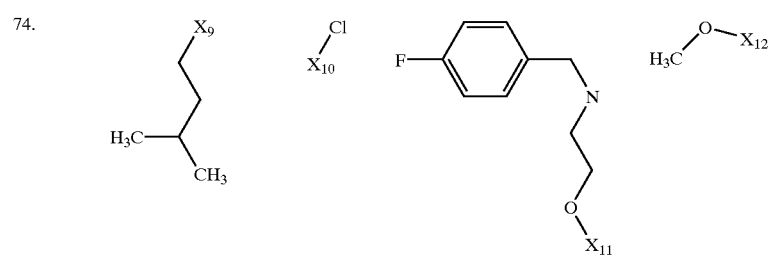 | | | |
| 75. | 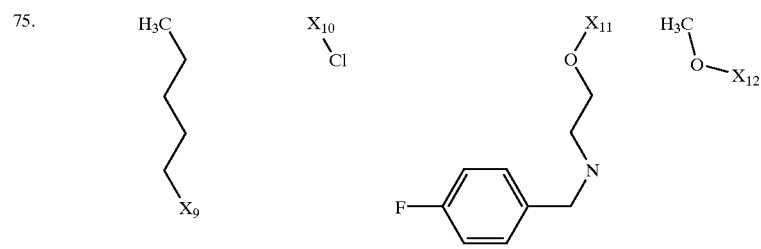 | | | |
| 76. | 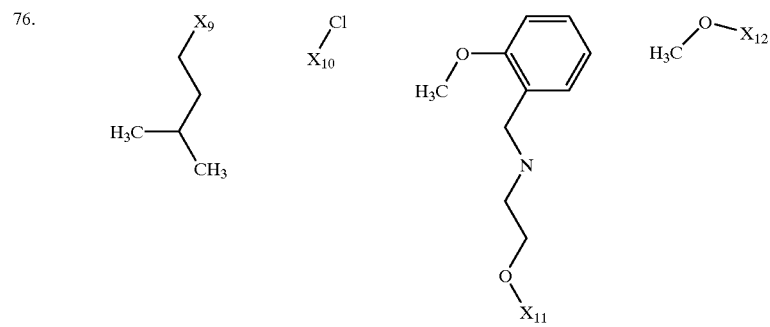 | | | |
| 77. | 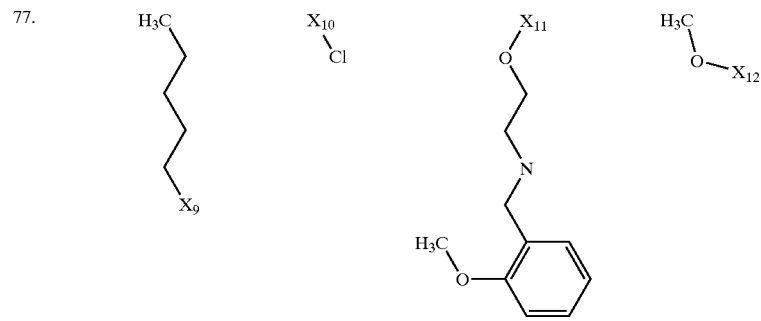 | | | |

-continued
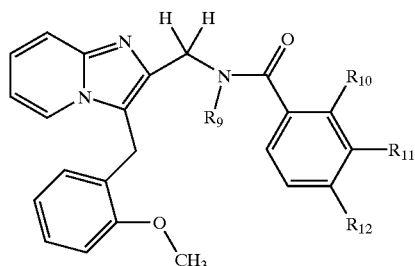
| Ex # | R9 | R10 | R11 | R12 |
|---|---|---|---|---|
| 78. | | | | 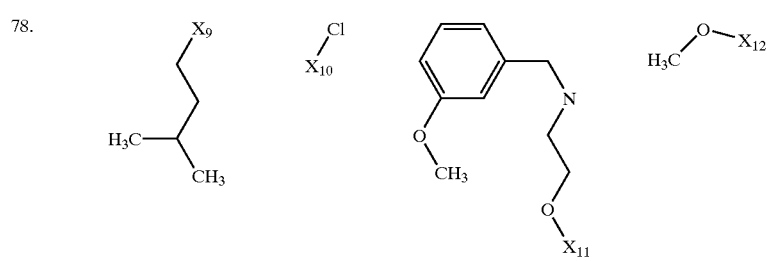 |
| 79. | | | | 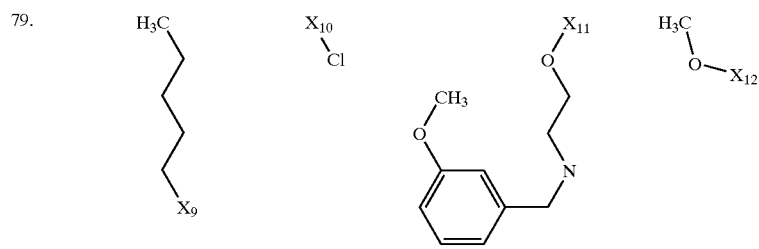 |
| 80. | | | | 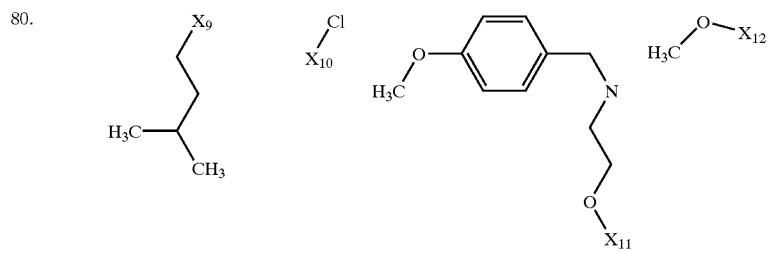 |
| 81. | | | | 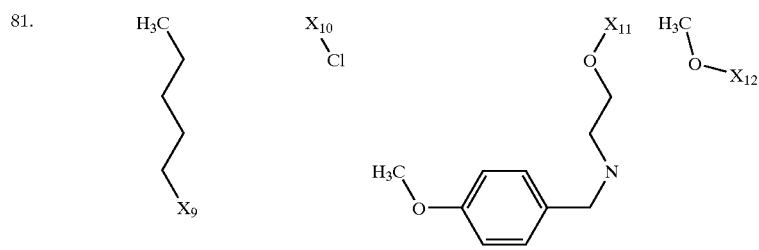 |

-continued
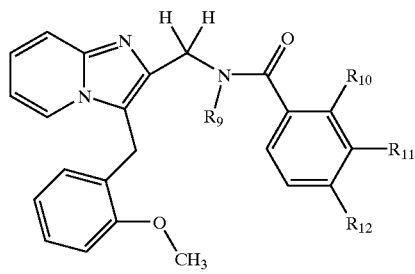
| Ex # | R9 | R10 | R11 | R12 |
|---|---|---|---|---|
| 82. | | | | |
| 83. | | | | |
| 84. | | | | |
| 85. | | | | |
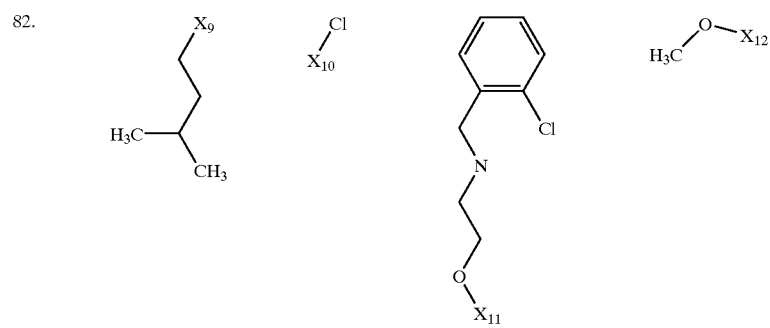
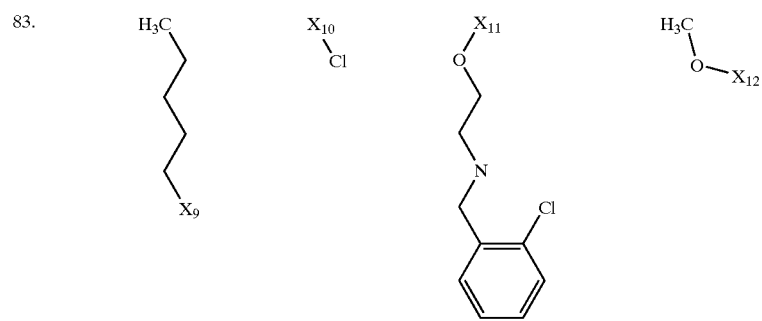
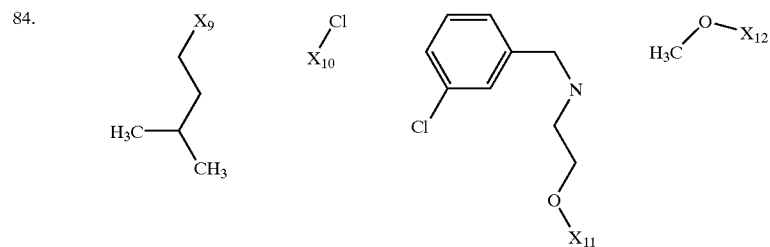
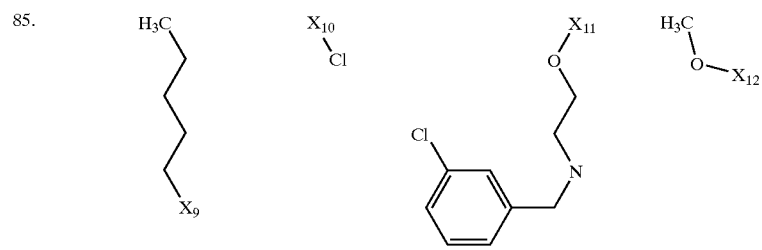

-continued
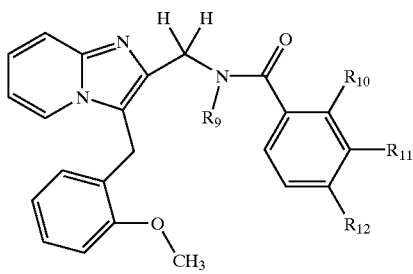
| Ex # | R9 | R10 | R11 | R12 |
|---|---|---|---|---|
| 86. | isopentyl-X9 (H3C)2CHCH2CH2-X9 | Cl, X10 | 4-Cl-C6H4-CH2-N(CH2CH2-O-X11)- | H3C-O-X12 |
| 87. | H3C(CH2)4-X9 | X10, Cl | X11-O-CH2CH2-N(CH2-C6H4-4-Cl)- | H3C-O-X12 |
| 88. | isopentyl-X9 | Cl, X10 | 2-CH3-C6H4-CH2CH2-N(CH2CH2-O-X11)- | H3C-O-X12 |
| 89. | H3C(CH2)4-X9 | X10, Cl | X11-O-CH2CH2-N(CH2CH2-C6H4-2-CH3)- | H3C-O-X12 |

-continued
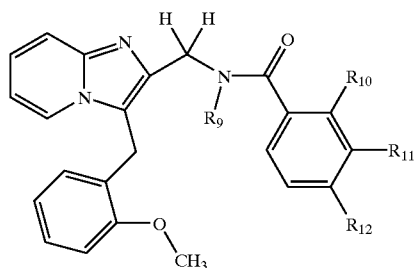
| Ex # | R9 | R10 | R11 | R12 |
|---|---|---|---|---|
| 90. | 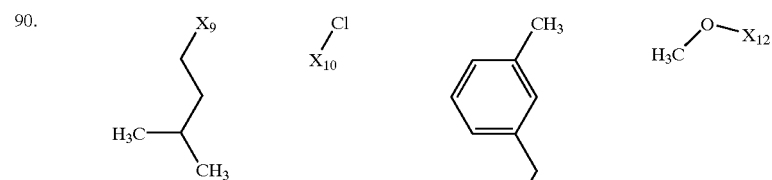 | | | |
| 91. | | | | |
| 92. | | | | |

-continued
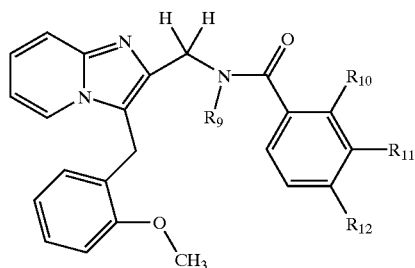
| Ex # | R9 | R10 | R11 | R12 |
| --- | --- | --- | --- | --- |
| 93. | | | | |
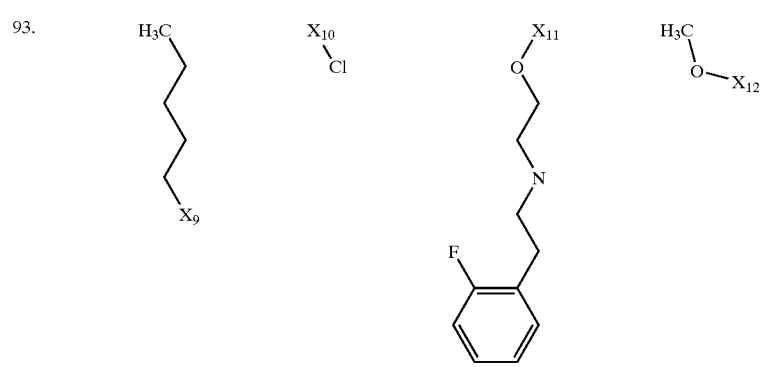
| 94. | | | | |
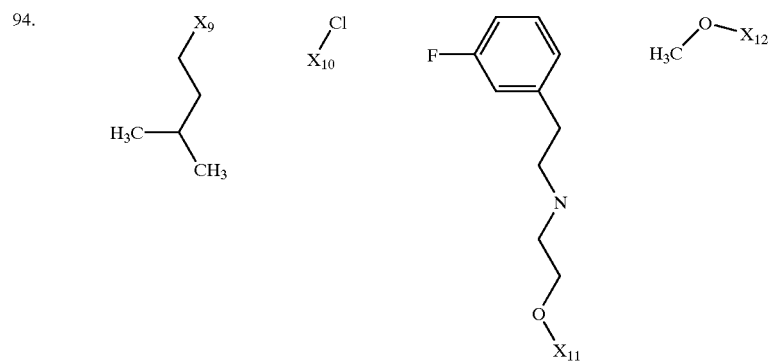
| 95. | | | | |
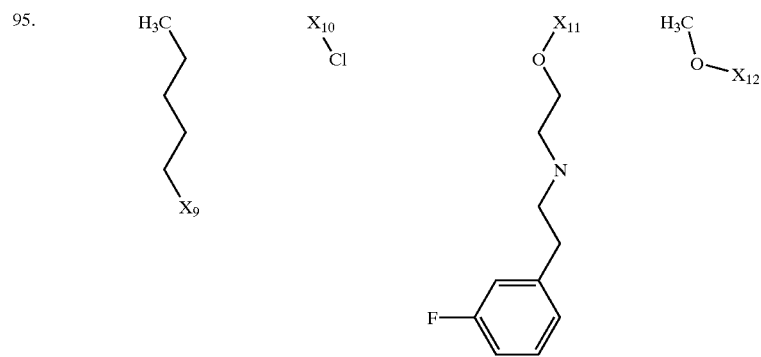

-continued
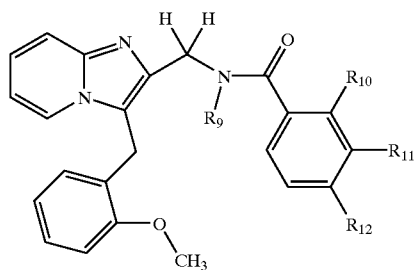
| Ex # | R9 | R10 | R11 | R12 |
|---|---|---|---|---|
| 96. | | | | |
| 97. | | | | |
| 98. | | | | |
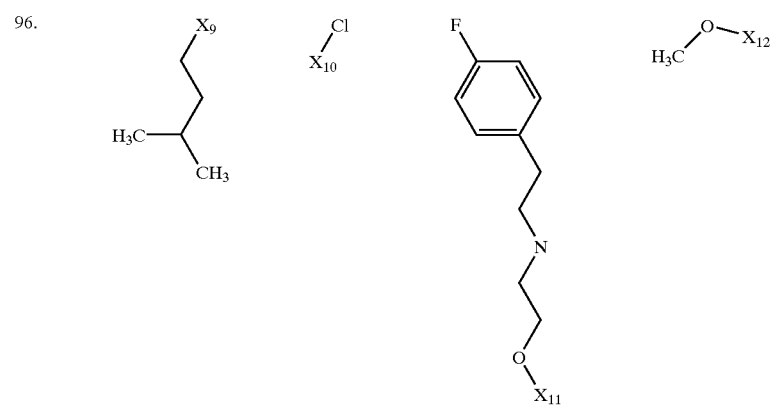
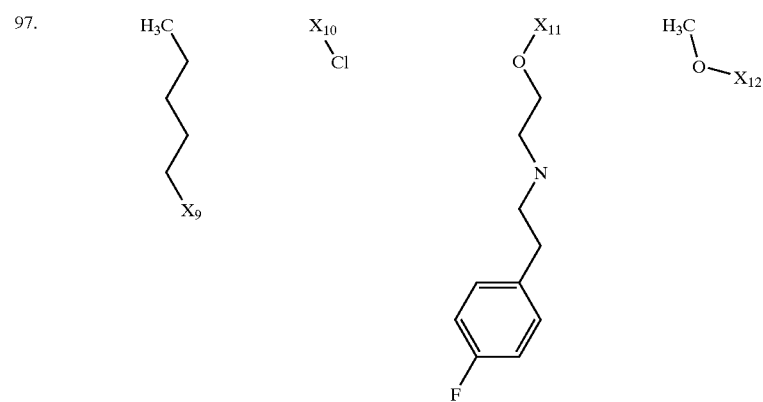
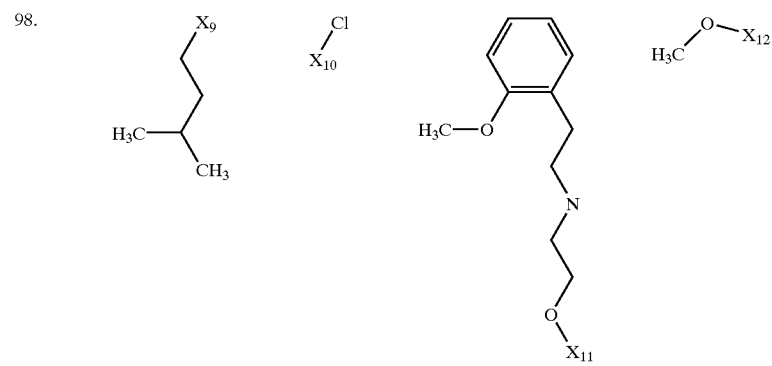

-continued
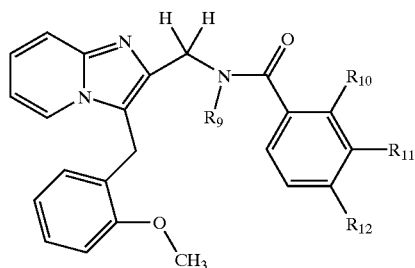
| Ex # | R9 | R10 | R11 | R12 |
|---|---|---|---|---|
| 99. | 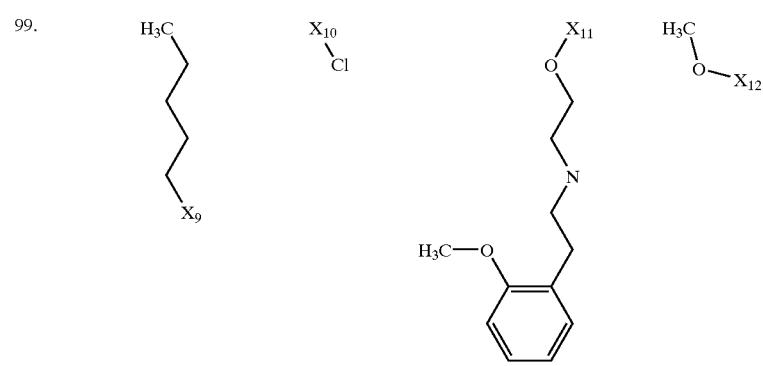 | | | |
| 100. | 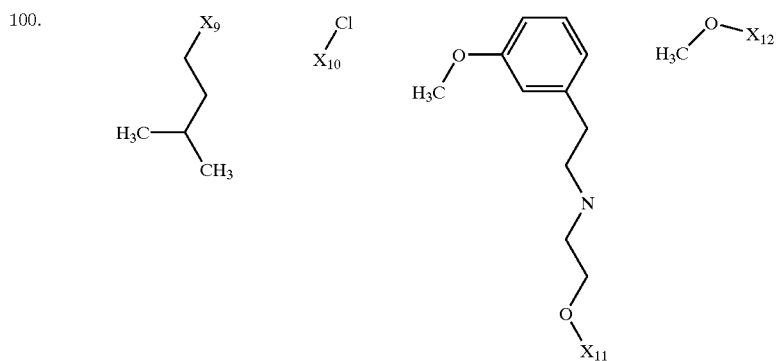 | | | |
| 101. | 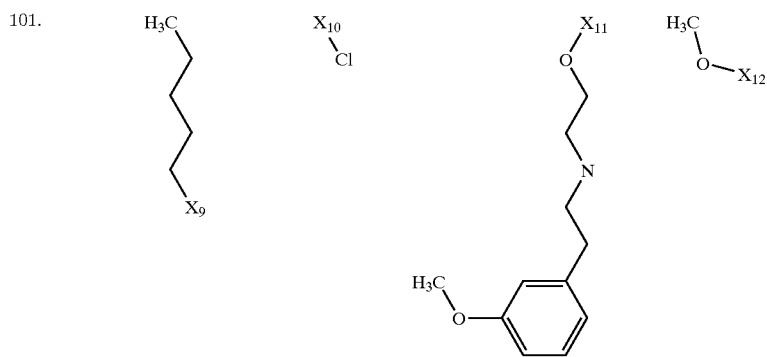 | | | |

-continued
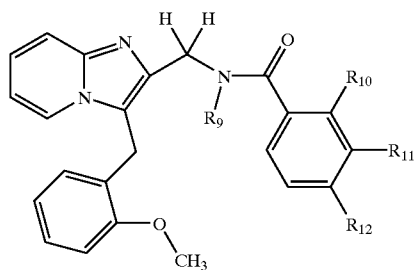
| Ex # | R9 | R10 | R11 | R12 |
|---|---|---|---|---|
| 102. | (3-methylbutyl)-X9 | Cl, X10 | 4-(H3CO)-C6H4-CH2CH2-N(CH2CH2-O-X11)- | H3C-O-X12 |
| 103. | n-pentyl-X9 | X10, Cl | X11-O-CH2CH2-N(CH2CH2-C6H4-4-OCH3)- | H3C-O-X12 |
| 104. | (3-methylbutyl)-X9 | Cl, X10 | 2-Cl-C6H4-CH2CH2-N(CH2CH2-O-X11)- | H3C-O-X12 |

-continued
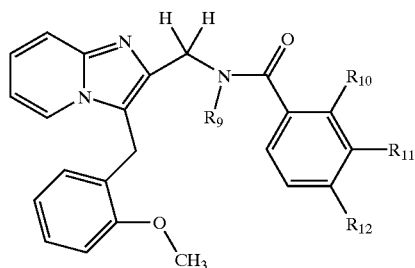
| Ex # | R9 | R10 | R11 | R12 |
| --- | --- | --- | --- | --- |
| 105. | | | | |
| 106. | | | | |
| 107. | | | | |
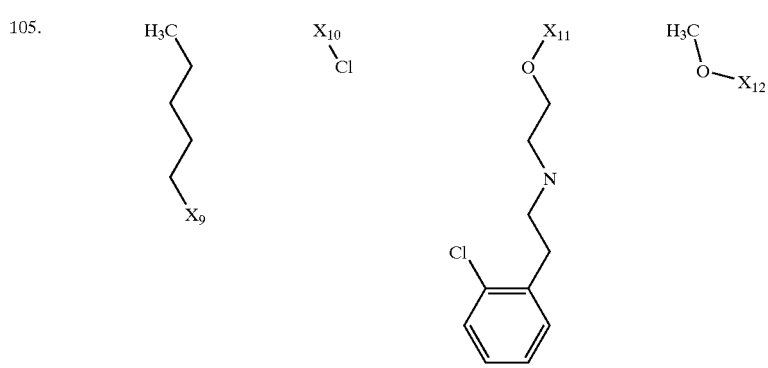
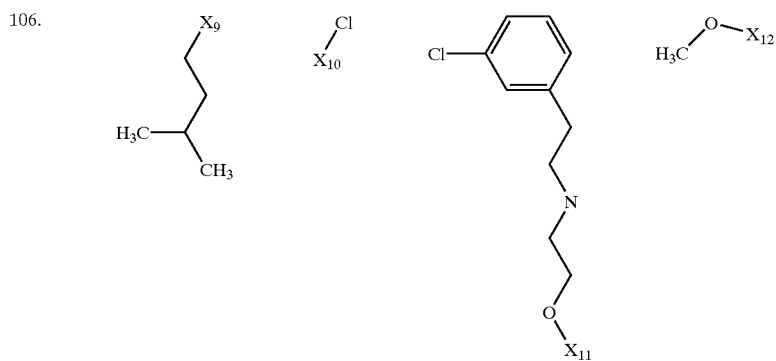
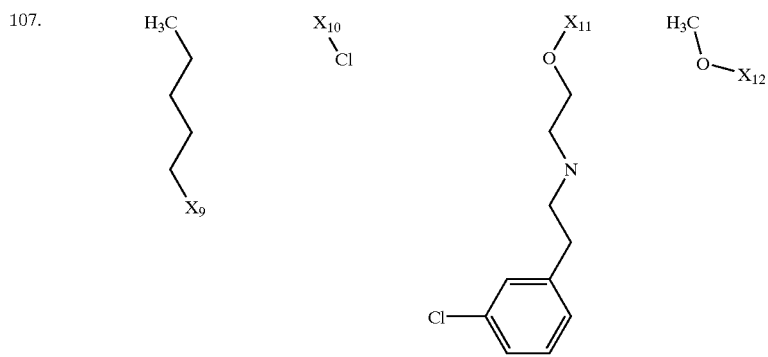

-continued
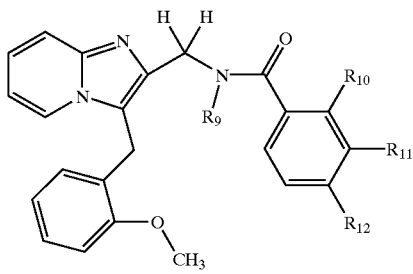
| Ex # | R9 | R10 | R11 | R12 |
|---|---|---|---|---|
| 108. | 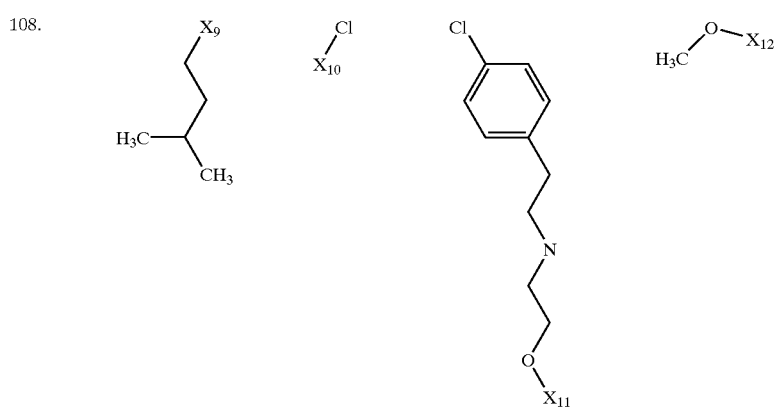 | | | |
| 109. | 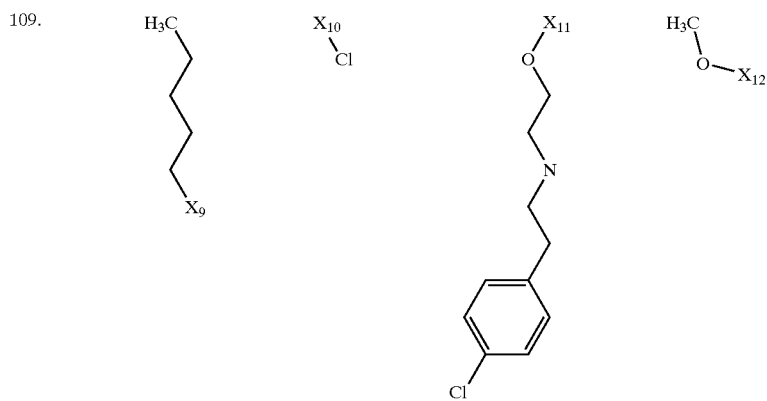 | | | |
| 110. | 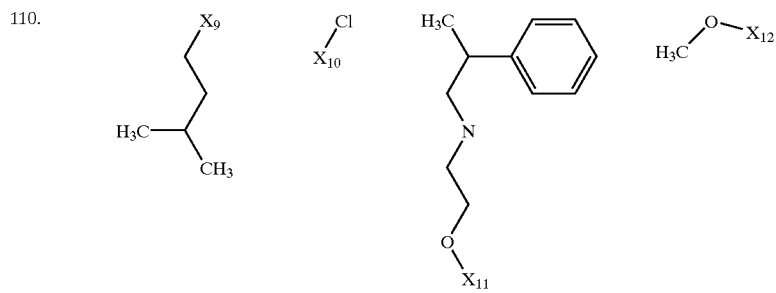 | | | |

-continued
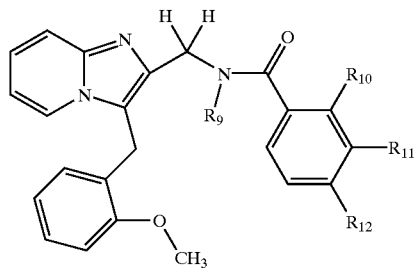
| Ex # | R9 | R10 | R11 | R12 |
|---|---|---|---|---|
| 111. | 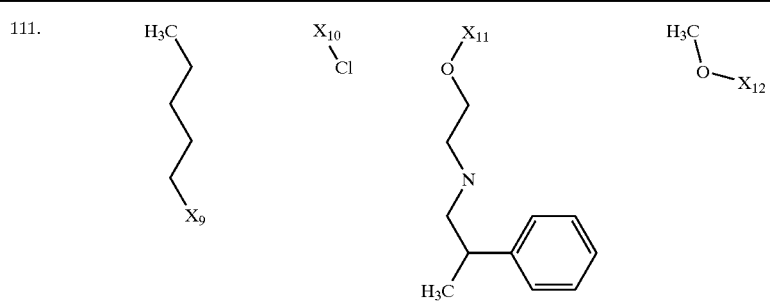 | | | |
| 112. | 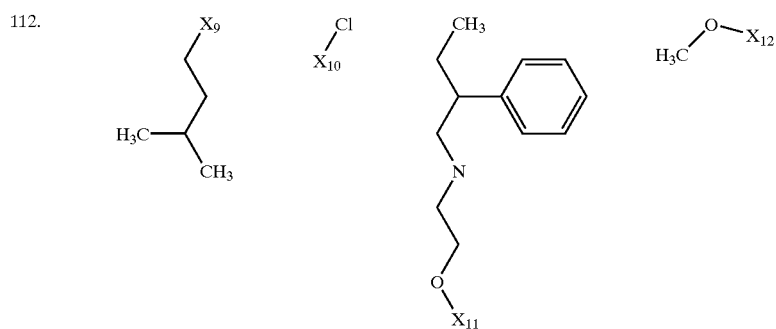 | | | |
| 113. | 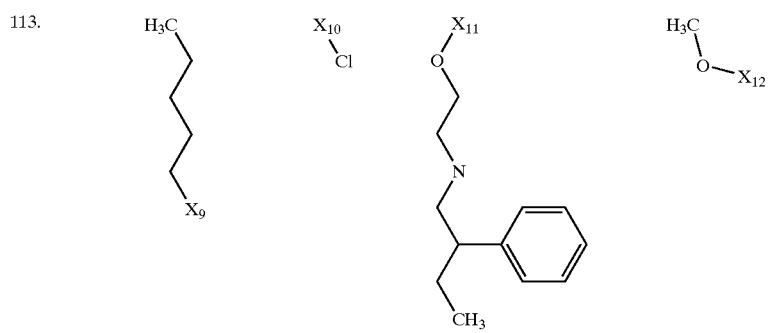 | | | |

-continued
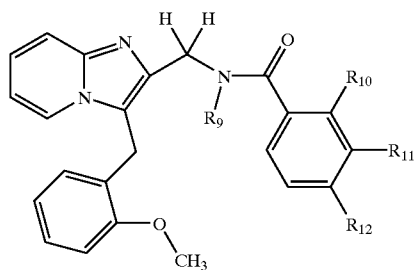
| Ex # | R9 | R10 | R11 | R12 |
|---|---|---|---|---|
| 114. | | | | |
| 115. | | | | |
| 116. | | | | |
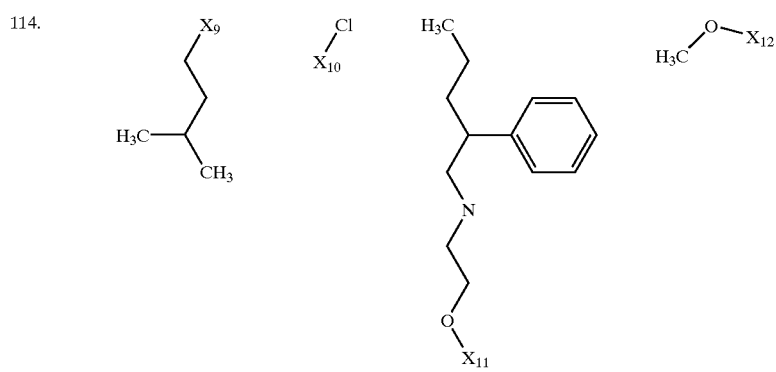
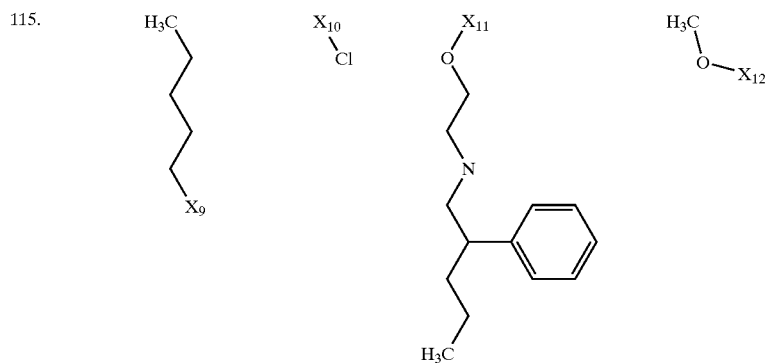
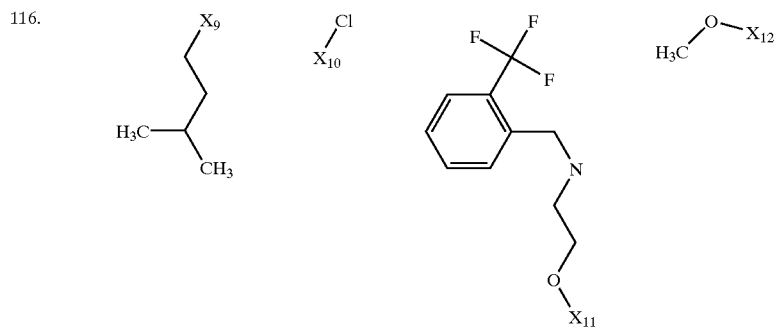

-continued
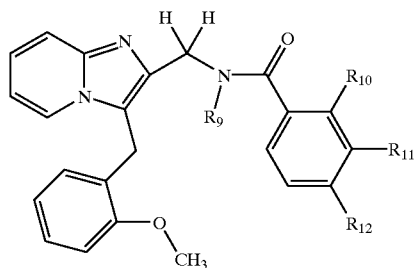
| Ex # | R9 | R10 | R11 | R12 |
|---|---|---|---|---|
| 117. | H₃C-(CH₂)₄-X₉ | X₁₀-Cl | X₁₁-O-CH₂CH₂-N(CH₂-[2-CF₃-phenyl]) | H₃C-O-X₁₂ |
| 118. | (CH₃)₂CH-CH₂-CH₂-X₉ | Cl-X₁₀ | [3-CF₃-phenyl]-CH₂-N-CH₂CH₂-O-X₁₁ | H₃C-O-X₁₂ |
| 119. | H₃C-(CH₂)₄-X₉ | X₁₀-Cl | X₁₁-O-CH₂CH₂-N-CH₂-[3-CF₃-phenyl] | H₃C-O-X₁₂ |
| 120. | (CH₃)₂CH-CH₂-CH₂-X₉ | Cl-X₁₀ | [4-CF₃-phenyl]-CH₂-N-CH₂CH₂-O-X₁₁ | H₃C-O-X₁₂ |

-continued
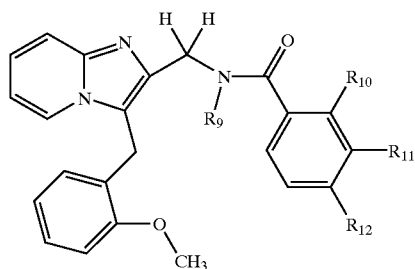
| Ex # | R9 | R10 | R11 | R12 |
|---|---|---|---|---|
| 121. | 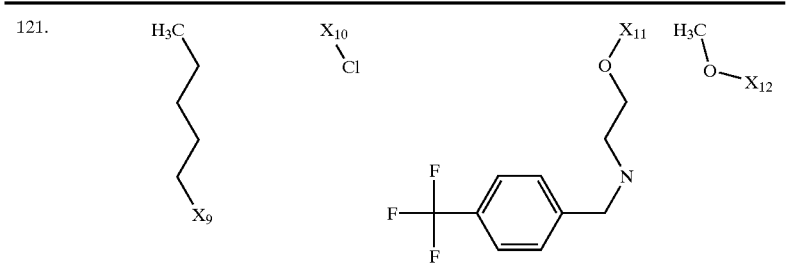 | | | |
| 122. | 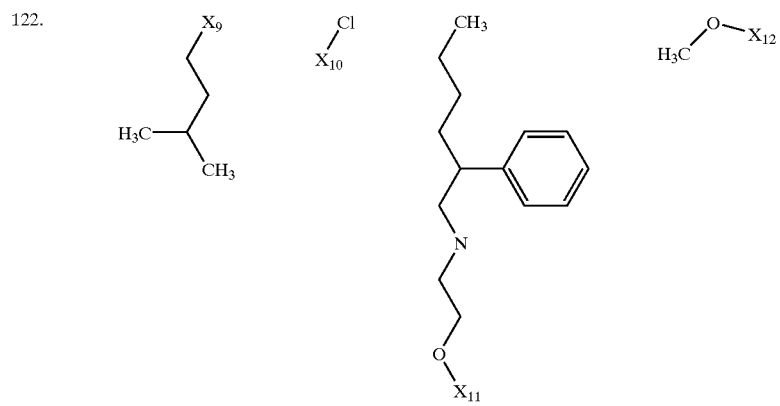 | | | |
| 123. | 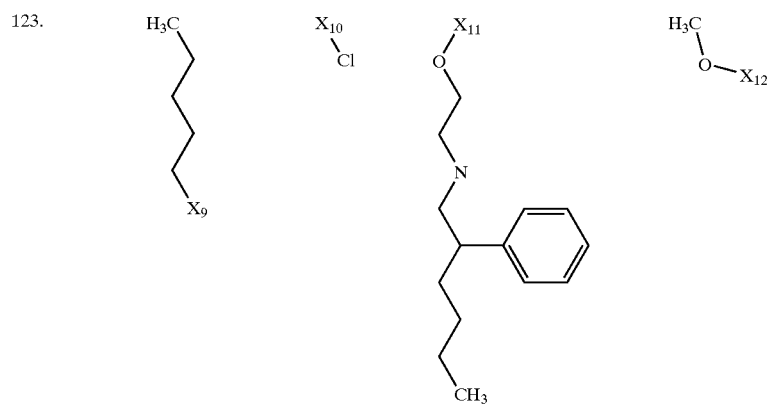 | | | |

-continued
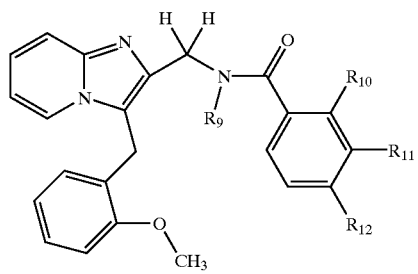
| Ex # | R9 | R10 | R11 | R12 |
|---|---|---|---|---|
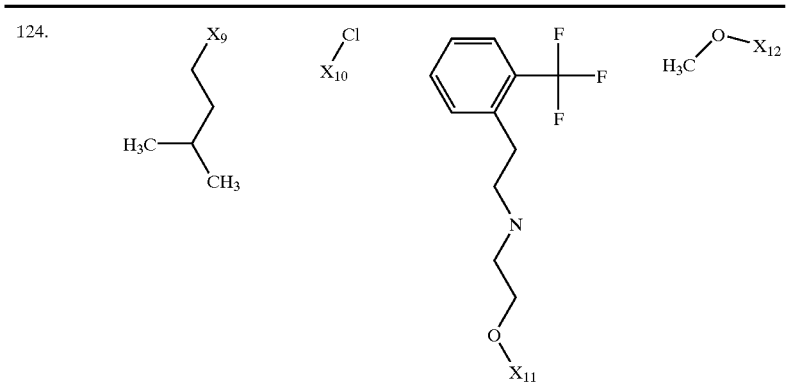
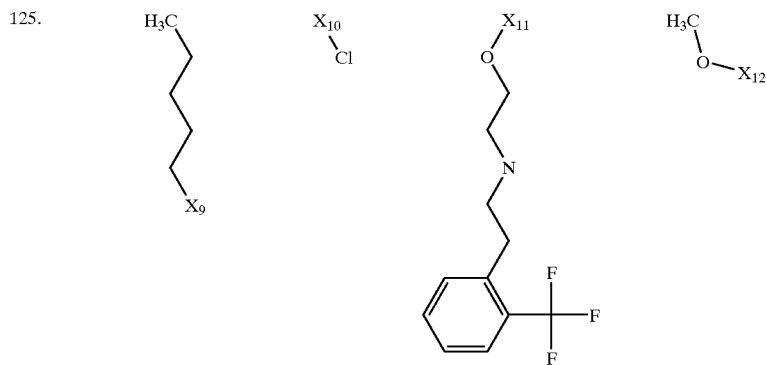
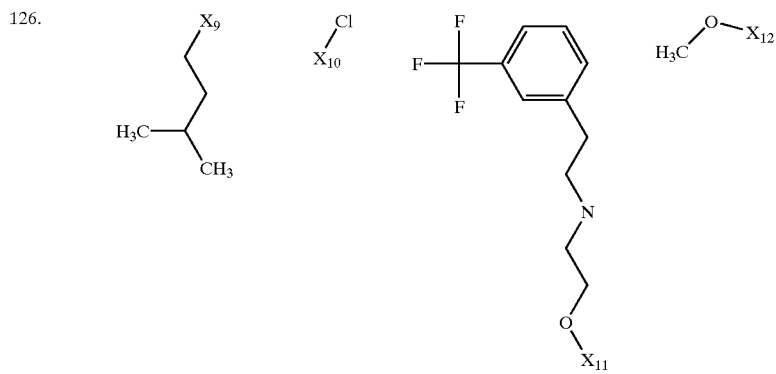

-continued
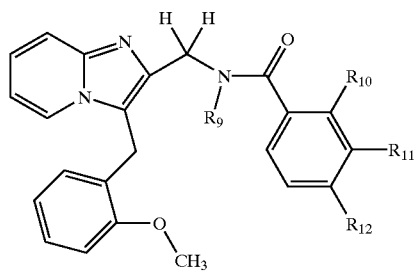
| Ex # | R9 | R10 | R11 | R12 |
|---|---|---|---|---|
| 127. | 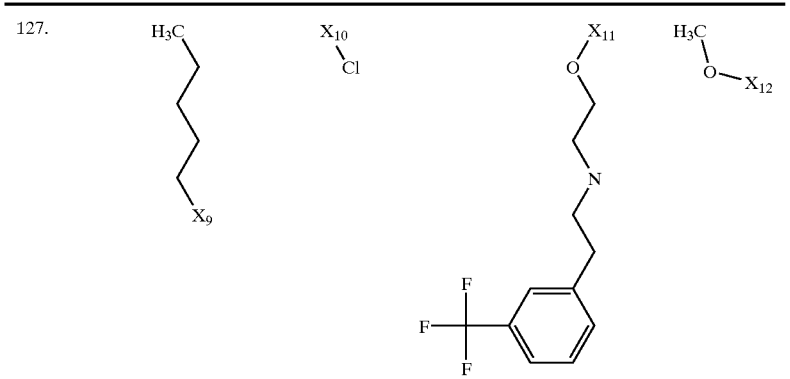 | | | |
| 128. | | | | |
| 129. | | | | |

-continued
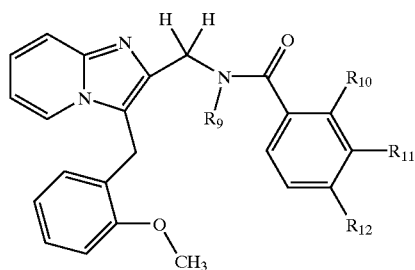
| Ex # | R9 | R10 | R11 | R12 |
|---|---|---|---|---|
| 130. | | | | |
| 131. | | | | |
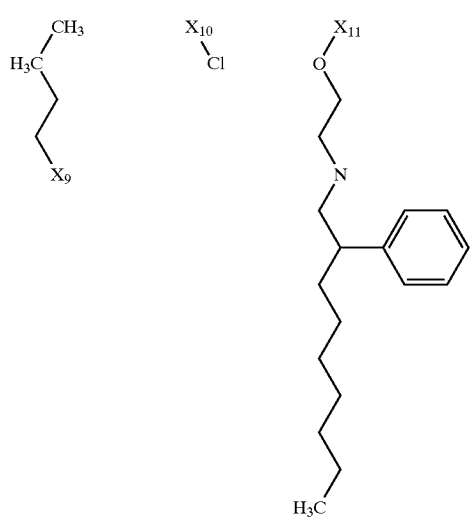
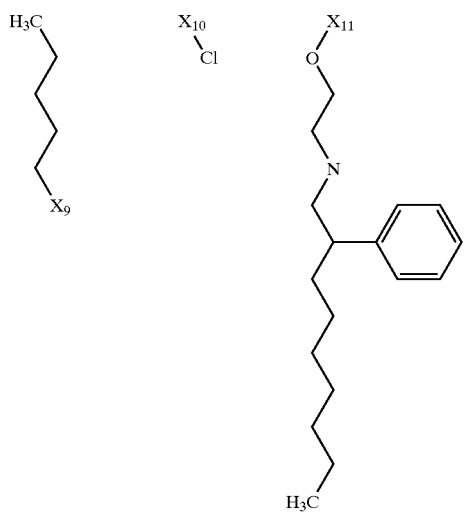

-continued
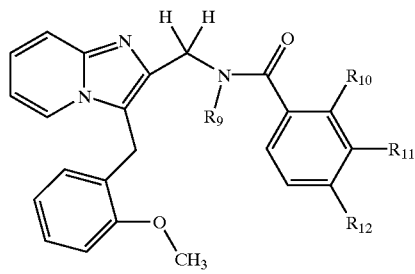
| Ex # | R9 | R10 | R11 | R12 |
|---|---|---|---|---|
| 132. | isobutyl-CH2CH2-X9 (H3C)2CHCH2CH2-X9 | Cl-X10 | (CH3)2N-CH2CH2-N(CH3)-CH2CH2-O-X11 | H3C-O-X12 |
| 133. | H3C-(CH2)4-X9 | X10-Cl | X11-O-CH2CH2-N-CH2CH2-N(CH3)2 | H3C-O-X12 |
| 134. | (H3C)2CHCH2CH2-X9 | Cl-X10 | (CH3)2N-CH2CH2CH2-N(CH3)-CH2CH2-O-X11 | H3C-O-X12 |

-continued
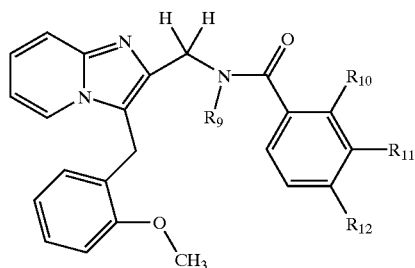
| Ex # | R9 | R10 | R11 | R12 |
|---|---|---|---|---|
| 135. | 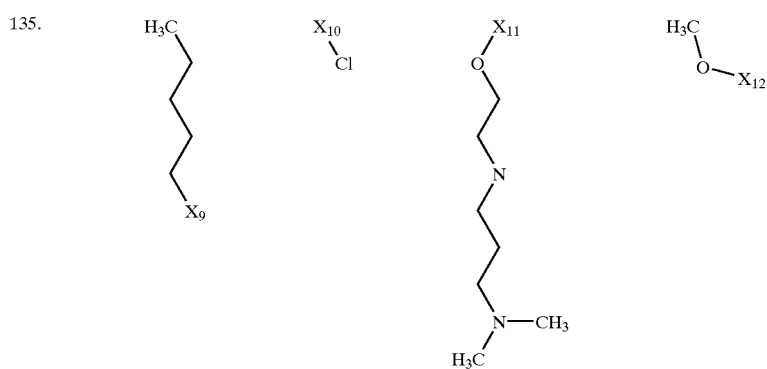 | | | |
| 136. | 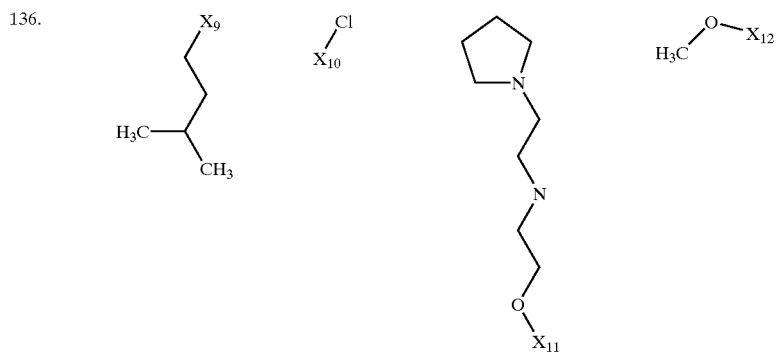 | | | |
| 137. | 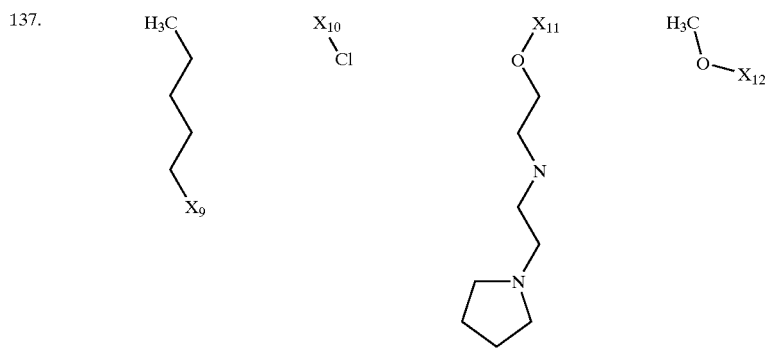 | | | |

-continued
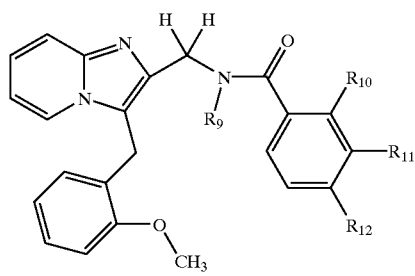
| Ex # | R9 | R10 | R11 | R12 |
|---|---|---|---|---|
| 138. | X9-CH2CH2-CH(CH3)-CH3 (isopentyl with X9) | Cl, X10 | H3C-CH2-N(CH2CH3)-CH2CH2-N-CH2CH2-O-X11 | H3C-O-X12 |
| 139. | H3C-CH2CH2CH2CH2-X9 (pentyl with X9) | X10, Cl | X11-O-CH2CH2-N-CH2CH2-N(CH2CH3)(CH2CH3) | H3C-O-X12 |
| 140. | X9-CH2CH2-CH(CH3)-CH3 (isopentyl with X9) | Cl, X10 | piperidinyl-CH2CH2-N-CH2CH2-O-X11 | H3C-O-X12 |

-continued
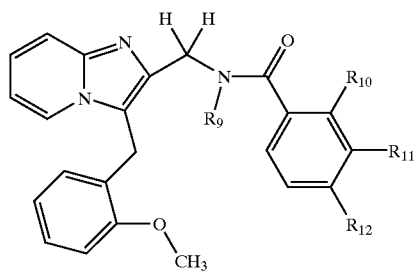
| Ex # | R9 | R10 | R11 | R12 |
|---|---|---|---|---|
| 141. | 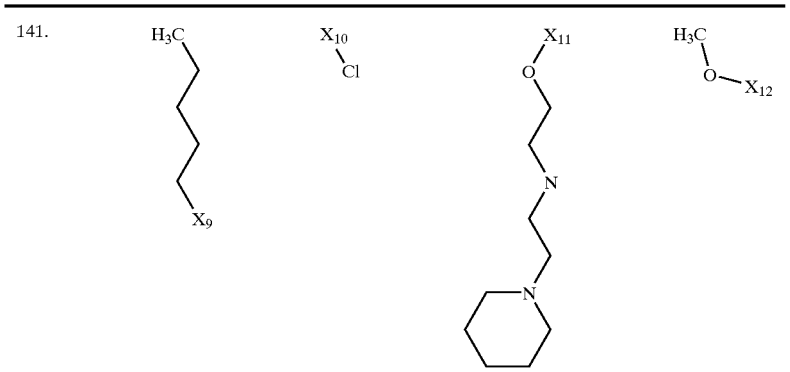 | | | |
| 142. | 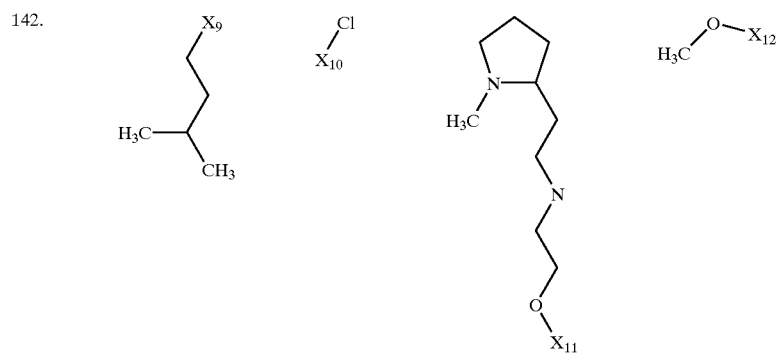 | | | |
| 143. | 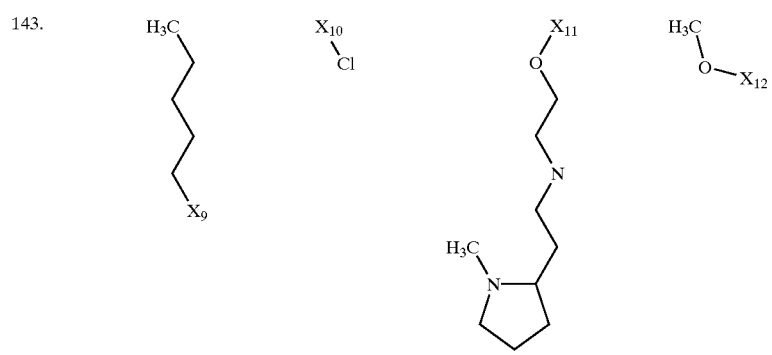 | | | |

-continued
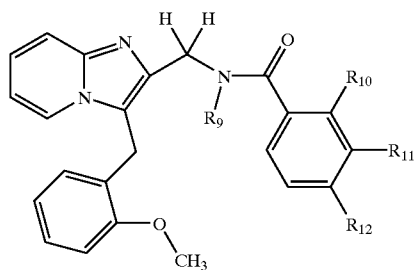
| Ex # | R9 | R10 | R11 | R12 |
|---|---|---|---|---|
| 144. | | | | |
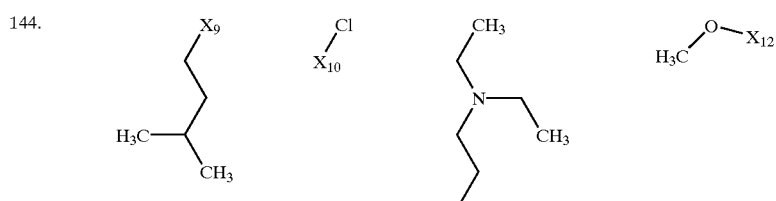
| 145. | | | | |
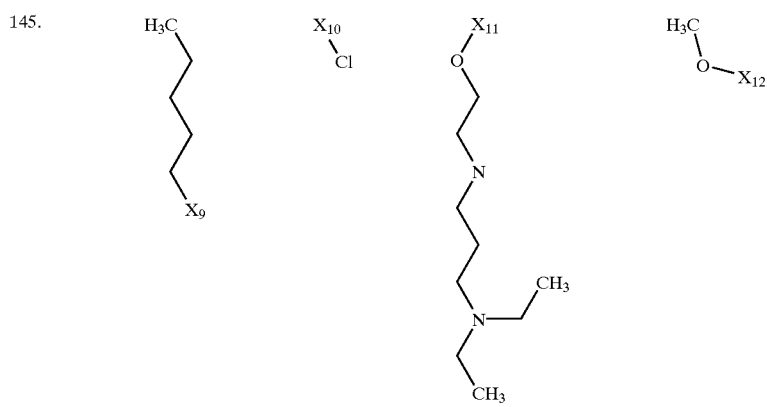
| 146. | | | | |
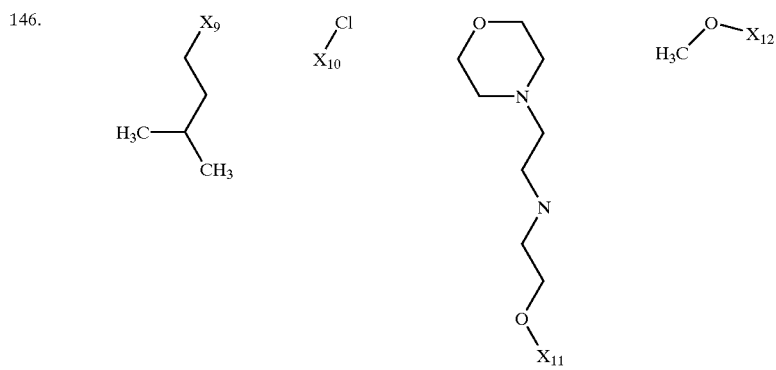

-continued
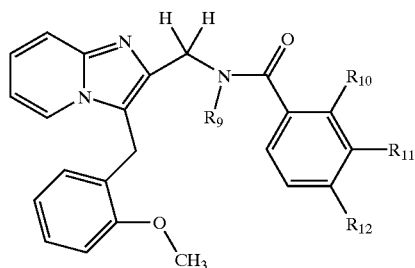
| Ex # | R9 | R10 | R11 | R12 |
|---|---|---|---|---|
| 147. | 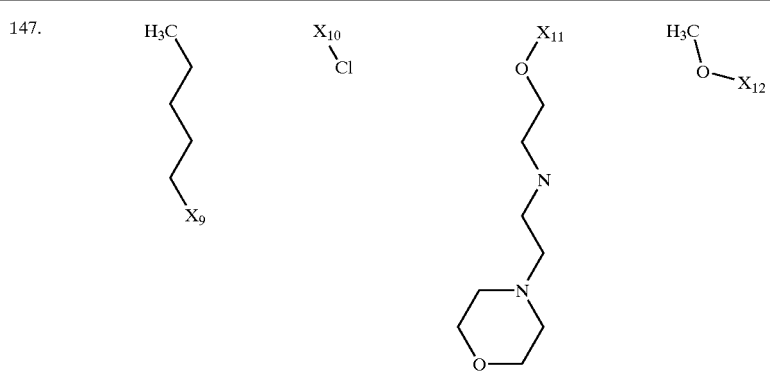 | | | |
| 148. | | | | |
| 149. | 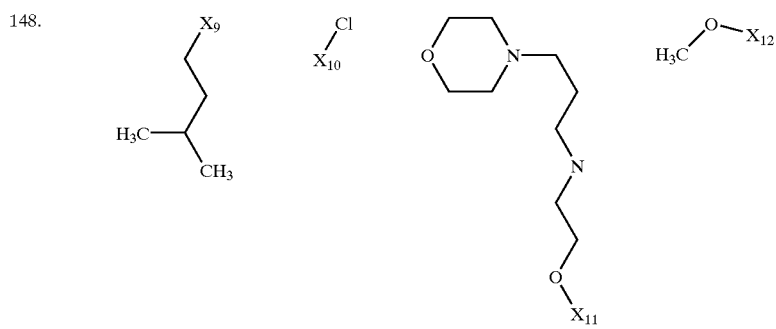 | | | |
| | 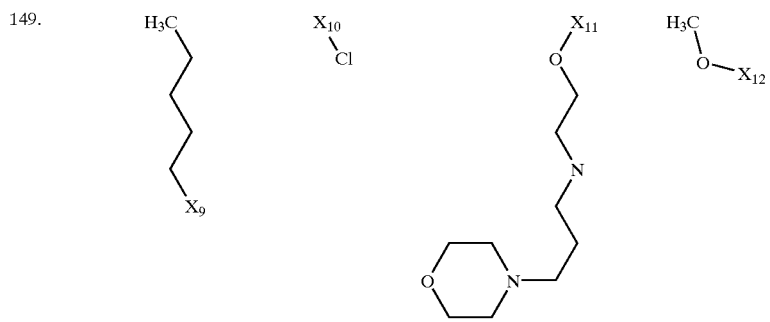 | | | |

-continued
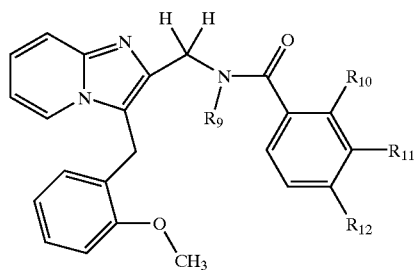
| Ex # | R9 | R10 | R11 | R12 |
|---|---|---|---|---|
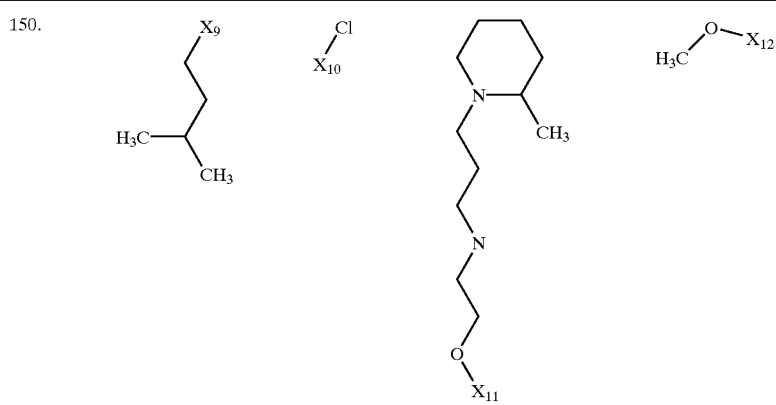
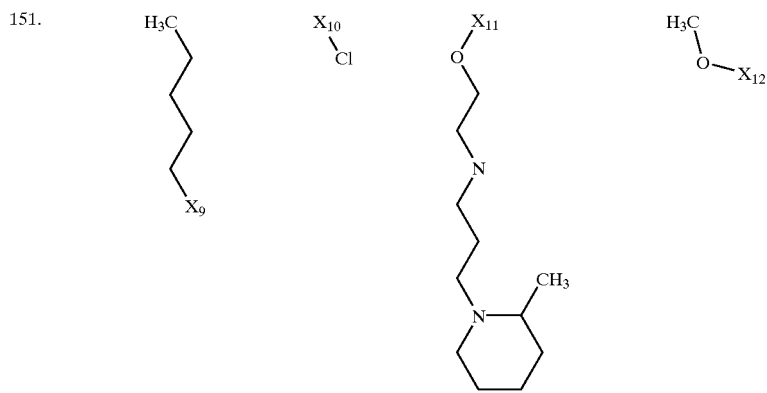
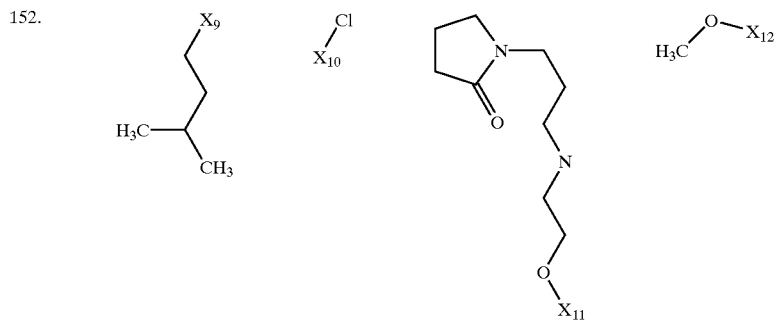

-continued
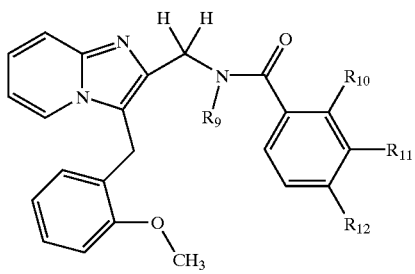
| Ex # | R9 | R10 | R11 | R12 |
|---|---|---|---|---|
| 153. | H₃C–(CH₂)₄–X₉ | X₁₀–Cl | X₁₁–O–CH₂CH₂–N(CH₂CH₂-(2-oxopyrrolidin-1-yl)) | H₃C–O–X₁₂ |
| 154. | X₉–CH₂CH₂–CH(CH₃)–CH₃ | Cl, X₁₀ | 2,5-dihydro-1H-pyrrol-1-yl–CH₂CH₂–O–X₁₁ | H₃C–O–X₁₂ |
| 155. | H₃C–(CH₂)₄–X₉ | X₁₀–Cl | 2,5-dihydro-1H-pyrrol-1-yl–CH₂CH₂–O–X₁₁ | H₃C–O–X₁₂ |
| 156. | X₉–CH₂CH₂–CH(CH₃)–CH₃ | Cl, X₁₀ | pyrrolidin-1-yl–CH₂CH₂–O–X₁₁ | H₃C–O–X₁₂ |
| 157. | H₃C–(CH₂)₄–X₉ | X₁₀–Cl | pyrrolidin-1-yl–CH₂CH₂–O–X₁₁ | H₃C–O–X₁₂ |

-continued
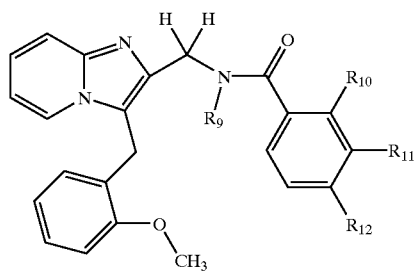
| Ex # | R9 | R10 | R11 | R12 |
|---|---|---|---|---|
| 158. | (CH3)2CHCH2CH2-X9 | Cl, X10 | tetrahydropyridinyl-CH2CH2-O-X11 | H3C-O-X12 |
| 159. | H3C-(CH2)4-X9 | X10, Cl | X11-O-CH2CH2-tetrahydropyridinyl | H3C-O-X12 |
| 160. | (CH3)2CHCH2CH2-X9 | Cl, X10 | piperidinyl-CH2CH2-O-X11 | H3C-O-X12 |
| 161. | H3C-(CH2)4-X9 | X10, Cl | X11-O-CH2CH2-piperidinyl | H3C-O-X12 |
| 162. | (CH3)2CHCH2CH2-X9 | Cl, X10 | morpholinyl-CH2CH2-O-X11 | H3C-O-X12 |
| 163. | H3C-(CH2)4-X9 | X10, Cl | X11-O-CH2CH2-morpholinyl | H3C-O-X12 |

-continued
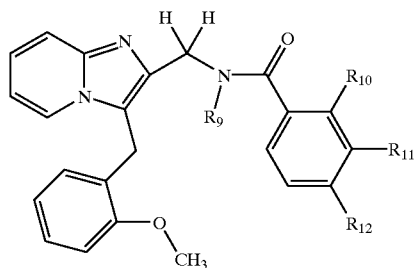
| Ex # | R9 | R10 | R11 | R12 |
|---|---|---|---|---|
| 164. | isopentyl-X9 (H3C, CH3 branched) | Cl, X10 | 4-methylpiperidin-1-yl-CH2CH2-O-X11 | H3C-O-X12 |
| 165. | H3C-(CH2)4-X9 | X10, Cl | X11-O-CH2CH2-N(4-methylpiperidine) | H3C-O-X12 |
| 166. | isopentyl-X9 | Cl, X10 | azepan-1-yl-CH2CH2-O-X11 | H3C-O-X12 |
| 167. | H3C-(CH2)4-X9 | X10, Cl | X11-O-CH2CH2-N(azepane) | H3C-O-X12 |
| 168. | isopentyl-X9 | Cl, X10 | thiomorpholin-4-yl-CH2CH2-O-X11 | H3C-O-X12 |
| 169. | H3C-(CH2)4-X9 | X10, Cl | X11-O-CH2CH2-N(thiomorpholine) | H3C-O-X12 |

-continued
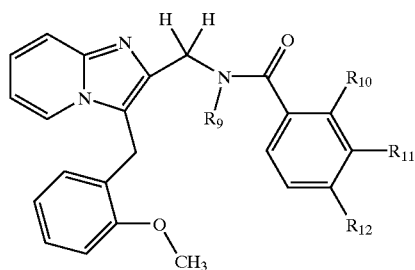
| Ex # | R9 | R10 | R11 | R12 |
|---|---|---|---|---|
| 170. | 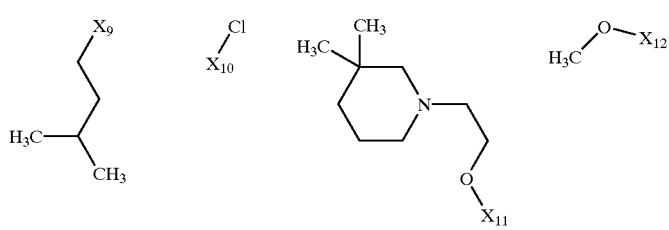 | | | |
| 171. | | | | |
| 172. | 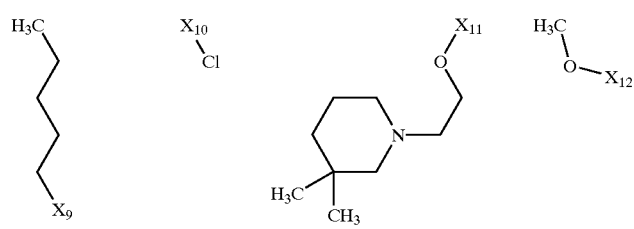 | | | |
| 173. | | | | |
| 174. | 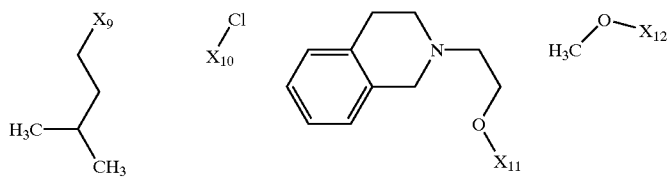 | | | |

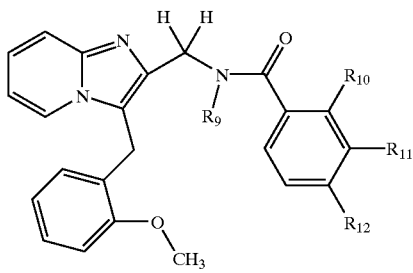

| Ex # | R9 | R10 | R11 | R12 |
|---|---|---|---|---|
| 175. | H$_3$C-$X_9$ | $X_{10}$-Cl | $X_{11}$-O-(tetrahydroisoquinoline-CH$_2$CH$_2$-N) | H$_3$C-O-$X_{12}$ |

Example 9

Ligand Binding Assay on Sf9 Cell Membranes Expressing the BK-2 Receptor

This assay is used to determine the high affinity of compounds of this invention for the BK-2 (bradykinin B$_2$) receptor.

Binding Buffer:

50 mM Tris, pH 7.0 (4° C.), 0.14 grams per liter bacitracin (approx. 50,000 units of activity/liter, lot# 103746 from Amersham), and 10$^{-6}$ M captopril. Captopril is purchased from Sigma C-4042, 2.17 mg in 10 ml of milli-Q water produces a 10$^{-3}$ M stock. Stock can be stored for 3 weeks in the refrigerator. 1.0 ml of stock per liter buffer=10$^{-6}$ M final concentration.

Ligand Preparation:

0.25 nM $^3$H-Bradykinin is used. 10 μl of stock+100 ml of binding buffer gives approximately 600 cpm/5 μl aliquot.

Non-Specific Preparation:

NS binding is defined by unlabeled bradykinin at 1 μM final concentration. Aliquots are stored at −20° C. in 0.5% BSA at a concentration of 10$^{-3}$ M. Aliquots are then diluted 1:100 for an intermediate concentration of 10$^{-5}$ M.

Baculovirus-infected Sf9 cells expressing recombinant human bradykinin B$_2$ receptors are harvested 48 hours post infection via centrifugation at 3000×g. Cells are washed with ice-cold PBS and stored at −70 ° C. until needed. Frozen cell pellets are resuspended in ice cold Washing Buffer (50 mM Tris pH 7.0) and homogenized via POLYTRON for 30 seconds at setting 5. Membranes are centrifuged at 40,000×g for 10 min. Pellets are resuspended in Washing Buffer with the aid of a polytron and centrifuged again. Membranes are resuspended in binding buffer at a concentration of 133 μg/ml. This corresponds to 20 μg of protein per 150 μl.

When measuring non-specific binding, incubations contain 150 μl of Sf9 cell membranes prepared as described above, 50 μl $^3$H-Bradykinin (0.25 nM), 25 UL unlabeled bradykinin at 1 μM final concentration and 2 μl DMSO. Incubations for determining test compound binding contain 175 μl of Sf9 cell membranes, 50 μl $^3$H-Bradykinin (0.25 nM), and test compound in 2 μl DMSO. The concentration of the test compound is generally 1 μM for displacement studies. The binding reaction components are incubated for 2 hrs at 4° C. in Falcon U bottom plates. Plates are harvested on the microbeta harvester onto 0.5% PEI pretreated unifilters. After harvesting, the filters are dried overnight. 17 μl of beta-scint is added to each well before the unifilters are counted in the microbeta counters. Data are collected in duplicate determinations, averaged and % inhibition of total specific binding is calculated. Total Specific Binding=Total-Nonspecific. In some cases, the amounts of unlabeled drug is varied and total displacement curves of binding are carried out. Data are converted to a form for the calculation of IC$_{50}$ and Hill Coefficient (nH). Ki's are subsequently determined by the Cheng-Prusoff equation (Cheng, Y. C.; Prusoff, W. C. Biochem. Pharmacol. 1972, 22, 3099–3108). In the described assay, preferred compounds of the invention have Ki's of less than 1 μM, more preferred compounds of the invention exhibit Ki values of less than 500 nM and most preferred compounds of the invention exhibit Ki values of less than 100 nM or less than 10 nM.

Example 10

BK-2 Receptor Mediated Calcium Mobilization

The agonist and antagonist properties of the compounds of the invention can be evaluated by the following assay.

CHO cells stably expressing the BK-2 receptor are grown in Ham's F-12 media supplemented with 250 μg/ml G418, 1 μg/ml tetracycline, 7 μg/ml puromycin, 10% fetal bovine serum and 25 mM Hepes, pH=7.4. Forty eight hours prior to assay, the cell growth media is replaced with another medium that does not contain the tetracycline. Twenty four hours prior to experiment sodium butyrate is added to a final concentration of 10 mM. On the day of assay, cells, grown to 70–90% confluency in 96-well plates, are washed with Krebs-Ringer buffer (25 mM HEPES, 5 mM KCl, 0.96 mM NaH$_2$PO$_4$, 1 mM MgSO$_4$, 2 mM CaCl$_2$, 5 mM glucose, and 1 mM probenecid, pH 7.4) and are then incubated for 1–2 hours in the above buffer supplemented with Fluo3-AM (2.5 n 10 (g/ml; Teflabs) at 37° C. in an environment containing 5% $CO_2$. The wells are then washed twice with Krebs-Ringers buffer. Agonist-induced (bradykinin) calcium mobilization is monitored using either Fluoroskan Ascent (Labsystems) or FLIPR (Molecular Devices) instruments. The agonists, either bradykinin or drug candidates, are added to the cells and fluorescence responses are continuously recorded for up to 5 min. For the examination of antagonist drug candidates, compounds, at a concentration of 1 μM in DMSO, are preincubated with the cells for up to 30 minutes prior to administration of the bradykinin agonist. Bradykinin agonist is generally applied at a concentration sufficient to induce 50% maximal activity. Responses are recorded for up to 5 min. Kaleidagraph software (Synergy Software, Reading, Pa.) is utilized to fit the data to the equation y=a*(1/(1+(b/x)c)) to determine the $EC_{50}$ value or $IC_{50}$ value for the response. In this equation, y is the maximum fluorescence signal, x is the concentration of the agonist or antagonist, a is the Emax, b corresponds to the $EC_{50}$ or $IC_{50}$ value, and, finally, c is the Hill coefficient.

Example 11

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; $SR_1$ International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 12

Use of Compounds of the Invention as Probes for BK-2 Receptors in Cultured Cells and Tissue Samples The presence of BK-2 receptors in cultured cells or tissue samples may be ascertained by the procedures described by Hall and Morton in the chapter entitled "Immunopharmacology of the Bradykinin Receptor" of The Handbook of Immunopharmacology—The Kinin Systems (1997) Academic Press, S. C. Farmer, editor, using radiolabeled compounds of the invention prepared as described in the preceding Example 9.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

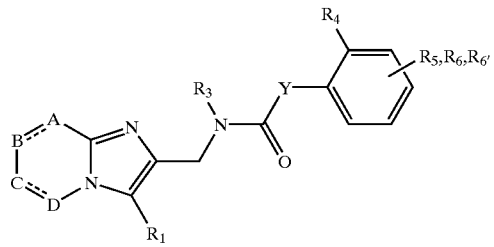

or the Pharmaceutically acceptable non-toxic salts thereof wherein:

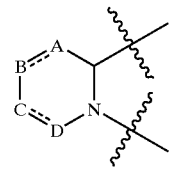

represents a nitrogen-containing ring system, in which the dashed lines represent double, single or aromatic bonds, and in which not more than two of A, B, C, or D represent nitrogen and remaining ring members are carbon, and which nitrogen-containing ring system is optionally substituted with up to four substituents independently selected from:
(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
(ii) $C_1$–$C_6$alkoxy$NR_7R_8$, $NR_7R_8$, $NR_7COR_8$, $CONR_7R_8$, wherein $R_7$ and $R_8$ are the same or different and represent hydrogen, or straight or branched chain lower alkyl, or $R_7$ and $R_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and
(iii) $O(CH_2)_nCO_2R_A$ (where n=1,2,3, or 4), $COR_A$, and $CO_2R_A$ wherein $R_A$ represents hydrogen, or straight or branched chain lower alkyl;

$R_1$ is arylalkyl, heteroarylalkyl, or allyl each of which is optionally substituted directly or through a $O(CH_2)_n$ linker (where n=1,2,3 or 4) with up to three substituents independently selected from:
(i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),

155

(ii) $C_1$–$C_6$alkoxyNR$_7$·R$_8$·, NR$_7$·R$_8$·, NR$_7$·COR$_8$·, CONR$_7$R$_8$·, wherein R$_7$· and R$_8$· are the same or different and represent hydrogen, or straight or branched chain lower alkyl, or R$_7$' and R$_8$' are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, (iii) O(CH$_2$)$_n$CO$_2$R$_{A'}$ (where n=1,2,3, or 4), COR$_{A'}$, CO$_2$R$_{A'}$, wherein R$_{A'}$ represents hydrogen, or straight or branched chain lower alkyl, (iv) SO$_2$R$_{A'}$, NHSO$_2$R$_{A'}$, SO$_2$NHR$_{A'}$, SO$_2$NHCOR$_{A'}$, CONHSO$_2$R$_{A'}$, wherein R$_{A'}$ is as defined above, (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy);

$R_3$ represents straight or branched chain lower alkyl;

$R_4$ represents halogen or trifluoromethyl;

$R_5$, $R_6$, and $R_{6'}$ are the same or different and represent (i) hydrogen, trifluoromethyl, trifluoromethoxy, nitro, cyano, lower alkyl, halogen, aminomethyl, mono or dialkylamino, mono or dialkylaminomethyl, wherein each alkyl is independently lower alkyl, or $C_1$–$C_6$alkoxyaminoalkyl where the amino is mono or disubstituted with straight or branched chain lower alkyl;

(ii) $C_1$–$C_6$ alkoxy (with the proviso that $R_5$, $R_6$, or $R_{6'}$ may not be $C_1$–$C_6$ alkoxy when located ortho to Y) which is optionally substituted with (a) $C_1$–$C_6$ alkoxy, $C_1$–$C_6$ alkylthio, amino, hydroxy, halogen, haloalkyl, mono or di($C_1$–$C_6$) alkylamino, morpholino, pyrrolidino, piperidino, or thiomorpholino (b) mono or di($C_1$–$C_{10}$)alkylamino$_1$, wherein said mono or di($C_1$–$C_{10}$)alkylamino$_1$ is substituted with aryl, arylalkyl, heteroarylalkyl, heteroarylalkyl, $C_3$–$C_7$ cycloalkyl, ($C_3$–$C_7$ cycloalkyl)$C_1$–$C_4$alkyl, $C_3$–$C_7$heterocycloalkyl, or ($C_3$–$C_7$ cycloalkyl)$C_1$–$C_4$alkyl wherein each aryl, heteroaryl, cycloalkyl, or heterocycloalkyl group substituting said mono or di($C_1$–$C_{10}$) alkylamino, is optionally substituted by alkyl, oxo, halogen, hydroxyl, trifluoromethyl, triflurometoxy, or alkoxy; or $R_4$ and $R_5$ are joined to form a 5, 6, or 7 membered carbocyclic or heterocyclic aromatic ring which is optionally substituted with up to four substitutents selected from:

(i) halogen, nitro, trifluoromethyl, cyano, hydroxyl, $C_1$–$C_6$ alkyl, amino, $C_1$–$C_6$ alkoxy, aminomethyl, mono or dialkylamino, mono or dialkylaminomethyl (wherein each alkyl is independently lower alkyl), (ii) $C_1$–$C_6$alkoxyNR$_7$"R$_8$", NR$_7$"R$_8$", CONR$_7$"R$_8$", NR$_7$"COR$_8$", where R$_7$" and R$_8$" are the same or different and represent hydrogen or straight or branched chain lower alkyl, or R$_7$" and R$_8$" may be a 5, 6, or 7 membered heterocyclic ring, which is optionally substituted with halogen, nitro, trifluoromethyl, cyano, hydroxyl, lower alkyl, amino, mono or dialkylamino (wherein each alkyl is independently lower alkyl) or $C_1$–$C_6$ alkoxy, (iii) O(CH$_2$)$_n$CO$_2$R$_A$" where n=1,2,3,4, COR$_A$", or CO$_2$R$_A$" where R$_A$" represents hydrogen or straight or branched chain lower alkyl having 1–6 carbon atoms;

156 and $R_6$ and $R_{6'}$ are as defined above; and

Y represents a bond or CH$_2$, when Y=CH$_2$ it may be mono or disubstituted with a straight or branched chain lower alkyl, or straight or branched chain lower alkoxy having 1–6 carbon atoms.

2. A compound of the formula:

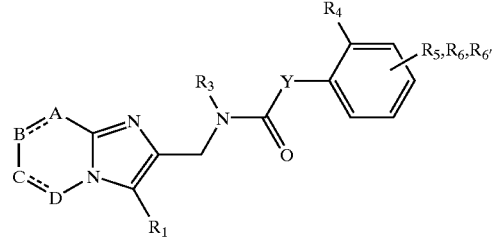

or the pharmaceutically acceptable non-toxic salts thereof wherein:

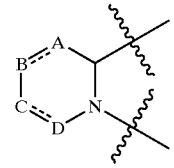

represents a nitrogen-containing ring system, in which the dashed lines represent double, single or aromatic bonds, and in which not more than two of A, B, C, or D represents nitrogen and remaining ring members are carbon, and which nitrogen-containing ring system is optionally substituted with up to four substituents independently selected from:

(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl), (ii) $C_1$–$C_6$alkoxyNR$_7$R$_8$, NR$_7$R$_8$, NR$_7$COR$_8$, CONR$_7$R$_8$, wherein R$_7$ and R$_8$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and (iii) O(CH$_2$)$_n$CO$_2$R$_A$ (where n=1,2,3, or 4), COR$_A$, and CO$_2$R$_A$ wherein R$_A$ represents hydrogen, or straight or branched chain lower alkyl;

$R_1$ is benzyl which is optionally substituted directly or through a O(CH$_2$)$_n$ linker (where n=1,2,3 or 4) with up to three substituents independently selected from: $C_1$–$C_6$alkoxyNR$_7$·R$_8$·, NR$_7$·R$_8$·, NR$_7$·COR$_8$·, CONR$_7$R$_8$·, (i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl), (ii) $C_1$–$C_6$alkoxyNR$_7$·R$_8$·, NR$_7$·R$_8$·, NR$_7$·COR$_8$·, CONR$_7$·R$_8$·, wherein R$_7$· and R$_8$· are the same or different and represent hydrogen, or straight or branched chain lower alkyl, or $R_7{'}$ and $R_8{'}$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, (iii) $O(CH_2)_nCO_2R_{A'}$ (where n=1,2,3, or 4), $COR_{A'}$, $CO_2R_{A'}$, wherein $R_{A'}$ represents hydrogen, or straight or branched chain lower alkyl, (iv) $SO_2R_{A'}$, $NHSO_2R_{A'}$, $SO_2NHR_{A'}$, $SO_2NHCOR_{A'}$, $CONHSO_2R_{A'}$, wherein $R_{A'}$ is as defined above, (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy);

$R_3$ represents straight or branched chain lower alkyl;

$R_4$ represents halogen or trifluoromethyl;

$R_5$, $R_6$, and $R_{6'}$ are the same or different and represent
(i) hydrogen, trifluoromethyl, trifluoromethoxy, nitro, cyano, lower alkyl, halogen, aminomethyl, mono or dialkylamino, mono or dialkylaminomethyl, wherein each alkyl is independently lower alkyl, or $C_1$–$C_6$alkoxyaminoalkyl where the amino is mono or disubstituted with straight or branched chain lower alkyl;

(ii) $C_1$–$C_6$ alkoxy (with the proviso that $R_5$, $R_6$, or $R_{6'}$ may not be $C_1$–$C_6$ alkoxy when located ortho to Y) which is optionally substituted with (a) $C_1$–$C_6$ alkoxy, $C_1$–$C_6$ alkylthio, amino, hydroxy, halogen, haloalkyl, mono or di($C_1$–$C_6$) alkylamino, morpholino, pyrrolidino, piperidino, or thiomorpholino (b) mono or di($C_1$–$C_{10}$)alkylamino$_1$, wherein said mono or di($C_1$–$C_{10}$)alkylamino$_1$ is substituted with aryl, arylalkyl, heteroarylalkyl, heteroarylalkyl, $C_3$–$C_7$ cycloalkyl, ($C_3$–$C_7$ cycloalkyl)$C_1$–$C_4$alkyl, $C_3$–$C_7$heterocycloalkyl, or ($C_3$–$C_7$ cycloalkyl)$C_1$–$C_4$alkyl wherein each aryl, heteroaryl, cycloalkyl, or heterocycloalkyl group substituting said mono or di($C_1$–$C_{10}$) alkylamino, is optionally substituted by alkyl, oxo, halogen, hydroxyl, trifluoromethyl, trifluoromethoxy, or alkoxy; and Y represents a bond or $CH_2$, when $Y=CH_2$ it may be mono or disubstituted with a straight or branched chain lower alkyl, or straight or branched chain lower alkoxy having 1–6 carbon atoms.

3. A compound of the formula:

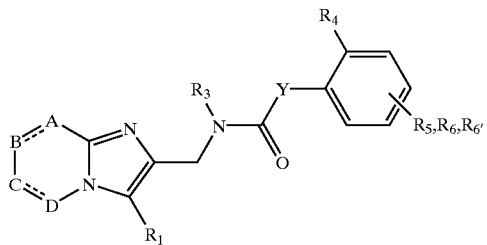

or the pharmaceutically acceptable non-toxic salts thereof wherein:

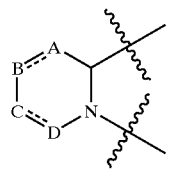

represents a nitrogen-containing ring system, in which not more than two of A, B, C, or D represent nitrogen and remaining ring members are carbon, and which nitrogen-containing ring system is optionally substituted with up to four substituents independently selected from:

(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl), (ii) $C_1$–$C_6$alkoxyNR$_7$R$_8$, NR$_7$R$_8$, NR$_7$COR$_8$, CONR$_7$R$_8$, wherein $R_7$ and $R_8$ are the same or different and represent hydrogen, or straight or branched chain lower alkyl, or $R_7$ and $R_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and (iii) $O(CH_2)_nCO_2R_A$ (where n=1,2,3, or 4), $COR_A$, and $CO_2R_A$ wherein $R_A$ represents hydrogen, or straight or branched chain lower alkyl;

$R_1$ is allyl, or 2, 3, or 4 picolyl which is optionally substituted with up to three substituents independently selected from:

(i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl), (ii) $C_1$–$C_6$alkoxyNR$_{7'}$R$_{8'}$, NR$_{7'}$R$_{8'}$, NR$_{7'}$COR$_{8'}$, CONR$_7$R$_{8'}$, wherein $R_{7'}$ and $R_{8'}$ are the same or different and represent hydrogen, or straight or branched chain lower alkyl, or $R_{7'}$ and $R_{8'}$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, (iii) $O(CH_2)_nCO_2R_{A'}$ (where n=1,2,3, or 4), $COR_{A'}$, $CO_2R_{A'}$, wherein $R_{A'}$ represents hydrogen, or straight or branched chain lower alkyl, (iv) $SO_2R_{A'}$, $NHSO_2R_{A'}$, $SO_2NHR_{A'}$, $SO_2NHCOR_{A'}$, $CONHSO_2R_{A'}$, wherein $R_{A'}$ is as defined above, (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy) ;$R_3$ represents straight or branched chain lower alkyl;

$R_4$ represents halogen or trifluoromethyl;

(i) hydrogen, trifluoromethyl, trifluoromethoxy, nitro, cyano, lower alkyl, halogen, aminomethyl, mono or dialkylamino, mono or dialkylaminomethyl, wherein each alkyl is independently lower alkyl, or $C_1$–$C_6$alkoxyaminoalkyl where the amino is mono or disubstituted with straight or branched chain lower alkyl;

(ii) $C_1$–$C_6$ alkoxy (with the proviso that $R_5$, $R_6$, or $R_{6'}$ may not be $C_1$–$C_6$ alkoxy when located ortho to Y) which is optionally substituted with
  (a) $C_1$–$C_6$ alkoxy, $C_1$–$C_6$ alkylthio, amino, hydroxy, halogen, haloalkyl, mono or di($C_1$–$C_6$) alkylamino, morpholino, or thiomorpholino
  (b) mono or di($C_1$–$C_{10}$)alkylamino$_1$, wherein said mono or di($C_1$–$C_{10}$)alkylamino$_1$ is substituted with aryl, arylalkyl, heteroarylalkyl, heteroarylalkyl, $C_3$–$C_7$ cycloalkyl, ($C_3$–$C_7$ cycloalkyl)$C_1$–$C_4$alkyl, $C_3$–$C_7$heterocycloalkyl, ($C_3$–$C_7$ cycloalkyl)$C_1$–$C_4$alkyl wherein each aryl, heteroaryl, cycloalkyl, or heterocycloalkyl group substituting said mono or di($C_1$–$C_{10}$)alkylamino$_1$ is optionally substituted by alkyl, oxo, halogen, hydroxyl, trifluoromethyl, trifluromethoxy, or alkoxy; and Y represents a bond or $CH_2$, when Y=$CH_2$ it may be mono or disubstituted with a straight or branched chain lower alkyl, or straight or branched chain lower alkoxy having 1–6 carbon atoms.

4. A compound of the formula:

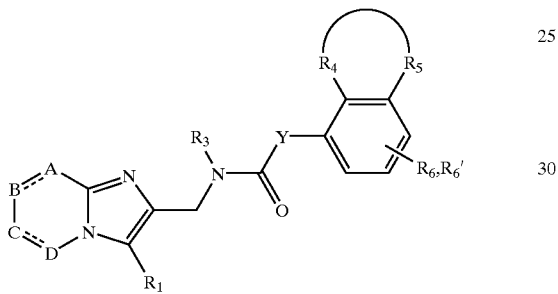

or the pharmaceutically acceptable non-toxic salts thereof wherein:

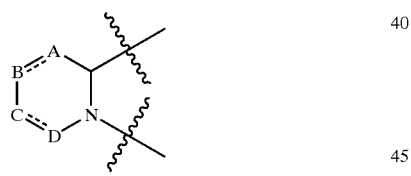

represents a nitrogen-containing ring system, in which not more than two of A, B, C, or D represent nitrogen and remaining ring members are carbon, and which nitrogen-containing ring system is optionally substituted with up to four substituents independently selected from:
  (i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyNR$_7$R$_8$, NR$_7$R$_8$, NR$_7$COR$_8$, CONR$_7$R$_8$, wherein R$_7$ and R$_8$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and
  (iii) O(CH$_2$)$_n$CO$_2$R$_A$ (where n=1,2,3, or 4), COR$_A$, and CO$_2$R$_A$ wherein R$_A$ represents hydrogen, or straight or branched chain lower alkyl;

$R_1$ is benzyl which is optionally substituted directly or through a O(CH$_2$)$_n$ linker (where n=1,2, 3 or 4) with up to three substituents independently selected from:
  (i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyNR$_{7'}$R$_{8'}$, NR$_{7'}$R$_{8'}$, NR$_{7'}$COR$_{8'}$, CONR$_{7'}$R$_{8'}$, wherein R$_{7'}$ and R$_{8'}$ are the same or different and represent hydrogen, or straight or branched chain lower alkyl, or R$_{7'}$ and R$_{8'}$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
  (iii) O(CH$_2$)$_n$CO$_2$R$_{A'}$ (where n=1,2,3, or 4), COR$_{A'}$, CO$_2$R$_{A'}$, wherein R$_{A'}$ represents hydrogen, or straight or branched chain lower alkyl,
  (iv) SO$_2$R$_{A'}$, NHSO$_2$R$_{A'}$, SO$_2$NHR$_{A'}$, SO$_2$NHCOR$_{A'}$, CONHSO$_2$R$_{A'}$, wherein R$_{A'}$ is as defined above,
  (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy);

$R_4$ and $R_5$ are joined to form a 5, 6, or 7 membered carbocyclic or heterocyclic aromatic ring which is optionally substituted with up to four substitutents selected from:
  (i) halogen, nitro, trifluoromethyl, cyano, hydroxyl, $C_1$–$C_6$ alkyl, amino, $C_1$–$C_6$ alkoxy, aminomethyl, mono or dialkylamino, mono or dialkylaminomethyl (wherein each alkyl is independently lower alkyl),
  (ii) $C_1$–$C_6$alkoxyNR$_7''$R$_8''$, NR$_7''$R$_8''$, CONR$_7''$R$_8''$, NR$_7''$COR$_8''$, where R$_7''$ and R$_8''$ are the same or different and represent hydrogen or straight or branched chain lower alkyl, or R$_7''$ and R$_8''$ may be a 5, 6, or 7 membered heterocyclic ring, which is optionally substituted with halogen, nitro, trifluoromethyl, cyano, hydroxyl, lower alkyl, amino, mono or dialkylamino (wherein each alkyl is independently lower alkyl) or $C_1$–$C_6$ alkoxy,
  (iii) O(CH$_2$)$_n$CO$_2$R$_A''$(where n=1,2,3,4), COR$_A''$, or CO$_2$R$_A''$ where R$_A''$ represents hydrogen or straight or branched chain lower alkyl having 1–6 carbon atoms;

$R_6$, and $R_{6'}$ are the same or different and represent: hydrogen, halogen, trifluoromethyl, trifluoromethoxy, nitro, cyano, lower alkyl, $C_1$–$C_6$ alkoxy (with the proviso that $R_6$ or $R_{6'}$ may not be $C_1$–$C_6$ alkoxy when located ortho to Y), aminomethyl, mono or dialkylamino, mono or dialkylaminomethyl, wherein each alkyl is independently a straight or branched chain lower alkyl, or $C_1$–$C_6$alkoxyaminoalkyl where the amino is mono or disubstituted with straight or branched chain lower alkyl; and Y represents a bond or CH$_2$, when Y=CH$_2$ it may be mono or disubstituted with a straight or branched chain lower alkyl, or straight or branched chain lower alkoxy having 1–6 carbon atoms.

5. A compound of the formula:

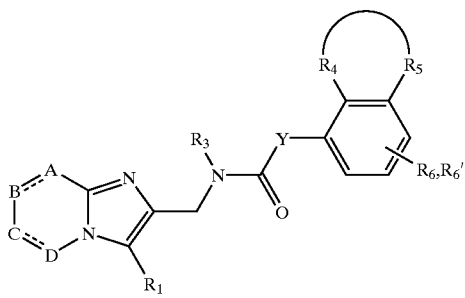

or the pharmaceutically acceptable non-toxic salts thereof wherein:

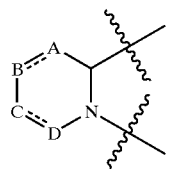

represents a nitrogen-containing ring system, in which not more than two of A, B, C, or D represent nitrogen and remaining ring members are carbon, and which nitrogen-containing ring system is optionally substituted with up to four substituents independently selected from:
  (i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyNR$_7$R$_8$, NR$_7$R$_8$, NR$_7$COR$_8$, CONR$_7$R$_8$, wherein R$_7$ and R$_8$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, and
  (iii) O(CH$_2$)$_n$CO$_2$R$_A$ (where n=1,2,3, or 4), COR$_A$, and CO$_2$R$_A$ wherein R$_A$ represents hydrogen, or straight or branched chain lower alkyl;

$R_1$ is allyl, or 2,3, or 4 picolyl which is optionally substituted with up to three substituents independently selected from:
  (i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
  (ii) $C_1$–$C_6$alkoxyNR$_7$'R$_8$', NR$_7$'R$_8$', NR$_7$'COR$_8$', CONR$_7$'R$_8$', wherein R$_7$' and R$_8$' are the same or different and represent hydrogen, or straight or branched chain lower alkyl, or R$_7$' and R$_8$' are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
  (iii) O(CH$_2$)$_n$CO$_2$R$_A$' (where n=1,2,3, or 4), COR$_A$', CO$_2$R$_A$', wherein R$_A$' represents hydrogen, or straight or branched chain lower alkyl,
  (iv) SO$_2$R$_A$', NHSO$_2$R$_A$', SO$_2$NHR$_A$', SO$_2$NHCOR$_A$', CONHSO$_2$R$_A$', wherein R$_A$' is as defined above,
  (v) tetrazole, triazole, imidazole, thiazole, oxazole, thiophene, naphthyl, and pyridyl (each of which may be optionally substituted with halogen, hydroxyl, amino, nitro, cyano, $C_1$–$C_6$ alkyl, and $C_1$–$C_6$ alkoxy)
  ;$R_3$ represents straight or branched chain lower alkyl;

$R_3$ represents straight or branched chain lower alkyl;

$R_4$ and $R_5$ form a 5, 6, or 7 membered carbocyclic or heterocyclic aromatic ring which is optionally substituted with up to four substituents independently selected from:
  (i) halogen, nitro, trifluoromethyl, cyano, hydroxyl, $C_1$–$C_6$ alkyl, amino, $C_1$–$C_6$ alkoxy, aminomethyl, mono or dialkylamino, mono or dialkylaminomethyl (wherein each alkyl is independently lower alkyl),
  (ii) $C_1$–$C_6$alkoxyNR$_7$"R$_8$", NR$_7$"R$_8$", CONR$_7$"R$_8$", NR$_7$"COR$_8$", where R$_7$" and R$_8$" are the same or different and represent hydrogen or straight or branched chain lower alkyl, or R$_7$" and R$_8$" may be a 5, 6, or 7 membered heterocyclic ring, which is optionally substituted with halogen, nitro, trifluoromethyl, cyano, hydroxyl, lower alkyl, amino, mono or dialkylamino (wherein each alkyl is independently lower alkyl) or $C_1$–$C_6$ alkoxy,
  (iii) O(CH$_2$)$_n$CO$_2$R$_A$" where n=1,2,3,4, COR$_A$", or CO$_2$R$_A$" where R$_A$" represents hydrogen or straight or branched chain lower alkyl having 1–6 carbon atoms $R_6$, and $R_6$' are the same or different and represent: hydrogen, halogen, trifluoromethyl, trifluoromethoxy, nitro, cyano, lower alkyl, $C_1$–$C_6$ alkoxy (with the proviso that $R_6$ or $R_6$' may not be $C_1$–$C_6$ alkoxy when located ortho to Y), aminomethyl, mono or dialkylamino, mono or dialkylaminomethyl, wherein each alkyl is independently a straight or branched chain lower alkyl, or $C_1$–$C_6$alkoxyaminoalkyl where the amino is mono or disubstituted with straight or branched chain lower alkyl; and Y represents a bond or CH$_2$, when Y=CH$_2$ it may be mono or disubstituted with a straight or branched chain lower alkyl, or straight or branched chain lower alkoxy having 1–6 carbon atoms.

6. A compound according to claim 2 of the formula:

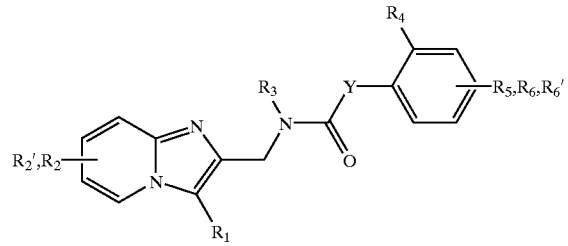

wherein $R_1$, $R_3$, $R_4$, $R_5$, $R_6$, $R_6$', and Y are as defined in claim 2 and $R_2$ and $R_2$' are independently selected from:
  (i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl), (iii) $C_1$–$C_6$alkoxyNR$_7$R$_8$, NR$_7$R$_8$, NR$_7$COR$_8$, CONR$_7$R$_8$, wherein R$_7$ and R$_8$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, (iii) O(CH$_2$)$_n$CO$_2$R$_A$ (where n=1,2,3, or 4), COR$_A$, and CO$_2$R$_A$; and wherein R$_A$ represents hydrogen, or straight or branched chain lower alkyl.

7. A compound according to claim 3 of the formula:

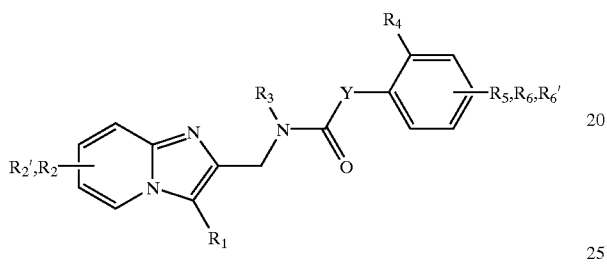

wherein R$_1$, R$_3$, R$_4$, R$_5$, R$_6$, R$_6$', and Y are as defined in claim 3 and R$_2$ and R$_2$' are independently selected from:
(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
(ii) $C_1$–$C_6$alkoxyNR$_7$R$_8$, NR$_7$R$_8$, NR$_7$COR$_8$, CONR$_7$R$_8$, wherein R$_7$ and R$_9$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
(iii) O(CH$_2$)$_n$CO$_2$R$_A$ (where n=1,2,3, or 4), COR$_A$, and CO$_2$R$_A$; and wherein R$_A$ represents hydrogen, or straight or branched chain lower alkyl.

8. A compound according to claim 4 of the formula:

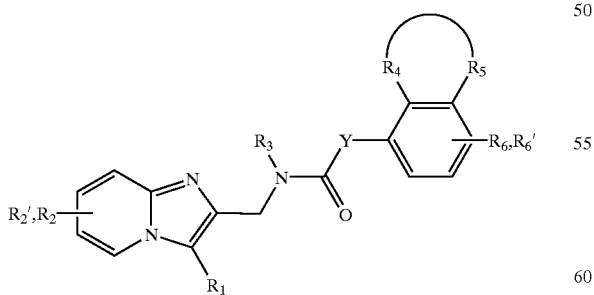

wherein R$_1$, R$_3$, R$_4$, R$_5$, R$_6$, R$_6$', and Y are as defined in claim 4 and R$_2$ and R$_2$' are independently selected from:
(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
(ii) $C_1$–$C_6$alkoxyNR$_7$R$_8$, NR$_7$R$_8$, NR$_7$COR$_8$, CONR$_7$R$_8$, wherein R$_7$ and R$_8$ are the same or different and represent hydrogen, or straight or branched chain lower alkyl, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
(iii) O(CH$_2$)$_n$CO$_2$R$_A$ (where n=1,2,3, or 4), COR$_A$, and CO$_2$R$_A$; and wherein R$_A$ represents hydrogen, or straight or branched chain lower alkyl.

9. A compound according to claim 5 of the formula:

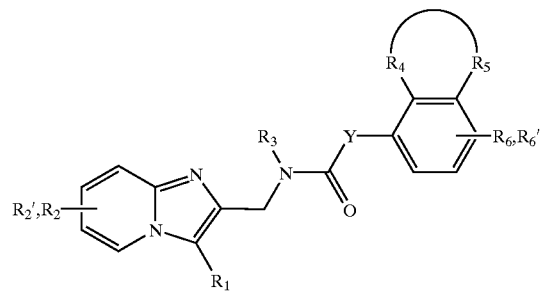

wherein R$_1$, R$_3$, R$_4$, R$_5$, R$_6$, R$_6$', and Y are as defined in claim 5 and R$_2$ and R$_2$' are independently selected from:
(i) hydroxyl, halogen, trifluoromethyl, $C_1$–$C_6$ alkyl, trifluoromethoxy, $C_1$–$C_6$ alkoxy, aminomethyl, mono or di($C_1$–$C_6$)alkylamino, mono or dialkylaminomethyl (wherein each alkyl is independently lower $C_1$–$C_6$ alkyl),
(ii) $C_1$–$C_6$alkoxyNR$_7$R$_8$, NR$_7$R$_8$, NR$_7$COR$_8$, CONR$_7$R$_8$ wherein R$_7$ and R$_8$ are the same or different and represent hydrogen, or straight or branched chain lower alky, or R$_7$ and R$_8$ are joined together to form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy,
(iii) O(CH$_2$)$_n$CO$_2$R$_A$ (where n=1,2,3, or 4), COR$_A$, and CO$_2$R$_A$; and wherein R$_A$ represents hydrogen, or straight or branched chain lower alkyl.

10. A compound according to claim 2 of the formula:

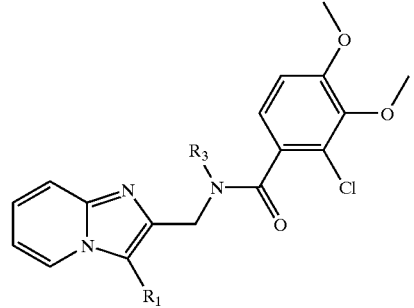

wherein R$_1$ and R$_3$ are as defined in claim 2.

11. A compound according to claim 10 wherein $R_3$ is isoamyl or n-pentyl.

12. A compound according to claim 3 of the formula:

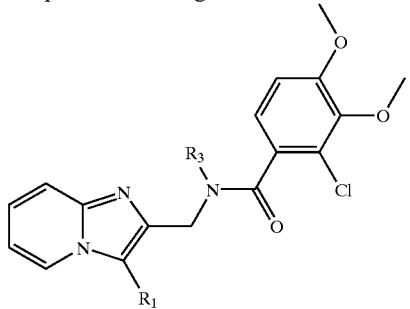

wherein $R_1$ and $R_3$ are as defined in claim 3.

13. A compound according to claim 12 wherein $R_3$ is isoamyl or n-pentyl.

14. A compound according to claim 2 of the formula:

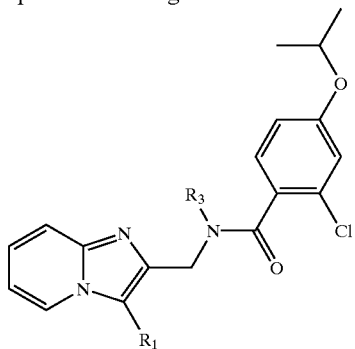

wherein $R_1$ and $R_3$ are as defined in claim 2.

15. A compound according to claim 14 wherein $R_3$ is isoamyl or n-pentyl.

16. A compound according to claim 3 of the formula:

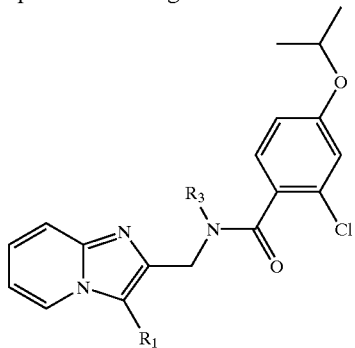

wherein $R_1$ and $R_3$ are as defined in claim 3.

17. A compound according to claim 16 wherein $R_3$ is isoamyl or n-pentyl.

18. A compound according to claim 2 of the formula:

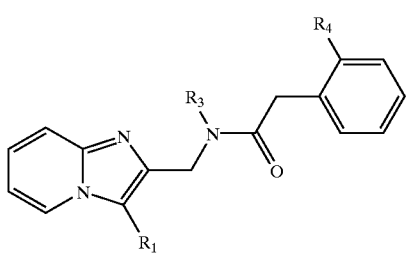

wherein:
  $R_1$, and $R_3$ are as defined in claim 1 and $R_4$ represents halogen or trifluoromethyl.

19. A compound according to claim 17 wherein $R_1$ and $R_4$ are as defined in claim 18 and $R_3$ is isoamyl or n-pentyl.

20. A compound according to claim 3 of the formula:

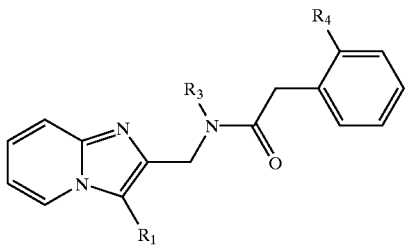

wherein
  $R_1$, and $R_3$ are as defined in claim 3 and $R_4$ represents hydrogen, halogen or trifluoromethyl.

21. A compound according to claim 20 wherein $R_1$ and $R_4$ are as defined in claim 19 and $R_3$ is isoamyl or n-pentyl.

22. A compound according to claim 2, which is selected from:
  (2-Chloro-3,4-dimethoxyphenyl)-N-({3-[(5-bromo-2-hydroxyphenyl)methyl](imidazolo[1,2-a]pyridin-2-yl)}methyl)-N-(3-methylbutyl)carboxamide;
  Ethyl 2-{4-bromo-2-[(2-{[(2-chloro-3,4-dimethoxyphenyl)-N-(3-methylbutyl)carbonylamino]methyl}(imidazolo[1,2-a]pyridin-3-yl))methyl]phenoxy}acetate;
  2-{4-Bromo-2-[(2-{[(2-chloro-3,4-dimethoxyphenyl)-N-(3-methylbutyl)carbonylamino]methyl}(imidazolo[1,2-a]pyridin-3-yl))methyl]phenoxy}acetic acid;
  (2-chloro-3,4-dimethoxyphenyl)-N-({3-[(2-methoxy-5-(3-pyridyl)phenyl)methyl](imidazolo[1,2-a]pyridin-2-yl)}methyl)-N-(3-methylbutyl)carboxamide;
  N-({3-[(5-bromo-2-methoxyphenyl)methyl](imidazolo[1,2-a]pyridin-2-yl)}methyl)(2-chloro-3,4-dimethoxyphenyl)-N-(3-methylbutyl)carboxamide;
  N-({3-[(5-bromo-2-methoxyphenyl)methyl](imidazolo[1,2-a]pyridin-2-yl)}methyl)(2-chloro-3,4-dimethoxyphenyl)-N-(n-pentyl)carboxamide;
  N-({3-[(2-methoxy-5-(3-thienyl)phenyl)methyl](imidazolo[1,2-a]pyridin-2-yl)}methyl)(2-chloro-3,4-dimethoxyphenyl)-N-(3-methylbutyl)carboxamide;
  N-({3-[(2-methoxy-5-(3-aminophenyl)phenyl)methyl](imidazolo[1,2-a]pyridin-2-yl)}methyl)(2-chloro-3,4-dimethoxyphenyl)-N-(3-methylbutyl)carboxamide;
  N-({3-[(2-methoxy-5-(2-methoxyphenyl)phenyl)methyl](imidazolo[1,2-a]pyridin-2-yl)}methyl)(2-chloro-3,4-dimethoxyphenyl)-N-(3-methylbutyl)carboxamide; and
  N-({3-[(2-methoxy-5-(3-methoxyphenyl)phenyl)methyl](imidazolo[1,2-a]pyridin-2-yl)}methyl)(2-chloro-3,4-dimethoxyphenyl)-N-(3-methylbutyl)carboxamide.

23. A compound according to claim 2, which is selected from:
  N-({3-[(2-methoxy-5-(4-methoxyphenyl)phenyl)methyl](imidazolo[1,2-a]pyridin-2-yl)}methyl)(2-chloro-3,4-dimethoxyphenyl)-N-(3-methylbutyl)carboxamide;
  N-({3-[(2-methoxy-5-(2-naphthyl)phenyl)methyl](imidazolo[1,2-a]pyridin-2-yl)}methyl)(2-chloro-3,4-dimethoxyphenyl)-N-(3-methylbutyl)carboxamide;
  N-({3-[(5-(n-butyl)-2-methoxyphenyl)methyl](imidazolo[1,2-a]pyridin-2-yl)}methyl)(2-chloro-3,4-dimethoxyphenyl)-N-(3-methylbutyl)carboxamide; and N-({3-[(5-bromo-2-methoxyphenyl)methyl](imidazolo [1,2-a]pyridin-2-yl)}methyl)(2-chloro-3,4-dimethoxyphenyl)-N-(3-methylbutyl)carboxamide.

24. A compound according to claim 2, which is selected from:

N-({3-[(5-bromo-2-methoxyphenyl)methyl](imidazolo[1,2-a]pyridin-2-yl)}methyl)(2-chloro-4-isopropoxyphenyl)-N-(3-methylbutyl)carboxamide;

N-({3-[(5-bromo-2-hydroxyphenyl)methyl](imidazolo[1,2-a]pyridin-2-yl)}methyl)(2-chloro-4-isopropoxyphenyl)-N-(3-methylbutyl)carboxamide;

Ethyl 2-{4-bromo-2-[(2-{[(2-chloro-4-isopropoxyphenyl)-N-(3-methylbutyl)carbonylamino]methyl}(imidazolo [1,2-a]pyridin-3-yl))methyl]phenoxy}acetate;

2-{4-bromo-2-{[(2-chloro-4-isopropoxyphenyl)-N-(3-methylbutyl)carbonylamino]methyl}(imidazolo[1,2-a]pyridin-3-yl))methyl]phenoxy}acetic acid;

N-({3-[(2-methoxy-5-(3-thienyl)phenyl](imidazolo[1,2-a]pyridin-3-yl))methyl](2-chloro-4-isopropoxyphenyl)-N-(3-methylbutyl)carboxamide;

N-({3-[(2-hydroxy-5-(3-thienyl)phenyl](imidazolo[1,2-a]pyridin-2-yl)}methyl)(2-4-isopropoxyphenyl)-N-(3-methylbutyl)carboxamide;

2-{4-(3-thienyl)-2-[(2-{[(2-chloro-4-isopropoxyphenyl)-N-(3-methylbutyl) carbonylamino]methyl}(imidazolo[1,2-a]pyridin-3-yl))methyl]phenoxy}acetic acid;

N-({3-[(2-methoxyphenyl)methyl](imidazolo)[1,2-a]pyridin-2-yl)}methyl)(2-chloro-3,4-dimethoxyphenyl)-N-(3-methylbutyl)carboxamide;

N-({3-[(2-chlorophenyl)methyl](imidazolo[1,2-a]pyridin-2-yl)}methyl)(2-chloro-3,4-dimethoxyphenyl)-N-(3-methylbutyl)carboxamide; and N-({3-(benzyl)(imidazolo[1,2-a]pyridin-2-yl)}methyl)(2-chloro-3,4-dimethoxyphenyl)-N-(3-methylbutyl)carboxamide.

25. A compound according to claim 2, which is selected from:

(2-chloro-4-methoxy-3-(2-cyclopentylaminoethoxy)phenyl)-N-({3-[(2-methoxyphenyl)methyl](imidazolo[1,2-a]pyridin-2-yl)}methyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-(2-pyrrolidinylethoxy)phenyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-(2-piperidinylethoxy)phenyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-(2-morpholinoethoxy)phenyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-(2-thiomorpholinoethoxy)phenyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-[2-(n-butylamino)ethoxy]phenyl)-N-(3-methylbutyl)carboxamide;

N-({3-[(5-bromo-2-methoxyphenyl)methyl](imidazolo[1,2-a]pyridin-2-yl)}methyl)(2-chloro-4-methoxy-3-[2-(2-methylpropylanino)ethoxy]phenyl)-N-(3-methylbutyl)carboxamide;

(2-chloro-3,4-dimethoxyphenyl)-N-({3-[(2,5-dimethoxyphenyl)methyl](imidazolo[1,2-a]pyridin-2-yl)}methyl)-N-(3-methylbutyl)carboxamide;

N-({3-[(2,5-dimethoxyphenyl)methyl]-6-chloro(imidazolo[1,2-b]pyridazin-2-yl)}methyl)(2-chloro-3,4-dimethoxyphenyl-N-(3-methylbutyl)carboxamide;

N-({3-[(5-bromo-2-methoxyphenyl)methyl](5H,6H,7H,8H-tetrahydroimidazolo[1,2-b]pyridazin-2-yl)}methyl)(2-chloro-3,4-dimethoxyphenyl)-N-(3-methylbutyl)carboxamide; and N-({3-[(5-bromo-2-methoxyphenyl)methyl]-6-ethoxy(imidazolo [1,2-b]pyridazin-2-yl)}methyl)(2-chloro-3,4-dimethoxyphenyl)-N-(3-methylbutyl)carboxamide.

26. A compound according to claim 2, which is:

N-({3-[(5-bromo-2-methoxyphenyl)methyl]-6-(methylamino) (imidazolo[1,2-b]pyridazin-2-yl)}methyl)(2-chloro-3,4-dimethoxyphenyl)-N-(3-methylbutyl)carboxamide.

27. A pharmaceutical composition comprising a compound according to claim 1 together with at least one pharmaceutically acceptable carrier or excipient.

28. A packaged pharmaceutical composition comprising a pharmaceutical composition of claim 27 in a container and instructions for using the composition to treat a patient in need thereof.

29. The packaged pharmaceutical composition of claim 28, wherein said patient is suffering from renal disease, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility, glaucoma, asthma, rhinitis, brain cancer, or a brain tumor.

30. A method for the treatment of physiological disorders associated with excess of or insufficient amount of bradykinin, which method comprises administration to a patient in need thereof a bradykinin reducing amount of a compound according to any one of claims 1 to 4 or a bradykinin enhancing amount of a compound according to any one of claims 1 to 4.

31. A method for the treatment of a patient suffering from renal disease, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility, glaucoma, asthma, or rhinitis, which comprises administering a sufficient amount of a compound according to claim 1 to alter the symptoms of such disease.

32. A method of increasing the permeability of the blood brain barrier which comprises administering a compound according to claim 1 to a patient.

33. A method of increasing the brain concentration of a CNS active compound which comprises administering a compound according to claim 1 and the CNS active compound to a patient.

34. A method for localizing bradykinin receptors in tissue section samples comprising:

contacting with a sample of tissue a detectably-labeled compound of claim 1, under conditions that permit binding of the compound to the sample of tissue; washing the tissue sample to remove unbound compound; and detecting the bound compound.

35. The method of claim 34, wherein the compound is radiolabeled.

36. A method of inhibiting the binding of bradykinin to the BK-2 receptor, which method comprises contacting, in the presence of bradykinin, a solution comprising a compound of claim 1, with cells expressing the BK-2 receptor, wherein the compound is present in the solution at a concentration sufficient to reduce levels of bradykinin binding to cells expressing the BK-2 receptor in vitro.

37. A method for altering the signal-transducing activity of a cell surface BK-2 receptor, said method comprising contacting cells expressing such a receptor with a solution comprising a compound according to claim 1, wherein the compound is present in the solution at a concentration sufficient to reduce levels of NPY binding to cells expressing the $NPY_5$ receptor in vitro.

38. A compound according to claim 1, wherein in an assay of BK-2 binding the compound exhibits an $K_i$ of 1 micromolar or less.

39. A compound according to claim 1, wherein in an assay of BK-2 binding the compound exhibits an $K_i$ of 100 nanomolar or less.

40. A compound according to claim 1, wherein in an assay of BK-2 binding the compound exhibits an $K_i$ of 10 nanomolar or less.

* * * * *